(12) United States Patent
Manku et al.

(10) Patent No.: US 9,827,219 B2
(45) Date of Patent: Nov. 28, 2017

(54) COMPOSITIONS AND METHODS FOR LOWERING LEVELS OF HIGH-SENSITIVITY C-REACTIVE PROTEIN (HS-CRP) IN A SUBJECT

(71) Applicant: Amarin Pharmaceuticals Ireland Limited, Dublin (IE)

(72) Inventors: Mehar Manku, Birmingham (GB); Ian Osterloh, Kent (GB); Pierre Wicker, Mystic, CT (US); Rene Braeckman, Richboro, PA (US); Paresh Soni, Mystic, CT (US)

(73) Assignee: AMARIN PHARMACEUTICALS IRELAND LIMITED, Dublin (IE)

( * ) Notice: Subject to any disclaimer, the term of this patent is extended or adjusted under 35 U.S.C. 154(b) by 0 days.

(21) Appl. No.: 13/735,660

(22) Filed: Jan. 7, 2013

(65) Prior Publication Data

US 2013/0189355 A1 Jul. 25, 2013

Related U.S. Application Data

(60) Provisional application No. 61/584,013, filed on Jan. 6, 2012, provisional application No. 61/670,408, filed on Jul. 11, 2012, provisional application No. 61/656,347, filed on Jun. 6, 2012.

(51) Int. Cl.
| | |
|---|---|
| A61K 9/48 | (2006.01) |
| A61K 31/232 | (2006.01) |
| A61K 31/202 | (2006.01) |
| A61K 31/366 | (2006.01) |
| A61K 31/40 | (2006.01) |
| A61K 31/505 | (2006.01) |

(52) U.S. Cl.
CPC .............. *A61K 31/232* (2013.01); *A61K 9/48* (2013.01); *A61K 31/202* (2013.01); *A61K 31/366* (2013.01); *A61K 31/40* (2013.01); *A61K 31/505* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,343,389 A | 8/1994 | Otvos |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |
| 6,025,008 A | 2/2000 | Akahoshi |
| 6,069,168 A | 5/2000 | Horrobin et al. |
| 6,193,999 B1 | 2/2001 | Gennadios |
| 6,284,268 B1 | 9/2001 | Mishra et al. |
| 6,313,330 B1 | 11/2001 | Kiyohara et al. |
| 6,326,031 B1 | 12/2001 | Hsia et al. |
| 6,326,355 B1 | 12/2001 | Abbruzzese et al. |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

A study of AMR101 to evaluate its ability to reduce cardiovascular events in high risk patients with hypertriglyceridemia and on statin (REDUCE-IT). Available at: http://clinicaltrials.gov/show/NCT01492361.

Aarsland, et al., "On the Effect of Peroximsomal beta-Oxidation and Carnitine Palmitoyltransferase Activity by Eicosapentaenoic Aid in Live and Heart of Rats." Lipids, 25:546-548, (1990).

Aas, V., et al., "Eicosapentaenoic acid (20:5 n-3) increases fatty acid and glucose uptake in cultured human skeletal muscle cells." Journal of Lipid Research, 47:366-374 (2006).

(Continued)

*Primary Examiner* — Susan Tran

(74) *Attorney, Agent, or Firm* — Perkins Coie LLP

(57) ABSTRACT

The present disclosure provides methods for treating and/or preventing cardiovascular-related disease and, in particular, a method of blood lipid therapy comprising administering to a subject in need thereof a pharmaceutical composition comprising eicosapentaenoic acid or a derivative thereof. In some embodiments, the method comprises lowering high sensitivity CRP (hs-CRP) levels in a subject including, for example, a subject with a $HbA_{1c}$ value of about 5.00 %-8.50 % or at least about 6.8 %.

17 Claims, 6 Drawing Sheets

(56) References Cited

U.S. PATENT DOCUMENTS

| | | |
|---|---|---|
| 6,331,568 B1 | 12/2001 | Horrobin |
| 6,368,621 B1 | 4/2002 | Engel et al. |
| 6,384,077 B1 | 5/2002 | Peet |
| 6,479,544 B1 | 11/2002 | Horrobin |
| 6,531,150 B1 | 3/2003 | Sunohara et al. |
| 6,555,700 B1 | 4/2003 | Horrobin et al. |
| 6,620,821 B2 | 9/2003 | Robl |
| 6,689,812 B2 | 2/2004 | Peet |
| 6,846,942 B2 | 1/2005 | Rubin |
| 7,022,713 B2 | 4/2006 | Aoki et al. |
| 7,112,609 B2 | 9/2006 | Hermelin et al. |
| 7,119,118 B2 | 10/2006 | Peet |
| 7,205,329 B2 | 4/2007 | Chien et al. |
| 7,405,302 B2 | 7/2008 | Hutchinson et al. |
| 7,498,359 B2 | 3/2009 | Yokoyama et al. |
| 7,511,131 B2 | 3/2009 | Crooke et al. |
| 7,598,227 B2 | 10/2009 | Crooke et al. |
| 7,776,881 B2 | 8/2010 | Aoki et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 8,431,560 B1 | 4/2013 | Manku et al. |
| 8,440,650 B1 | 5/2013 | Manku et al. |
| 8,518,929 B2 | 8/2013 | Manku et al. |
| 8,524,698 B2 | 9/2013 | Manku et al. |
| 8,546,372 B2 | 10/2013 | Manku et al. |
| 8,551,521 B2 | 10/2013 | Manku et al. |
| 8,563,608 B2 | 10/2013 | Manku et al. |
| 8,617,593 B2 | 12/2013 | Manku et al. |
| 8,617,594 B2 | 12/2013 | Manku et al. |
| 8,618,168 B2 | 12/2013 | Fujii et al. |
| 8,623,406 B2 | 1/2014 | Manku et al. |
| 8,642,077 B2 | 2/2014 | Manku et al. |
| 8,669,245 B2 | 3/2014 | Osterloh et al. |
| 8,680,144 B2 | 3/2014 | Osterloh et al. |
| 8,691,871 B2 | 4/2014 | Osterloh et al. |
| 8,703,185 B2 | 4/2014 | Manku et al. |
| 8,709,475 B2 | 4/2014 | Manku et al. |
| 8,906,964 B2 | 12/2014 | Bobotas et al. |
| 9,006,285 B2 | 4/2015 | Ohnishi |
| 9,060,981 B2 | 6/2015 | Sato et al. |
| 9,452,150 B2 | 9/2016 | Ueshima et al. |
| 2001/0035125 A1 | 11/2001 | Talieh et al. |
| 2002/0016312 A1 | 2/2002 | Seed et al. |
| 2002/0025983 A1 | 2/2002 | Horrobin |
| 2002/0035125 A1 | 3/2002 | Shear |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0204356 A1* | 10/2004 | Guenzler-Pukall .... A61K 31/00 514/1.9 |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0252833 A1 | 11/2006 | Peet et al. |
| 2007/0021504 A1 | 1/2007 | Yokoyama et al. |
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0265340 A1 | 11/2007 | Shalwitz et al. |
| 2007/0269507 A1 | 11/2007 | Sachetto et al. |
| 2008/0020018 A1 | 1/2008 | Moodley et al. |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0185198 A1 | 8/2008 | Jones |
| 2008/0200547 A1 | 8/2008 | Peet et al. |
| 2008/0200707 A1 | 8/2008 | Shimano et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0156675 A1 | 6/2009 | Yokoyama et al. |
| 2009/0182049 A1 | 7/2009 | Opheim |
| 2009/0227602 A1 | 9/2009 | Griffin et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0178105 A1 | 7/2011 | Gillies et al. |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |

(56) References Cited

U.S. PATENT DOCUMENTS

| | | |
|---|---|---|
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | Macdonald et al. |
| 2012/0195963 A1 | 8/2012 | Peet et al. |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0264824 A1 | 10/2012 | Mizuguchi et al. |
| 2012/0302589 A1 | 11/2012 | Manku et al. |
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1* | 10/2013 | Button et al. .................. 435/14 |
| 2013/0281534 A1 | 10/2013 | Osterloh et al. |
| 2013/0295173 A1 | 11/2013 | Machielse et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0157592 A1 | 6/2015 | Soni |
| 2015/0164850 A1 | 6/2015 | Osterloh et al. |
| 2015/0190361 A1 | 7/2015 | Osterloh et al. |
| 2015/0265574 A1 | 9/2015 | Rowe |
| 2015/0290154 A1 | 10/2015 | Roberts et al. |
| 2016/0213639 A1 | 7/2016 | Suzuki et al. |
| 2017/0035722 A1 | 2/2017 | Soni |

FOREIGN PATENT DOCUMENTS

| | | |
|---|---|---|
| CA | 2675836 | 7/2008 |
| CA | 2724983 | 11/2009 |
| CN | 101252837 | 8/2008 |
| EP | 273708 | 7/1988 |
| EP | 277747 | 8/1988 |
| EP | 0302482 | 2/1989 |
| EP | 347509 | 12/1989 |
| EP | 0460917 | 12/1991 |
| EP | 606012 | 7/1994 |
| EP | 0610506 | 8/1994 |
| EP | 0641562 A1 | 3/1995 |
| EP | 1125914 | 8/2001 |
| EP | 1157692 | 11/2001 |
| EP | 1296670 | 4/2003 |
| EP | 1549299 | 12/2003 |
| EP | 1743644 | 1/2007 |
| EP | 1 790 339 A1 | 5/2007 |
| EP | 1 834 639 A1 | 9/2007 |
| EP | 1 982 710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2719382 A1 | 4/2014 |
| EP | 2792746 | 10/2014 |
| FR | 2635263 | 2/1990 |
| GB | 2148713 | 6/1985 |
| GB | 2221843 | 2/1990 |
| GB | 2229363 | 9/1990 |
| GB | 9901809.5 | 1/1999 |
| JP | 61035356 | 2/1986 |
| JP | 04182426 | 6/1992 |
| JP | 2003306690 | 10/2003 |
| JP | 07 238598 | 9/2007 |
| JP | 08 050367 | 3/2008 |
| KR | 10-2006-0109988 | 10/2006 |
| KR | 10-2007-0058460 | 6/2007 |
| WO | WO 90/04391 | 5/1990 |
| WO | WO 92/21335 | 12/1992 |
| WO | WO 94/28891 | 12/1994 |
| WO | WO 95/24459 | 9/1995 |
| WO | WO 96/36329 | 11/1996 |
| WO | WO 97/39759 | 10/1997 |
| WO | WO 98/16216 | 4/1998 |
| WO | WO 99/26583 | 6/1999 |
| WO | WO 99/29316 | 6/1999 |

(56) References Cited

FOREIGN PATENT DOCUMENTS

| | | |
|---|---|---|
| WO | WO 00/44361 | 8/2000 |
| WO | WO 00/51573 | 9/2000 |
| WO | WO 01/15552 | 3/2001 |
| WO | WO 02/02105 | 1/2002 |
| WO | WO 02/058793 | 8/2002 |
| WO | WO 02/089787 | 11/2002 |
| WO | WO 02/096408 | 12/2002 |
| WO | 03/068216 | 8/2003 |
| WO | WO 03/068216 | 8/2003 |
| WO | WO 2004/050913 | 6/2004 |
| WO | WO 2004/064716 | 8/2004 |
| WO | 2004/078166 | 9/2004 |
| WO | WO 2004/078166 | 9/2004 |
| WO | WO 2004/082402 | 9/2004 |
| WO | WO 2005/060954 | 7/2005 |
| WO | WO 2005/079797 | 9/2005 |
| WO | WO 2005/079853 | 9/2005 |
| WO | WO 2005/123060 | 12/2005 |
| WO | WO 2005/123061 | 12/2005 |
| WO | WO 2006/017627 | 2/2006 |
| WO | WO 2006/029577 | 3/2006 |
| WO | WO 2006/062748 | 6/2006 |
| WO | WO 2006/096806 | 9/2006 |
| WO | WO 2007/011886 | 1/2007 |
| WO | 2007/017240 | 2/2007 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/091338 | 8/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/088415 | 7/2008 |
| WO | WO 2008/106787 | 9/2008 |
| WO | WO 2008/115529 | 9/2008 |
| WO | WO 2008/145170 | 12/2008 |
| WO | WO 2009/004999 | 1/2009 |
| WO | WO 2010/028067 | 3/2010 |
| WO | WO2010028067 A1 * | 3/2010 |
| WO | WO 2010/093634 | 8/2010 |
| WO | WO 2010/127099 | 11/2010 |
| WO | WO 2010/127103 | 11/2010 |
| WO | WO 2010/147994 | 12/2010 |
| WO | WO 2011/038122 | 3/2011 |
| WO | WO 2011/109724 | 9/2011 |
| WO | WO 2012/074930 | 6/2012 |
| WO | WO 2013/070735 | 5/2013 |
| WO | WO2013/103958 | 7/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO 2014/057522 | 4/2014 |
| WO | WO2014/074552 | 5/2014 |
| WO | WO2014/134466 | 9/2014 |
| WO | WO2015/021141 | 2/2015 |
| WO | WO2015/066512 | 5/2015 |

OTHER PUBLICATIONS

Abbey, M., et al., "Effect of fish oil on lipoproteins, lecithin:cholesterol acyltransferase, and lipidtransfer protein activity in humans" Arterioscler. Thromb. Vasc. Biol. 10:85-94 (1990).
Abela GS, Aziz K. Cholesterol crystals cause mechanical damage to biological membranes: a proposed mechanism of plaque rupture and erosion leading to arterial thrombosis. Clin. Cardiol. 2005;28(9):413-420.
Abelo A, Andersson TB, Antonsson M, et al. Stereoselective metabolism of omeprazole by human cytochrome P450 enzymes. Drug Metab. Dispos. Aug. 28, 2000 (8): 966-72.
Ackman et al., The "Basic" Fatty Acid Composition of Atlantic Fish Oils: Potential Similarties Useful for Enrichment of Polyunsaturated Fatty Acids by Urea Complexation, JAOCS, vol. 65, 1:136-138 (Jan. 1988).
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (1999).
Adan, Y., et al., "Concentration of serum lipids and aortic lesion size in female and male apo E-deficient mice fed docosahexaenoic acid." Biosci. Biotechnol. Biochem. 63(2):309-313 (1999).
Agren JJ, Vaisanen S, Hanninen O, et al. Hemostatic factors and platelet aggregation after a fish-enriched diet or fish oil or docosahexaenoic acid supplementation. Prostaglandins Leukot Essent Fatty Acids Oct. 1997 57 (4-5): 419-21.
Agren, J.J. et al., "Fatty acid composition of erythrocyte, platelet, and serum lipids in strict vegans." Lipids 30:365-369 (1995).
Agren, J.J., et al., "Fish diet, fish oil and docosahexaenoic acid rich oil lower fasting and postprandial plasma lipid levels." Eur J Clin Nutr., 50:765-771. (1996).
Aguilar-Salinas et al., "High Prevalence of Low HDL Cholesterol Concentrations and Mixed Hyperlipidemia in a Mexican Nationwide Survey," J Lipid Res., 2001, 42:1298-1307.
Ai M, Otokozawa S, Asztalos BF, Ito Y, Nakajima K, White CC, Cupples LA, Wilson PW, Schaefer EJ. Small dense LDL cholesterol and coronary heart disease: results from the Framingham Offspring Study. Clin. Chem. 2010;56(6):967-976.
Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (2003).
Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (1989).
Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (2008).
Allard et al. "Nutritional assessment and hepatic fatty acid composition in non-alcoholic fatty liver disease (NAFLD): a cross-sectional study." J Hepatol. Feb. 2008;48(2):300-7.
Allred, C., et al., "PPARy1 as a molecular target of eicosapentaenoic acid in human colon cancer (HT-29) cells." J. Nutr. 138:250-256 (2008).
Almeida et al., "Effect of nebicapone on the pharmacokinetics and pharmacodynamics of warfarin in healthy subjects." Eur J Clin Pharmacol. Oct. 2008;64(10):961-6.
Amarin Appoints Medpace as CRO for Two Phase 3 Cardiovascular Trials, published Oct. 19, 2009.
Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from the Internet: <http://inestor.amarincorp.com/releasedetail.cfm?ReleaseID=504380>.
Amarin Presentation "Next Generation Lipid Modification in Cardiovascular Disease," (Mar. 2010).
Amarin press release (Jan. 18, 2008).
Amarin Proceeding to Phase 3 with AMR101 for Hypertriglyceridemia, published Jul. 23, 2008.
Amarin, Information Sheet, 2010.
Amarin's SEC filing dated Oct. 12, 2005.
Amarin's Vascepa® Briefing Document for the Endocrinologic and Metabolic Drugs Advisory Committee Meeting dated Oct. 16, 2013, 117 pages.
Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis*. 1996;124(2):261-271.
Anderson TJ, Gregoire J, Hegele RA, et al. 2012 update of the Canadian Cardiovascular Society guidelines for the diagnosis and treatment of dyslipidemia for the prevention of cardiovascular disease in the adult. Can. J. Cardiol. 2013;29:151-167.

(56) References Cited

OTHER PUBLICATIONS

Anderson TJ, Meredith IT, Yeung AC, Frei B, Selwyn AP, Ganz P. The effect of cholesterol-lowering and antioxidant therapy on endothelium-dependent coronary vasomotion. N. Engl. J. Med. 1995;332:488-493.

Anderson, "Lipoprotein-Associated Phospholipase A2: An Independent Predictor of Coronary Artery Disease Events in Primary and Secondary Prevention," 101 Am. J. Cardiology 23-F (2008).

Ando, M., et al., "Eicosapentanoic acid reduces plasma levels of remnant lipoproteins and prevents in vivo peroxidation of LDL in dialysis patients." J. Am. Soc. Nephrol., 10:2177-2184 (1999).

Ando, Y., et al., "Positional distribution of highly unsaturated fatty acids in triacyl-sn-glycerols of Artemia Nauplii enriched with docosahexaenoic acid ethyl ester." Lipids 36:733-740 (2001).

Andrade, SE. et al., "Discontinuation of antihyperlipidaemic drugs_do rates reported in clinical trials reflect rates in primary care settings?" New Eng. J. Med. 332: 1125-1131. (1995).

Andrews HE, Bruckdorfer KR, Dunn RC, Jacobs M. Low-density lipoproteins inhibit endotheliumdependent relaxation in rabbit aorta. Nature. 1987;327:237-239.

Angerer et al., "n-3 Polyunsaturated Fatty Acids and the Cardiovascular System", Current Opinion in Lipidology, 11(1):57-63, (2000).

Anil, Eliz, "The Impact of EPA and DHA on Blood Lipids and Lipoprotein Metabolism: Influence of ApoE Genotype", Proceedings of the Nutrition Society, 66:60-68, (2007).

Annex to Rule 161 Response dated Apr. 16, 2012.

Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).

Appendix A to Defendants' Invalidity Contentions, 3:14-CV-02550-MLC-DEA (D.N.J.), 478 pages (Dec. 5, 2014).

Appleton, Katherine M., et al., "Effects of n-3 long-chain polyunsaturated fatty acids on depressed mood: systematic review of published trials", Am. J. Clin. Nutr., 84(6):1308-1316, (Dec. 2006).

Arrol, S. et al., "The effects of fatty acids on apolipoprotein B secretion by human hepatoma cells (HEP G2)," Atherosclerosis 150:255-264. (2000).

Arshad, A., et al., "Sudden cardiac death and the role of medical therapy." Progress in Cardiovascular Diseases, vol. 50, No. 6, 420-438, (2008).

Arterburn, L., et al., "Distribution, interconversion, and dose response of n-3 fatty acids in humans." Am J Clin Nutr., 83:1467S-76S (2006).

Asano, M., et al., "Eicosapentaenoic acid inhibits vasopressin-activated Ca2q influx and cell proliferation in rat aortic smooth muscle cell lines." European Journal of Pharmacology 379:199-209 (1999).

Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (1997).

Asthma, 10(3):65-68 (1997).

ATP III guidelines, NIH publication No. 01-3305 (2001).

Attie AD, et al., "Relationship between stearoyl-CoA desaturase activity and plasma trigylcerides in human and mouse hypertriglyceridemia," J. Lipid Res. 2002;43:1899-907.

Ault, "Prescription omega-3 fatty acid formulation approved," Ob.Gyn.News, (Jan. 15, 2005).

Avandia [package insert]. Research Triangle Park, NC: GlaxoSmithKline; 2011.

Aviram M, Rosenblat M, Bisgaier CL, Newton RS. Atorvastatin and gemfibrozil metabolites, but not the parent drugs, are potent antioxidants against lipoprotein oxidation. Atherosclerosis. 1998; 138(2):271-280.

Ayton, et al., "A pilot open case series of Ethyl-EPA supplementation in the treatment of anorexia nervosa," Prostaglandins, Leukotrienes and Essential Fatty Acids 71, pp. 205-209. (2004).

Ayton, et al., "Rapid improvement of severe anorexia nervosa during treatment with ethyl-eicosapentaenoate and micronutrients," European Psychiatry 19, pp. 317-319. (2004).

Baigent, C., et al., "Efficacy and safety of cholesterol-lowering treatment: prospective meta-analysis of data from 90,056 participants in 14 randomised trials of statins." Lancet; 366:1267-1278. (2005).

Baldwin RM, Ohlsson S, Pedersen RS, et al. Increased omeprazole metabolism in carriers of the CYP2C19*17 allele; a pharmacokinetic study in healthy volunteers. *Br. J. Clin. Pharmacol.* May 2008 65 (5): 767-74.

Baldwin SJ, Clarke SE, Chenery RJ. Characterization of the cytochrome P450 enzymes involved in the in vitro metabolism of rosiglitazone. Br. J. Clin. Pharmacol. 1999;48:424-432.

Balk, E.M., et al., "Effects of omega-3 fatty acids on serum markers of cardiovascular disease risk: a systematic review. Atherosclerosis." 189:19-30. (2006).

Ballantyne CM, Bays HE, Kastelein JJ, et al. Efficacy and safety of eicosapentaenoic acid ethyl ester (AMR 101) therapy in statin-treated patients with persistent high triglycerides (from the ANCHOR study). Am J Cardiol Oct. 2012 110 (7): 984-92.

Ballantyne et al., "Abstract 15071: AMR101 Lowers Triglycerides, Atherogenic Lipoprotein, Phospholipase $A_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.

Ballantyne et al., "Effects of icosapent ethyl on lipoprotein particle concentration and the fatty acid desaturation index in statiotreated patients with persistent high triglycerides (the ANCHOR study)." Journ. Clin. Lipidology, 2013, 7(3):270-271.

Ballantyne et al., Influence of low-high density lipoprotein cholesterol and elevated triglyceride on coronary heart disease events and response to simvastatin therapy in 4S, Circulation, 104:3046-3051. (2001).

Bang HO, Dyerberg J. "Plasma lipids and Lipoproteins in Greenlandic west coast Eskimos" Acta Med Scand, 192:85-94. (1972).

Banga, A. et al., "Adiponectin translation is increased by the PPAR? agonists pioglitazone and ?-3 fatty acids." Am J Physiol Endocrinol Metab 296:480-489 (2009).

Bangham et al., "Diffusion of univalent ions across the lamellae of swolloen phospholipids." J. Mol. Biol. (1965) 13(1):238-252.

Bansal S, Buring JE, Rifai N, Mora S, Sacks FM, Ridker PM, "Fasting Compared With Nonfasting Triglycerides and Risk of Cardiovascular Events in Women," JAMA, 298:309-316 (2007).

Barter et al., "Effectiveness of Combined Statin Plus Omega-3 Fatty Acid Therapy for Mixed Dyslipidemia." Am. J. Cardiol. 102(8):1040-1045 (Oct. 15, 2008).

Basu, A. et al., "Dietary Factors That Promote or Retard Inflammation." Arterioscler. Thromb. Vasc. Biol. 26:995-1001 (2006).

Baynes JW. Role of oxidative stress in development of complications in diabetes. Diabetes. 1991;40(4):405-412.

Bays HE et al. "Prescription omega 3 fatty acids and their lipid effects: physiologic mechanisms of action and clinical implications," Expert Rev Cardiovasc Ther., 6:391-409. (2008).

Bays HE, Ballantyne CM, Braeckman RA, Stirtan WG, Soni PN. Icosapent ethyl, a pure ethyl ester of eicosapentaenoic acid: effects on circulating markers of inflammation from the MARINE and ANCHOR studies. Am. J. Cardiovasc. Drugs. 2013;13(1):37-46.

Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. 2012;6:565-572.

Bays HE, Safety considerations with omega-3 fatty acid therapy. Am. J. Cardiol. Mar. 2007 99 (6A): 35C-43C.

Bays, H., Clinical Overview of Omacor: A Concentrated Formulation of Omega-3 Polyunsaturated Fatty Acids, Am J Cardiol.; 98[suppl]:71i-76i (2006).

Bays, H., "Rationale for Prescription Omega-3-Acid Ethyl Ester Therapy for Hypertriglyceridemia: A Primer for Clinicians," Drugs of Today, 44(3); 205-246. (2008).

(56) References Cited

OTHER PUBLICATIONS

Bays, H.E., Eicosapentaenoic Acid Ethyl Ester (AMR101) Therapy in Patients With Very High Triglyceride Levels (from the Multicenter, plAcebo-controlled, Randomized, double-blINd, 12-week study with an open-label Extension [MARINE] Trial) Am J Cardiol;108:682-690. (2011).
Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (2010).
Beal, M.F., Annals of Neurology, vol. 38, No. 3, "Aging, Energy, and Oxidative Stress in Neurodegenerative Diseases", pp. 357-366, (Sep. 1995).
Belarbi et al., "A process for high yield and scaleable recovery of high purity eicosapentaenoic acid esters from microalgae and fish oil," Enzyme and Microbail Technology 26:516-529 (2000).
Belger et al., "Assessment of prefrontal activation by infrequent visual targets and non-target noval stimuli in schisophrenia: a function MRI study," Presented at the 9th Biennial winter workshop on schizophrenia, Davos, Switzerland, Feb. 7-13, 1998, Abstract in Schizophrenia Research. vol. 29. No. 1/02, Jan. 1998.
Belmaker et al., "Addition of Omega-3 Fatty Acid to Maintenance Medication Treatment for Recurrent Unipolar Depressive Disorder," Am. J. Psychiatry, 159:477-479 (2002).
Belmaker, et al., "Omega-3 Eicosapentaenoic Acid in Bipolar Depression: Report of a Small Open-Label Study," J Clin Psychiatry; 66:726-729. (2005).
Bender NK, Kraynak MA, Chiquette E, et al. Effects of marine fish oils on the anticoagulation status of patients receiving chronic warfarin therapy. J. Thromb. Thrombolysis Jul. 5, 1998 (3): 257-61.
Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (1996).
Benn et al., Improving Prediction of Ischemic Cardiovascular Disease in the General Population Using Apolipoprotein B: The Copenhagen City Heart Study, 27 Arteriosclerosis, Thrombosis, & Vascular Biology 661 (2007).
Bennett et al., "Treatment of IgA nephropathy with eicosapentanoic acid (EPA): a two-year prospective trial [Abstract Only]." Clin. Nephrol. 31(3):128-131 (Mar. 1989).
Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (1999).
Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89.
Berliner JA, Watson AD. A role for oxidized phospholipids in atherosclerosis. N. Engl. J. Med. 2005;353(1):9-11.
Bertelsen M, Anggard EE, Carrier MJ. Oxidative stress impairs insulin internalization in endothelial cells in vitro. Diabetologia. 2001;44(5):605-613.
Betteridge, D.J., "Diabetic dyslipidaemia: past, present and future." Practical Diabetes Int, 21(2): 78-85. (2004).
Black et al., "Effect of intravenous eicosapentaenoic acid on cerebral blood flow, edema, and brain prostaglandins in ischemic gerbils", Prostaglandins, 28(4), pp. 545-546. (1984).
Blankenhorn D.H. et al., "Beneficial effects of combined colestipol-niacin therapy on coronary atherosclerosis and coronary venous bypass grafts." JAMA 257: 3233-3240. (1987).
Block, R. C., et al., "EPA and DHA in blood cell membranes from acute coronary syndrome patients and controls." Atherosclerosis, 197(2):821-828 (2007).
Blumenthal, Advanced Studies in Medicine, 2:148-157 (2002).
Boden WE, Probstfield JL, Anderson T, Chaitman BR, Desvignes-Nickens P, Koprowicz K, IJ McBride R, Teo K, Weintraub W. Niacin in patients with low hdl cholesterol levels receiving intensive statin therapy. N. Engl. J. Med. 2011;365:2255-2267.
Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (1992).
Borchman D, Lamba OP, Salmassi S, Lou M, Yappert MC. The dual effect of oxidation on lipid bilayer structure. Lipids. 1992;27(4):261-265.
Bordin et al., "Effects of fish oil supplementation on apolipoprotein B100 production and lipoprotein metabolism in normolipidaemic males," Eur. J. Clin. Nutr. 52: 104-9 (1998).
Borthwick et al., "The effects of an omega-3 ethyl ester concentrate on blood lipid concentrations in pateitns with hyperlipidemia," Clin. Drug Investig. (1998) 15(5): 397-404.
Bossaller C, Habib GB, Yamamoto H, Williams C, Wells S, Henry PD. Impaired muscarinic endothelium-dependent relaxation and cyclic guanosine 5'-monophosphate formation in atherosclerotic human coronary artery and rabbit aorta. J. Clin. Invest. 1987;79:170-174.
Bousserouel, S., et al., "Different effects of n-6 and n-3 polyunsaturated fatty acids on the activation of rat smooth muscle cells by interleukin-1?." J. Lipid Res. 44:601-611 (2003).
Bousserouel, S., et al., "Modulation of cyclin D1 and early growth response factor-1 gene expression in interleukin-1?-treated rat smooth muscle cells by n-6 and n-3 polyunsaturated fatty acids." Eur. J. Biochem. 271:4462-4473 (2004).
Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(2004).
Braeckman RA, Manku MS, Bays HE, Stirtan WG, Soni PN. Icosapent ethyl, a pure EPA omega-3 fatty acid: effects on plasma and red blood cell fatty acids in patients with very high triglyceride levels (results from the MARINE study). Prostaglandins Leukot Essent Fatty Acids. 2013;89(4):195-201.
Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.
Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. 2013;3:101-108.
Braunersreuther V, Steffens S, Arnaud C, Pelli G, Burger F, Proudfoot A, Mach F. A novel rantes antagonist prevents progression of established atherosclerotic lesions in mice. Arterioscler. Thromb. Vasc. Biol. 2008;28:1090-1096.
Breslow, J., "n-3 Fatty acids and cardiovascular disease." Am J Clin Nutr., 83:1477S-82S (2006).
Brinton EA, Ballantyne CM, Bays HE, Kastelein JJ, Braeckman RA, Soni PN. Effects of AMR101 on lipid and inflammatory parameters in patients with diabetes mellitus-2 and residual elevated triglycerides (200-500 mg/dl) on statin therapy at LDL-C goal: the ANCHOR study [abstract 629-P]. Diabetes. 2012;61(suppl 1): A159-A160.
Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (1996).
Brouwer, I.A. et al., "Effect of fish oil on ventricular tachyarrhythmia and death in patients with implantable cardioverter defibrillators." JAMA. 295(22):2613-2619 (2006).
Brovkovych V, Dobrucki LW, Brovkovych S, Dobrucki I, Do Nascimento CA, Burewicz A, Malinski T. Nitric oxide release from normal and dysfunctional endothelium. J. Physiol. Pharmacol. 1999;50:575-586.
Brown et al., Simvastatin and Niacin, Antioxidant Vitamins, or the Combination for the Prevention of Coronary Disease, N Engl J Med, vol. 345, No. 22, 1583-1592 (Nov. 29, 2001).

(56) References Cited

OTHER PUBLICATIONS

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (1999).
Brown, A. J., et al., "Persistent changes in the fatty acid composition of erythrocyte membranes after moderate intake of n-3 polyunsaturated fatty acids: study design and implications." Am.J. Clin. Nutri. 54:668-73(1991).
Brown, G., et al., "Regression of coronary artery-disease as a result of intensive lipid-lowering therapy in men with high levels of apolipoprotein," B., N. Engl. J. Med. 323:1289-1298. (1990).
Brownlee M. Biochemistry and molecular cell biology of diabetic complications. Nature. 2001; 414(6865):813-820.
Bryhn, M., et al., "The bioavailability and pharmacodynamics of different concentrations of omega-3 acid ethyl esters." Prostaglandins, Leukotrienes and Essential Fatty Acids 75:19-24 (2006).
Budavari, S., Editor, "The Merck Index", Merck & Co., Inc., 2417:379,4511,725, (1989).
Bunting et al. "Depression in Parkinson's Disease". J Neurosci Nurs.; 23(3):158-164. (Abstract Only) (1991).
Burdge, G.C., et al., "Eicosapentaenoic and docosapentaenoic acids are the principal products of a-linolenic acid metabolism in young men." British Journal of Nutrition 88:355-363 (2002).
Burdge, G.C., et al., "Lack of effect of meal fatty acid composition on postprandial lipid, glucose and insulin responses in men and women aged 50-65 years consuming their habitual diets." British Journal of Nutrition, 96:489-500 (2006).
Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (2007).
Burr, M. L., et al., "Effects of changes in fat, fish and fibre intakes on death and myocardial reinfarction: Diet and reinfarction trial." The Lancet, 2(8666):757-61 (1989).
Buse JB, Ginsberg HN, Bakris GL, et al. Primary prevention of cardiovascular diseases in people with diabetes mellitus: a scientific statement from the American Heart Association and the American Diabetes Association. Diabetes Care. 2007;30: 162-172.
Calabresi, L., et al., "Omacor in familial combined hyperlipidemia: effects on lipids and low density lipoprotein subclasses." Atherosclerosis 148:387-396 (2000).
Calder PC. The role of marine omega-3 (n-3) fatty acids in inflammatory processes, atherosclerosis and plaque stability. Mol. Nutr. Food Res. 2012;56(7):1073-1080.
Campos, H., et al., "Lowdensity lipoprotein size, pravastatin treatment, and coronary events." JAMA, 286:1468-1474 (2001).
Canner P.L. et al., "Fifteen year mortality in Coronary Drug Project patients: long-term benefit with niacin," J. Am. Coll. Cardiol. 8. 1245-1255. (1986).
Cao, et al., "Cloning, Expression, and Chromosomal Locatlization . . . ", Genomics, 49:327-331, (1998).
Cao, J. et al., "Incorporation and Clearance of Omega-3 Fatty Acids in Erythrocyte Membranes and Plasma Phospholipids." Clinical Chemistry 52(12):2265-2272 (2006).
Capuzzi, DM et al., "Efficacy and safety of an extended-release niacin (Niaspan): a long-term study." Am. J. Cardiol. 82: 74U-81U. (1998).
Carlson, L.A. & Rosenhamer G., "Reduction of mortality in the Stockholm Ischaemic Heart Disease Secondary Prevention Study by combined treatment with clofibrate and nicotinic acid." Acta Med. Scand. 223, 405-418 (1988).
Carlson, L.A., "Nicotinic acid: the broad spectrum lipid drug. A 50th Anniversary review", J. Int. Med., 258:94-114, (2005).
Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (2007).

Carroll, D. N., et al., "Evidence for the Cardioprotective Effects of Omega-3 Fatty Acids." Ann Pharmacother., 36:1950-6 (2002).
Carulli et al., "Chenodeoxycholic acid and ursodeoxycholic acid effects in endogenous hypertriglyceridemias. A controlled double-blind trial." J. Clin. Pharmacol., 21(10):436-42 (1981).
Cazzola, R., et al., "Age- and dose-dependent effects of an eicosapentaenoic acid-rich oil on cardiovascular risk factors in healthy male subjects." Atherosclerosis 193:159-167 (2007).
Cefali, E.A., et al., "Aspirin reduces cutaneous flushing after administration of an optimised extended-release niacin formulation", Int. J. Clin. Pharmacol. & Ther., 45:78-88, (2007).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. (Accessed Jan. 26, 2012).
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012.
Ceriello A, Motz E. Is oxidative stress the pathogenic mechanism underlying insulin resistance, diabetes, and cardiovascular disease? The common soil hypothesis revisited. Arterioscler. Thromb. Vasc. Biol. 2004;24(5):816-823.
Chait A, Brazg RL, Tribble DL, Krauss RM. Susceptibility of small, dense, low-density lipoproteins to oxidative modification in subjects with the atherogenic lipoprotein phenotype, pattern B. Am. J. Med. 1993;94(4):350-356.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan et al., Factorial Study of the Effects of Atorvastatin and Fish Oil on Dyslipidaemia in Visceral Obesity, 32 Euro. J. Clinical Investigation. 429 (2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J., 31:149-164 (2010).
Chatterjee SN, Agarwal S. Liposomes as membrane model for study of lipid peroxidation. Free Radic. Biol. Med. 1988;4(1):51-72.
Chemical Book, Eicosapentaenoic acid ethyl ester, copyright 2010, printed Jun. 16, 2011 from www.chemicalbook.com. (2010).
Chen, H., et al., "Eicosapentanoic acid inhibits hypoxia-reoxygenation-induced injury by attenuating upregulation of MMP-1 in adult rat myocytes." Cardiovascular Research 59:7-13 (2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (2003).
Chen, I.S., et al., "In vitro clearance of chylomicron triglycerides containing (?-3) eicosapentaenoate." Atherosclerosis, 65:193-198 (1987).
Cheng et al., "Antagonism of the prostaglandin D2 receptor 1 suppresses nicotinic acid-induces vasodilation in mice and humans," PNAS 103(17):6682-7 (2006).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, (1990).
Christensen, J. H., et al., "Effect of fish oil on heart rate variability in survivors of myocardial infarction: a double blind randomised controlled trial." BMJ, 312:677-678 (1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (1995).

(56) References Cited

OTHER PUBLICATIONS

Classification of Hyperlipidaemias and Hyperlipoproteinaemias, Bulletin of the World Health Organization, 43(6): 891-915 (1970).
Cleland, L.G., et al., "A Biomarker of n-3 compliance in patients taking fish oil for rheumatoid arthritis." Lipids 38:419-424 (2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501>.
Cohen AW, Combs TP, Scherer PE, Lisanti MP. Role of caveolin and caveolae in insulin signaling and diabetes. American journal of physiology. Endocrinology and metabolism. 2003;285(6):E1151-1160.
Cohen, J.D., et al., "30-year trends in serum lipids among United States adults: results from the National Health and Nutrition Examination Surveys II, III, and 1999-2006." Am J Cardiol., 106:969-975. (2010).
Cole et al., "Challenges and opportunities in the encapsulation of liquid and semi-solid formulations into capsules for oral administration," Advanced Drug Delivery Reviews, vol. 60, No. 6, pp. 747-756. (2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (2008).
Committee Roster for the Oct. 16, 2013 Meeting of the Endocrinologic and Metabolic Drugs Advisory Committee, 2 pages. (2013).
Conklin, S. M., et al., "Serum ?-3 fatty acids are associated with variation in mood, personality and behavior in hypercholesterolemic community volunteers." Psychiatry Research 152: 1-10 (2007).
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (2000).
Conquer, J.A., et al., "Effect of supplementation with different doses of DHA on the levels of circulating DHA as non-esterified fatty acid in subjects of Asian Indian background. J Lipid Res." 39:286-292. (1998).
Conquer, J.A., et al., "Supplementation with an algae source of docosahexaenoic acid increases (n-3) fatty acid status and alters selected risk factors for heart disease in vegetarian subjects." J Nutr., 126: 3032-3039. (1996).
Contacos et al. Effect of pravastatin and omega-3 fatty acids on plasma lipids and lipoproteins in patients with combined hyperlipidemia, pp. 1755-1762 (1993).
Coumadin [package insert], Princeton, NJ: Bristol-Myers Squibb; 2011.
Cox PJ, Ryan DA, Hollis FJ, et al. Absorption, disposition, and metabolism of rosiglitazone, a potent thiazolidinedione insulin sensitizer, in humans. Drug Metab. Dispos. 2000;28:772-780.
Creager MA, Gallagher SJ, Girerd XJ, Coleman SM, Dzau VJ, Cooke JP. L-arginine improves endothelium-dependent vasodilation in hypercholesterolemic humans. J. Clin. Invest. 1992;90:1248-1253.
Criqui, M., "Triglycerides and Coronary Heart Disease Revisited (Again)," vol. 147 No. 6, pp. 425-427 (2007).
Crowe, F. L., et al., "Serum phospholipid n-3 long-chain polyunsaturated fatty acids and physical and mental health in a population-based survey of New Zealand adolescents and adults." Am J Clin Nutr 86:1278-85 (2007).
Cruz et al., "The metabolic syndrome in children and adolescents," Curr. Diab. Rep., vol. 4(1):53-62 (2004).

Culhane et al., "Rosuvastatin for the treatment of hypercholesterolemia," Pharmacotherapy, 25(7):990-1000 (2005).
Daggy, B. et al. Dietary fish oil decreases VLDL production rates. Biochimica et Biophysics Acta 920: 293-300 (1987).
Dall et al., "Clinical utility of low-density lipoprotein particle measurement in management of cardiovascular disease: a case report," Research Reports in Clin. Cardiol., vol. 2, pp. 57-62 (2011).
Das, U.N., Essential fatty acids as possible mediators of the actions of statins. Prostaglandins, Leukotrienes and Essential FattyAcids 65(1):37-40, (2001).
Davidson MH, Ballantyne CM, Jacobson TA, et al. Clinical utility of inflammatory markers and advanced lipoprotein testing: advice from an expert panel of lipid specialists. J. Clin. Lipidol. 2011;5:338-367.
Davidson MH, et al., Effects of prescription omega-3-acid ethyl esters on lipo protein particle concentrations, apolipoproteins AI and CIII, and lipoprotein-associated phospholipase $A_2$ mass in statin-treated subjects with hypertrigylceridemia, J.Clin. Lipid., vol. 3(5), pp. 332-340 (2009).
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. 2014;34:1298-1306.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (2007).
Davidson MH., "Mechanisms for the hypotriglyceridemic effect of marine omega 3 fatty acids." Am J Cardiol 98(4A):27i-33i. (2006).
Davidson, M.H., et al., "Effects of docosahexaenoic acid on serum lipoproteins in patients with combined hyperlipidemia: a randomized, doubleblind, placebo-controlled trial." J Am Coll Nutr., 16:236-243. (1997).
De Caterina, R, et al., "Control of Endothelial Leukocyte Adhesion Molecules by Fatty Acids." Lipids, vol. 31:S57-S63 (1996).
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).
De Graaf J, Hak-Lemmers HL, Hectors MP, Demacker PN, Hendriks JC, Stalenhoef AF. Enhanced V susceptibility to in vitro oxidation of the dense low density lipoprotein subfraction in healthy subjects. Arterioscler. Thromb. 1991;11(2):298-306.
Deckelbaum R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).
Defendants' Invalidity Contentions, 3:14-CV-02550-MLC-DEA (D.N.J.), 520 pages (Dec. 5, 2014).
Defendants' Joint Invalidity Contentions, 3:14-CV-02550-MLC-TJB (D.N.J.), 901 pages (Dec. 5, 2014).
Dewailly, E. et al., "n-3 Fatty acids and cardiovascular disease risk factors among the Inuit of Nunavik." Am J Clin Nutr 74:464-73 (2001).
Di Spirito, M., Morelli, G., Doyle, R.T., Johnson, J. & McKenney, J. Effect of omega-3-acid ethyl esters on steady-state plasma pharmacokinetics of atorvastatin in healthy adults. Expert Opin. Pharmacother. 9, 2939-2945 (2008).
Diagnostic and Statistical Manual of Mental Disorders, 4.Ed. Text revision, published by the American Psychiatric Assoc., pp. 154-163 and 369-381 (2000).
Diagnostic and Statistical Manual of Mental Disorders, 4.sup.th Ed., published by the American Psychiatric Assoc., pp. 285-286, (1994).
Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (1996).

(56) References Cited

OTHER PUBLICATIONS

Dijk, J. M., et al., "Carotid intima-media thickness and the risk of new vascular events in patients with manifest atherosclerotic disease: the SMART study." European Heart Journal 27:1971-1978 (2006).
Din et al., "Omega 3 fatty acids and cardiovascular disease—fishing for a natural treatment," BMJ, vol. 327, No. 7430, pp. 30-35 (2004).
Dodin, S., et al., "Flaxseed on cardiovascular disease markers in healthy menopausal women: a randomized, double-blind, placebo-controlled trial." Nutrition 24:23-30 (2008).
Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, (1991).
Draft Agenda for the Oct. 16, 2013 Meeting of the Endocrinologic and Metabolic Drugs Advisory Committee, 2 pages.
Draft Meeting Roster for the Oct. 16, 2013 Meeting of the Endocrinologic and Metabolic Drugs Advisory Committee, 2 pages.
Draft Questions for the Oct. 16, 2013 Meeting of the Endocrinologic and Metabolic Drugs Advisory Committee, 1 page.
Drexler H, Zeiher AM, Meinzer K, Just H. Correction of endothelial dysfunction in coronary microcirculation of hypercholesterolaemic patients by !-arginine. Lancet. 1991;338:1546-1550.
Dullenmeijer, C., et al., "n-3 Fatty acid proportions in plasma and cognitive performance in older adults." Am J Clin Nutr 86:1479-85 (2007).
Duncan, R. E., et al., "Regulation of HMG-CoA reductase in MCF-7 cells by genistein, EPA, and DHA, alone and in combination with mevastatin." Cancer Letters 224:221-228 (2005).
Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001).
Dwyer, J. H., et al., "Arachidonate 5-Lipoxygenase Promoter Genotype, Dietary Arachidonic Acid, and Atherosclerosis." N. Engl. J. Med., 350:1 (2004).
Dyerberg, J., et al., "Marine Oils and Thrombogenesis." Prog. Lipid Res. 21:255-269 (1982).
Egert, S., et al., "Dietary alpha-linolenic acid, EPA, and DHA have differential effects on LDL fatty acid composition but similar effects on serum lipid profiles in normolipidemic humans." J Nutr., 139:861-868 (2009).
Ehara S, Ueda M, Naruko T, Haze K, Itoh A, Otsuka M, Komatsu R, Matsuo T, Itabe H, Takano T, Tsukamoto Y, Yoshiyama M, Takeuchi K, Yoshikawa J, Becker AE. Elevated levels of oxidized low density lipoprotein show a positive relationship with the severity of acute coronary syndromes. Circulation. 2001;103(15):1955-1960.
Eisenberg S, Bilheimer DW, Levy RI, Lindgren FT. "On the metabolic conversion of human plasma very low density lipoprotein to low density lipoprotein," Biochim Biophys Acta, 326:361-77 (1973).
Eisenberg S, Rachmilewitz D. "Metabolism of rat plasma very low density lipoprotein. I. Fate in circulation of the whole lipoprotein," Biochim Biophys Acta, 326:378-90 (1973).
Ei-Serag HB, Graham DY, Satia JA, et al. Obesity is an independent risk factor for GERD symptoms and erosive esophagitis. Am. J. Gastroenterol. Jun. 2005 100 (6): 1243-50.
Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000).
El-Saadani M, Esterbauer H, El-Sayed M, Gober M, Nassar AY, Jurgens G. A spectrophotometric assay for lipid peroxides in serum lipoproteins using commercially available reagent. J. Lipid Res. 1989;30:627-630.
El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).
Emsley et al., "Randomized, Placebo-Controlled Study of Ethyl-Eicosapentaenoic Acid as Supplemental Treatment in Schizophrenia," Am. J. Psychiatry, 159:1596-1598 (2002).
Engler, et al., "Docosahexaenoic acid restores endothelial function in children with hyperlipidemia: results from the EARLY Study." International Journal of Clinical Pharmacology and Therapeutics, vol. 42—No. 12—2004 (672-679). (2004).
Engler, M.B., et al., "Mechanisms of vasorelaxation induced by eicosapentaenoic acid (20:5n-3) in WKY rat aorta." British Journal of Pharmacology 131:1793-1799 (2000).
Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).
Ennis JL, Cromwell WC. Clinical utility of low-density lipoprotein particles and apolipoprotein B in patients with cardiovascular risk. J. Fam. Pract. 2013;62:1-8.
Epadel—PubChem CID 9831415, Retrieved on Apr. 9, 2014 [Retrieved from the Internet] <URL:http://pubchem.ncbi.nlm.nih.gov/compound/9831415>.
Epadel 1990 and JELIS Study.
Epadel Capsules 300, Japan Pharmaceutical Reference 369-371 (2nd ed.) (1991).
Epadel drug information brochure (2000), certified English translation.
Epadel Package Insert 2007 (with Translation).
Epadel® [Complete prescribing information]. Update (Version 5). Tokyo, Japan: Mochida Pharmaceutical; Jan. 2007. (English translation).
Eritsland J, Arnesen H, Gronseth K, et al. Effect of dietary supplementation with n-3 fatty acids on coronary artery bypass graft patency. Am. J. Cardiol. Jan. 1996 77 (1): 31-6.
Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 1995 6 (1): 17-22.
Errata to the FDA Briefing Document Endocrinologic and Metabolic Drug Advisory Committee Meeting Oct. 16, 2013, 1 page.
Esposito, "Effect of a Mediterranean-Style Diet on Endothelial Dysfunction and Markers of Vascular Inflammation in the Metabolic Syndrome: A Randomized Trial", Journal of the American Medical Association, 2004, 292(12), 1440-1446.
Exhibit A to Defendants' Joint Invalidity Contentions, 3:14-CV-02550-MLC-TJB (D.N.J.), 48 pages (Dec. 5, 2014).
Exhibit B to Defendants' Joint Invalidity Contentions, 3:14-CV-02550-MLC-TJB (D.N.J.), 6 pages (Dec. 5, 2014).
Exhibit C to Defendants' Joint Invalidity Contentions, 3:14-CV-02550-MLC-TJB (D.N.J.), 14 pages (Dec. 5, 2014).
Exhibit D to Defendants' Joint Invalidity Contentions, 3:14-CV-02550-MLC-TJB (D.N.J.), 19 pages (Dec. 5, 2014).
Exhibit E to Defendants' Joint Invalidity Contentions, 3:14-CV-02550-MLC-TJB (D.N.J.), 6 pages (Dec. 5, 2014).
Exhibit F to Defendants' Joint Invalidity Contentions, 3:14-CV-02550-MLC-TJB (D.N.J.), 10 pages (Dec. 5, 2014).
Exhibit G to Defendants' Joint Invalidity Contentions, 3:14-CV-02550-MLC-TJB (D.N.J.), 21 pages (Dec. 5, 2014).
Exhibit H to Defendants' Joint Invalidity Contentions, 3:14-CV-02550-MLC-TJB (D.N.J.), 10 pages (Dec. 5, 2014).
Exhibit I to Defendants' Joint Invalidity Contentions, 3:14-CV-02550-MLC-TJB (D.N.J.), 14 pages (Dec. 5, 2014).
Exhibit J to Defendants' Joint Invalidity Contentions, 3:14-CV-02550-MLC-TJB (D.N.J.), 13 pages (Dec. 5, 2014).
Exhibit K to Defendants' Joint Invalidity Contentions, 3:14-CV-02550-MLC-TJB (D.N.J.), 5 pages (Dec. 5, 2014).
Exhibit L to Defendants' Joint Invalidity Contentions, 3:14-CV-02550-MLC-TJB (D.N.J.), 5 pages (Dec. 5, 2014).
Exhibit M to Defendants' Joint Invalidity Contentions, 3:14-CV-02550-MLC-TJB (D.N.J.), 7 pages (Dec. 5, 2014).
Exhibit N to Defendants' Joint Invalidity Contentions, 3:14-CV-02550-MLC-TJB (D.N.J.), 15 pages (Dec. 5, 2014).
Exhibit O to Defendants' Joint Invalidity Contentions, 3:14-CV-02550-MLC-TJB (D.N.J.), 6 pages (Dec. 5, 2014).

(56) References Cited

OTHER PUBLICATIONS

Exhibit P to Defendants' Joint Invalidity Contentions, 3:14-CV-02550-MLC-TJB (D.N.J.), 17 pages (Dec. 5, 2014).
Exhibit Q to Defendants' Joint Invalidity Contentions, 3:14-CV-02550-MLC-TJB (D.N.J.), 64 pages (Dec. 5, 2014).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
FDA Briefing Document, Endocrinologic and Metaboloic Drugs Advisory Committee Meeting, dated Oct. 16, 2013, available publicly at least as of Oct. 16, 2013, 115 pages.
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Feron O, Dessy C, Desager JP, Balligand JL. Hydroxy-methylglutaryl-coenzyme a reductase inhibition promotes endothelial nitric oxide synthase activation through a decrease in caveolin abundance. Circulation. 2001;103:113-118.
Final Agenda for the Oct. 16, 2013 Meeting of the Endocrinologic and Metabolic Drugs Advisory Committee, 2 pages.
Final Meeting Roster for the Oct. 16, 2013 Meeting of the Endocrinologic and Metabolic Drugs Advisory Committee, 2 pages.
Final Questions for the Oct. 16, 2013 Meeting of the Endocrinologic and Metabolic Drugs Advisory Committee, 1 page.
Finnen et al., "Purification and characterisation of phospholipase A2 from human epidermis,", Biochemical Society Trans,19(2):91S, 1991.
Fischer, R., et al., "Dietary n-3 polyunsaturated fatty acids and direct renin inhibition improve electrical remodeling in a model of high human renin hypertension." Hypertension 51:540-546 (2008).
Fisher et al., Journal of Biological Chemistry (2001) 276(3) 27855-27863.
Flaten, H., et al., "Fish-oil concentrate: effects on variables related to cardiovascular disease." Am. J. Clin. Nutr. 52:300-306 (1990).
Ford, E.S. et al., "Hypertriglyceridemia and Its Pharmacologic Treatment Among US Adults." Arch, Intern. Med., 169(6): 572-78 (2009).
Frangou et al., "Efficacy of ethyl-eicosapentaenoic acid in bipolar depression: randomised double-blind placebo-controlled study," British Journ. Psychiatry, 188, 46-50 (2006).
Frey R, Muck W, Kirschbaum N, et al. Riociguat (BAY 63-2521) and warfarin: a pharmacodynamic and pharmacokinetic interaction study. J. Clin. Pharmacol. Jul. 2011 51 (7): 1051-60.
Frick, MH, et al., "Helsinki Heart Study. Primary prevention trial with gemfibrozil in middle-aged men with dyslipidaemia. Safety of treatment, changes in risk factors and incidence of coronary heart disease", N. Eng. J. Med., 317:1237-1245, (1987).
Friedewald, W.T., et al., "Estimation of the concentration of low-density lipoprotein cholesterol in plasma, without use of the preparative ultracentrifuge." Clin Chem.,18:499-502 (1972).
Friedman, A. N., et al., "Fish Consumption and Omega-3 Fatty Acid Status and Determinants in Long-Term Hemodialysis." Amer. J. Kidney Diseases, 47(6):1064-1071 (2006).
Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996).
Frøyland, L., et al., "Hypotriacylglycerolemic component of fish oil." Prostaglandins, Leukotrienes and Essential Fatty Acids 57 (4 & 5):387-388 (1997).
Furuta T, Shirai N, Sugimoto M, et al. Influence of CYP2C19 pharmacogenetic polymorphism on proton pump inhibitor-based therapies. Drug Metab. Pharmacokinet Jun. 2005 20 (3): 153-67.
Galeano NF, Al-Haideri M, Keyserman F, Rumsey SC, Deckelbaum RJ. Small dense low density lipoprotein has increased affinity for LDL receptor-independent cell surface binding sites: a potential mechanism for increased atherogenicity. J. Lipid Res. 1998;39(6):1263-1273.
Gallagher et al., "Germline BRCA Mutations Denote a Clinicopathalogic Subset of Prostate Cancer," Amer. Assoc. Cancer Res. Clin Cancer Res., 16(7):2115-21 (2010).
Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48.
Gardner CD, Fortmann SP, Krauss RM. Association of small low-density lipoprotein particles with the incidence of coronary artery disease in men and women. JAMA. 1996;276(11):875-881.
Garg, R., et al., "Niacin treatment increases plasma homocyst(e)ine levels", Am. Heart. J., 138:1082-1087, (1999).
Garnett, "Interactions with Hydroxymethylglutaryl-coenzyme A reductase inhibitors," Am J Health-Sys Pharm vol. 52, 1639-1645, (1995).
Genest, JJ, et al., "Familial lipoprotein disorders in patients with premature coronary artery disease", 85:2025-2033, (1992).
Geppert, et al. "Microalgal docosahexaenoic acid decreases plasma triacylglycerol in normolipidaemic vegetarians: a randomized trial." British Journal of Nutrition, 95, 779-786. (2006).
Gillies, et al."Effect of a Novel Eicosapentaenoic Acid-Rich Oil on Serum Cholesterol in Man," DuPont 2010.
Ginsberg HN, Elam MB, Lovato LC, Crouse JR, 3rd, Leiter LA, Linz P, Friedewald WT, Buse JB, Gerstein HC, Probstfield J, Grimm RH, Ismail-Beigi F, Bigger JT, Goff DC, Jr., Cushman WC, Simons-Morton DG, Byington RP. Effects of combination lipid therapy in type 2 diabetes mellitus. N. Engl. J. Med. 2010;362:1563-1574.
Ginsberg HN. "Hypertriglyceridemia: new insights and new approaches to pharmacologic therapy," Am J Cardiol, 87:1174-1180 (2001).
Girotti A W. Lipid hydroperoxide generation, turnover, and effector action in biological systems. J. Lipid Res. 1998;39(8):1529-1542.
GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, (Aug. 7, 1999).
Glod, "Recent Advances in the Pharmacotherapy of Major Depression", Arch. Psychiatr. Nurs., 10(6):355-364, Abstract (Dec. 1996).
Goldberg, A C: "Combination therapy of dyslipidemia," Current Treatment Options in Cardiovascular Medicine Aug. 2007 GB, vol. 9, No. 4, pp. 249-258 (2007).
Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001).
Gordon, DJ. et al., High density lipoprotein cholesterol and cardiovascular disease: four prospective American studies. Circulation. 79: 8-15. (1989).
Gorriz JL et al., "Rhabdomyolysis and Acute Renal Failure Associated with Gemfibrozil Therapy," Nephron 74(2): 437-438 (1996).
Gorriz, JL, "Rhabdomyolysis and Acute Renal Failure Associated with Bezafibrate Treatment," Nephrol Dial Transplant 10(12):2371-2372 (1995).
Gosai, P. et al. Effect of omega-3-acid ethyl esters on the steady-state plasma pharmacokinetics of rosuvastatin in healthy adults. Expert Opin. Pharmacother. 9, 2947-2953 (2008).
Goto, Y. et al "Clinical Pharmacological Trial of Ethyl Icosapentate (MND-21)—Dose Finding Study." Journal of Clinical Therapeutic & Medicines 8:1293-309 (1992).
Gould, A.L., et al., "Cholesterol reduction yields clinical benefit: impact of statin trials." Circulation, 97:946-952 (1998).
Greenblatt DJ, von Moltke LL. Interaction of warfarin with drugs, natural substances, and foods. J. Clin. Pharmacol. Feb. 2005 45 (2): 127-32.
Grenyer, Brin F.S., et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007).
Griffin, M.D., et al., "Effects of altering the ratio of dietary n-6 to n-3 fatty acids on insulin sensitivity, lipoprotein size, and postpran-

(56) References Cited

OTHER PUBLICATIONS dial lipemia in men and postmenopausal women aged 45-70 y: the OPTILIP Study." Am J Clin Nutr 84:1290-8 (2006).

Grimsgaard et al., "Effects of Highly Purified Eicosapentaenoic Acid and Docosahexaenoic Acid on Hemodynamics in Humans" American Society for Clinical Nutrition, 68:52-9, (1998).

Grimsgaard, Kaare H. Bonaa, John-Bjarne Hansen, and Arne Nordoy, "Highly purified eicosapentaenoic acid and docosahexaenoic acid in humans have similar triacylglycerol-lowering effects but divergent effects on serum fatty acids" Am J Clin Nutr, 66:649-59, (1997).

Grundy S.M et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002).

Grundy SM, et al. Implications of Recent Clinical Trials for the National Cholesterol Education Prgram Adult Treatment Panel III Guidelines, Circulation. 2004; 110:227-39.

Grundy, Scott M., "Low-Density Lipoprotein, Non-High-Density Lipoprotein, and Apolipoprotein B as Targets of Lipid-Lowering Therapy" Circulation 106:2526-2529 (2002).

Guallar, E., et al., "Omega-3 fatty acids in adipose tissue and risk of myocardial infarction—The EURAMIC study." Arterioscler. Thromb. Vasc. Biol., 19:1111-1118 (1999).

Guillot, et al., "Increasing intakes of the long-chain ?-3 docosahexaenoic acid: effects on platelet functions and redox status in healthy men," The FASEV Journal, vol. 23, pp. 2909-2916 (2009).

Guizy, M., et al., "ω-3 and ω-6 Polyunsaturated fatty acids block HERG channels." Am J Physiol Cell Physiol 289:C1251-C1260 (2005).

Gyarmathy, M., "Selection from the industrial manufacturing. 5th part: Gelatine capsules. 5/2 part: Soft gelatine capsules," Gyogyszereszet, vol. 38, No. 2, pp. 105-109 (1994).

Hall, W. L., et al., "A high-fat meal enriched with eicosapentaenoic acid reduces postprandial arterial stiffness measured by digital volume pulse analysis in healthy men." J. Nutr. 138: 287-291 (2008).

Hamazaki et al., "Docosahexaenoic Acid-Rich Fish Oil Does Not Affect Serum Lipid Concentrations of Normolipidemic Young Adults", American Institute of Nutrition, 126(11):2784-2789, Nov. 1996.

Hamazaki et al., "Effects of Orally Administered Ethyl Ester of Eicosapentaenoic Acid (EPA: C20:5, omega-3) on PG12-Like Substance Production by Rat Aorta" Prostaglandins, vol. 23 No. 4, pp. 557-567 (1982).

Hamazaki T. et al., "Reduction of microalbuminuria in diabetics by Eicosapentaenoic acid ethyl ester" Lipids. 25 (9):542-5 (1990).

Hampel H, Abraham NS, El-Se rag HB. Meta-analysis: obesity and the risk for gastroesophageal reflux disease and its complications. Ann. Intern. Med. Aug. 2005 143 (3): 199-211.

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011).

Hannah, J., et al., "Effect of dietary fatty acids on LDL binding." Ann N Y Acad Sci., 683:178-182 (1993).

Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993).

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harkonarson, H., et al., "Effects of a 5-lipoxygenase-activating protein inhibitor on biomarkers associated with risk of myocardial infarction—a randomized trial." JAMA, 293(8):2245-56 (2005).

Harris "n-3 Fatty acids and lipoproteins: a comparison of results from human and animal studies," Lipids 31, 243-252 (1996).

Harris, W. S. et al. "Safety and efficacy of Omacor in severe hypertriglyceridemia," Journal of Cardiovascular Risk, 4:385-391 (1997).

Harris, W. S. "Fish oils and plasma lipid and lipoprotein metabolism in humans: a critical review." J Lipid Res. 30:785-807 (1989).

Harris, W. S., "The omega-3 index as a risk factor for coronary heart disease." Am J Clin Nutr 87:1997S-2002S (2008).

Harris, W. S., et al., "n-3 Fatty acids and urinary excretion of nitric oxide metabolites in humans." Am. J. Clin. Nutr., 65:459-64 (1997).

Harris, W. S. et al "Influence of n-3 fatty acid supplementation on the endogenous activities of plasma lipases." Am. J. Clin. Nutr. 66:254-60 (1997).

Harris, W.S., "Expert opinion: omega-3 fatty acids and bleeding—cause for concern?" The American Journal of Cardiology 99(6A): 45C-46C (2007).

Harris, W.S., "n-3 Fatty acids and human lipoprotein metabolism: an update." Lipids 34:S257-S258 (1999).

Harris, W.S., "n-3 Fatty acids and serum lipoproteins: human studies." Am J Clin Nutr 65:1645S-54S (1997).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

Harris, W.S., et al., "Omega-3 fatty acids and coronary heart disease risk: Clinical and mechanistic perspectives." Atherosclerosis 197:12-24 (2008).

Harris, W.S., et al., "Stearidonic acid increases the red blood cell and heart eicosapentaenoic acid content in dogs." Lipids 42:325-333 (2007).

Harris, W.S., et al., "Tissue n-3 and n-6 fatty acids and risk for coronary heart disease events." Atherosclerosis 193:1-10 (2007).

Hartweg, J., et al., "Potential impact of omega-3 treatment on cardiovascular disease in type 2 diabetes." Curr Opin Lipidol., 20:30-38 (2009).

Hata et al, Geriatric Medicine, 30 (5), 799-852, 1992 (with English translation).

Hawthorne, et al., "High dose eicosapentaenoic acid ethyl ester: effects on lipids and neutrophil leukotriene production in normal volunteers." Br. J. Clin. Pharmac., vol. 30, 187-194 (1990).

Hayashi et al., Decreases in Plasma Lipid Content and Thrombotic Activity by Ethyl Icosapentate Purified from Fish Oiles, Current Therapeutic Research, vol. 56, No. 1, pp. 24-31 (1995).

Herbette L, Marquardt J, Scarpa A, Blasie JK. A direct analysis of lamellar x-ray diffraction from hydrated oriented multilayers of fully functional sarcoplasmic reticulum. Biophys. J. 1977;20(2):245-272.

Hibbeln, J. R., et al., "Healthy intakes of n-3 and n-6 fatty acids: estimations considering worldwide diversity." Am J Clin Nutr. 83:1483S-93S (2006).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (2002).

(56) References Cited

OTHER PUBLICATIONS

Hirai, A., et al., "The effects of the oral administration of fish oil concentrate on the release and the metabolism of [14C] arachidonic acid and [14C] eicosapentaenoic acid by human platelets", Thromb. Res., 28:285-298, (1982).
Hirano T, Ito Y, Koba S, Toyoda M, Ikejiri A, Saegusa H, Yamazaki J, Yoshino G. Clinical significance of small dense low-density lipoprotein cholesterol levels determined by the simple precipitation method. Arterioscler. Thromb. Vasc. Biol. 2004;24(3):558-563.
Hirano, R., et al., "Regulation by long-chain fatty acids of the expression of cholesteryl ester transfer protein in HepG2 cells." Lipids, 36:401-406 (2001).
Hofacer R, et al., Omega-3 fatty acid deficiency increases stearoyl-CoA desaturase expression and activity indices in rat liver: Positive association with non-fasting plasma triglyceride levels, Prostaglandins Leukot. Essent. Fatty Acids. 2012;86:71-7.
Hohenester, "Primary Biliary Cirrhosis," Semin Immunopathol. 31L:283-307, 285 (2009).
Holmeide, A. K., et al., "Oxidative degradation of eicosapentaenoic acid into polyunsaturated aldehydes." Tetrahedron 59:7157-7162 (2003).
Holub, B.J., PhD, "Fish Oils and Cardiovascular Disease", Canadian Medical Association Journal, 141(10):1063 (1989).
Holvoet P, Kritchevsky SB, Tracy RP, Mertens A, Rubin SM, Butler J, Goodpaster B, Harris TB. The metabolic syndrome, circulating oxidized LDL, and risk of myocardial infarction in wellfunctioning elderly people in the health, aging, and body composition cohort. Diabetes. 2004;53(4):1068-1073.
Hombeck, M., et al., "Biosynthesis of the algal pheromone fucoserratene by the freshwater diatom Asterionella formosa (Bacillariophyceae)." Tetrahedron 54:11033-11042 (1998).
Horrobin, D.F. The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).
Hoskins et al., "Combination use of statins and omega-3 fatty acids: an emerging therapy for combined hyperlipidemia," Abstract, 1(5): 579-591(13) (2006).
Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).
HPs2-thrive Collaborative Group, "Randomized placebo-controlled trial in 25 673 high-risk patients of er niacin/laroprant: Trial design, pre-specified muscle and liver outcomes, and reasons for stopping study treatment." Eur. Heart J. 2013;34:1279-1291.
Hruska MW, Amico JA, Langaee TY, Ferrell RE, Fitzgerald SM, Frye RF. The effect of trimethoprim on CYP2C8 mediated rosiglitazone metabolism in human liver microsomes and healthy subjects. Br. J. Clin. Pharmacol. 2005;59:70-79.
Hughes et al., "Fish oil produces an atherogenic lipid profile in hypertensive men," Atherosclerosis, 84, pp. 229-237 (1990).
Hulthe J, Hulten LM, Fagerberg B. Low adipocyte-derived plasma protein adiponectin CJ concentrations are associated with the metabolic syndrome and small dense low-density lipoprotein particles: atherosclerosis and insulin resistance study. Metab. Clin. Exp. 2003;52(12):1612-1614.
Huntington's Diesase Drug Works—The DHA Dilemma http://hddrugworks.org/index2.php?option=com_content&task=view&id=185&pop=1&pa . . . Printed on Aug. 22, 2008.
Ignarro LJ, Buga GM, Wood KS, Byrnes RE, Chaudhuri G. Endothelium-derived relaxing factor produced and released from artery and vein is nitric oxide. Proc. Natl. Acad. Sci. USA. 1987;84:9265-9269.
Illingworth, DR, et al., "Comparative effects of lovastatin and niacin in primary hypercholesterolemia: A prospective trial", Arch. Int. Med., 154:1586-1595, (1994).

Inoue, I., et al., "Expression of peroxisome proliferator-activated receptor ? (PPAR?) in primary cultures of human vascular endothelial cells." Biochem. Biophys. Res. Comm., 246, 370-374 (1998).
Ishida, Y., et al., "?-Lipoic Acid and Insulin Autoimmune Syndrome." Diabeters Care, 30(9): 2240-41 (2007).
Isley, et al., "Pilot study of combined therapy with w-3 fatty acids and niacin in atherogenic dyslipidemia," Journal of Clinical Lipidology, 1, 211-217 (2007).
Itoh et al., "Increased adinponectin secretion by highly purified eicosapentaenoic acid in rodent models of obesity and human obses subjects," Arterioscler. Thromb. Vasc. Biol., pp. 1918-1925 (together with online Supplements 1-15) (2007).
Jacob RF, Mason RP. Lipid peroxidation induces cholesterol domain formation in model membranes. J. Biol. Chem. 2005;280(47):39380-39387.
Jacob RF, Walter MF, Self-Medlin Y, Mason RP. Atorvastatin active metabolite inhibits oxidative modification of small dense low-density lipoprotein. J. Cardiovasc. Pharmacol. 2013;62(2):160-166.
Jacobson et al. "Hypertriglyceridemia and Cardiovascular Risk Reduction", Clinical Therapeutics, vol. 29 pp. 763-777 (2007).
Jacobson TA. Opening a new lipid "apo-thecary": incorporating apolipoproteins as potential risk factors and treatment targets to reduce cardiovascular risk. Mayo Clin. Proc. 2011;86:762-780.
Jacobson, T. Secondary Prevention of Coronary Artery Disease with Omega-3 Fatty Acids. Am J Cardiol; 98 [suppl]: 61i-70i (2006).
Jacobson, T.A., "Role of n-3 fatty acids in the treatment of hypertriglyceridemia and cardiovascular disease." Am J Clin Nutr 87:1981S-90S (2008).
Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).
Jakus V, Rietbrock N. Advanced glycation end-products and the progress of diabetic vascular complications. Physiol. Res. 2004;53(2): 131-142.
Jenner, "Presymptomatic Detection of Parkinson's Disease". J Neural Transm Suppl., 40:23-36. (Abstract only) (1993).
Jialal I, Devaraj S. Antioxidants and atherosclerosis: Don't throw out the baby with the bath water. Circulation. 2003;107:926-928.
Jialal, I., "Editorial: Remnant lipoproteins: measurement and clinical significance." Clinical Chemistry 48(2):217-219 (2002).
Journal of Practical Pharmacy, 58(4):1303-1324 (2007).
Journal of the Japanese Diabetes Society, Mar. 30, 2008, 51(3), pp. 233-237.
Jung, U.J., et al., "n-3 Fatty acids and cardiovascular disease: mechanisms underlying beneficial effects." Am J Clin Nutr 87: 2003S-9S (2008).
Kaminski WE, Jendraschak E, Kiefl R, et al. Dietary omega-3 fatty acids lower levels of platelet-derived growth factor mRNA in human mononuclear cells. Blood Apr. 1993 81 (7): 1871-9.
Kanayasu, T., et al., "Eicosapentaenoic acid inhibits tube formation of vascular endothelial cells in vitro." Lipids 26:271-276 (1991).
Kastelein et al., Omega-3 Free Fatty Acids for the Treatment of Severe Hypertriglyceridemia: The EpanoVa for Lowering Very High Triglycerides (EVOLVE).Trial, J. Clin. Lipidol. (JACL 597) 2013.
Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).
Katayama et al., "Efficacy and Safety fo Ethyl Icosapentate (Epadel) Given for a Long Term Against Hyperlipidemia," Prog. Med., 21:457-467, translated from Japanese (2001).
Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).
Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi, 72(1):18-24 (1983).

(56) References Cited

OTHER PUBLICATIONS

Kawano, H., et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid", J. Atheroscler. Thromb., 9:170-177, (2002).

Kawashima, H., et al., "Oral Administration of Dihomo-?-Linolenic Acid Prevents Development of Atopic Dermatitis in NC/Nga Mice." Lipids 43:37-43 (2008).

Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. 2005;366:1849-1861.

Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).

Kelley, et al., "Docosahexaenoic acid supplementation improves fasting and postprandial lip profiles in hypertriglyceridemic men." The American Journal of Clinical Nutrition, 86: 324-333 (2007).

Kellner-Weibel G, Yancey PG, Jerome WG, Walser T, Mason RP, Phillips MC, Rothblat GH. Crystallization of free cholesterol in model macrophage foam cells Arterioscler. Thromb. Vasc. Biol. 1999;19(8):1891-1898.

Kendall BJ, Macdonald GA, Hayward NK, et al. The risk of Barrett's esophagus associated with abdominal obesity in males and females. Int. J. Cancer May 2013 132 (9): 2192-9.

Kerr, S., Brosnan MJ, Mcintyre M, Reid JL, Dominiczak AF, Hamilton CA. Superoxide anion production is increased in a model of genetic hypertension role of the endothelium. Hypertension. 1999;33:1353-1358.

Kew, S., et al., "Effects of oils rich in eicosapentaenoic and docosahexaenoic acids on immune cell composition and function in healthy humans." Am J Clin Nutr 79:674-81 (2004).

Kim F, Tysseling KA, Rice J, Gallis B, Haji L, Giachelli CM, Raines EW, Corson MA, Schwartz MW. Activation of IKKbeta by glucose is necessary and sufficient to impair insulin signaling and nitric oxide production in endothelial cells. J. Mol. Cell. Cardiol. 2005;39(2):327-334.

Kim KA, Park PW, Kim HK, Ha JM, Park JY. Effect of quercetin on the pharmacokinetics of rosiglitazone, a CYP2C8 substrate, in healthy subjects. J. Clin. Pharmacol. 2005;45:941-946.

Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).

Kinoshita, "Anti-hyperlipidemic agents," Nihon Rinsho, 60(5):968-74 (2002) (Abstract Only).

Kinsella, J.E. et al., "Dietary n-3 polyunsaturated fatty acids and amelioration of cardiovascular disease: possible mechanisms." Am J Clin Nutr 52:1-28 (1990).

Knapp HR. Dietary fatty acids in human thrombosis and hemostasis. Am. J. Clin. Nutr. May 1997 65 (5 Suppl): 1687S-98S.

Knopp, R.H., et al., "Contrasting effects of unmodified and time-release forms of niacin on lipoproteins in hyperlipidemic subjects: clues to mechanism of action of niacin", Metabolism, 34:642-650, (1985).

Koba S, Hirano T, Ito Y, Tsunoda F, Yokota Y, Ban Y, Iso Y, Suzuki H, Katagiri T. Significance of small dense low-density lipoprotein-cholesterol concentrations in relation to the severity of coronary heart diseases. Atherosclerosis. 2006;189(1):206-214.

Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).

Kojda G, Harrison DG. Interactions between no and reactive oxygen species: Pathophysiological importance in atherosclerosis, hypertension, diabetes and heart failure. Cardiovasc. Res. 1999;43:562-571.

Kojima, T,. et al., "Long-term administration of highly purified eicosapentaenoic acid provides improvement of psoriasis." Dermatologica, 182:225-230 (1991).

Koroshetz, W.J. Huntington's Disease. In Samuels, M. (ed.) Office Practice of Neurology, pp. 654-661 (1996).

Kosonen, O., et al., "Inhibition by nitric oxide-releasing compounds of E-selectin expression in and neutrophil adhesion to human endothelial cells." European Journal of Pharmacology 394:149-156 (2000).

Krauss RM. Heterogeneity of plasma low-density lipoproteins and atherosclerosis risk. Curr. Opin. Lipidol. 1994;5(5):339-349.

Kris-Ehterton, P. M., et al., "Omega-3 Fatty Acids and Cardiovascular Disease—New Recommendations From the American Heart Association." Arterioscler Thromb Vasc Biol. 23:151-152 (2003).

Kris-Etherton, et al., "Fish Consumption, Fish Oil, Omega-3 Fatty Acids, and Cardiovascular Disease" Circulation, 106:2747-2757 (2002).

Krzynowek et al., "Purification of Omega-3 Fatty Acids from Fish Oils Using HPLC: An Overview," National Marine Fisheries—Proceedings of the first joint conference of the Tropical and Sub-tropical Fisheries Technological Soceity of the Americas with the Atlantic Fisheries Technological Society, pp. 74-77 (1988).

Ku, K., et al., "Beneficial Effects of to-3 Fatty Acid Treatment on the Recovery of Cardiac Function After Cold Storage of Hyperlipidemic Rats." Metabolism, 48(10):123-1209 (1999).

Kunimoto M, Inoue K, Nojima S. Effect of ferrous ion and ascorbate-induced lipid peroxidation on liposomal membranes. Biochem. Biophys.Acta. 1981;646(1):169-178.

Kurabayashi, T., et al., "Eicosapentaenoic acid effect on hyperlipidemia in menopausal Japanese women." Obstet Gynecol 96:521-8 (2000).

Lai, E. et al., "Suppression of niacin-induced vasodilation with an antagonist to prostaglandin D2 receptor subtype 1", Clin. Pharm. & Ther., 81:849-857, (2007).

Laidlaw, M., et al., "Effects of supplementation with fish oil-derived n-3 fatty acids and ?-linolenic acid on circulating plasma lipids and fatty acid profiles in women." Am J Clin Nutr 77:37-42 (2003).

Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. 2008;62(7): 1087-1095.

Lamharzi N, Renard CB, Kramer F, Pennathur S, Heinecke JW, Chait A, Bomfeldt KE. Hyperlipidemia in concert with hyperglycemia stimulates the proliferation of macrophages in atherosclerotic lesions: potential role of glucose-oxidized LDL. Diabetes. 2004;53(12):3217-3225.

Landmesser U, Dikalov S, Price SR, McCann L, Fukai T, Holland SM, Mitch WE, Harrison DG. Oxidation of tetrahydrobiopterin leads to uncoupling of endothelial cell nitric oxide synthase in hypertension. J. Clin. Invest. 2003;111:1201-1209.

Larsen, L.N., et al., "Heneicosapentaenoate (21:5n-3): Its incorporation into lipids and its effects on arachidonic acid and eicosanoid Synthesis." Lipids 32:707-714 (1997).

Laufs et al., "Upregulation of endothelial nitric oxide synthase by hmg coa reductase inhibitors," Circulation (1998) 97:1129-1135.

Law, M.R., et al., "Quantifying effect of statins on low density lipoprotein cholesterol, ischaemic heart disease, and stroke: systematic review and meta-analysis." Br Med J., 326:1423-1427 (2003).

Leaf, A., "Historical overview of n3 fatty acids and coronary heart disease." Am J Clin Nutr 87:1978S-80S. (2008).

Lee and G.Y.H. Lip, "The Role of Omega-3 Fatty Acids in the Secondary Prevention of Cardiovascular Disease", Q J Med, 96:465-480, (2003).

Lee C, Sigari F, Segrado T, Horkko S, Hama S, Subbaiah PV, Miwa M, Navab M, Witztum JL, Reaven PD. All ApoB-containing lipoproteins induce monocyte chemotaxis and adhesion when mini-

(56) References Cited

OTHER PUBLICATIONS mally modified. Modulation of lipoprotein bioactivity by platelet-activating factor acetylhydrolase. Arterioscler. Thromb. Vase. Biol. 1999; 19(6): 1437-1446.
Lee, J.H., et al., "Omega-3 fatty acids for cardioprotection." Mayo Clin Proc., 83(3):324-332 (2008).
Leigh-Firbank et al., "Eicosapentaenoic acid and docosahexanoic acid from fish oils: differential associations with lipid responses," Br. J. Nutr. 87:435-445 (2002).
Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).
Leonard, Brian E., "Neurological Aspects", Fundamentals of Psychopharmacology, 186-187, (1997).
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, (1999).
Li, D., et al., "Effect of dietary a-linolenic acid on thrombotic risk factors in vegetarian men." Am J Clin Nutr 69:872-82 (1999).
Li, H., et al "EPA and DHA reduce LPS-induced inflammation responses in HK-2 cells: Evidence for a PPAR-?-dependent mechanism." Kidney Int'l. 67:867-74 (2005).
Libby, "Inflammation and atherosclerosis," Nature (2002) 420(6917):868-874.
Lien, E.L., "Toxicology and safety of DHA." Prostaglandins Leukot Essent Fatty Acids., 81:125-132 (2009).
Lin, Pao-Yen, M.D., et al., "A Meta-Analytic Review of Double-Blind, Placebo-Controlled Trials of Antidepressant Efficacy of Omega-3 Fatty Acids", Psychiatry, 1056-1061 (Jul. 2007).
Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).
Lindsey, S., et al., "Low density lipoprotein from humans supplemented with n-3 fatty acids depresses both LDL receptor activity and LDLr mRNA abundance in HepG2 cells." J Lipid Res., 33:647-658 (1992).
Lipitor (Pfizer, 2007).
Lipitor [package insert]. New York, NY: Parke-Davis (2012).
Liu et al., "Effects of stable fish oil and simvastatin on plasma lipoproteinc in patients with hyperlipidemia," Nutrion Res. , vol. 23, pp. 1027-1034 (2003).
Liu X, et al., Stearoyl CoA Desaturase 1: Role in Cellular Inflammation and Stress, Adv. Nutr. 2011;2:15-22.
Lohmussaar, E., et al., "ALOX5AP Gene and the PDE4D Gene in a Central European Population of Stroke Patients." Stroke, 36:731-736 (2005).
Lovaza (omega-3-acid ethyl esters) Capsules, Prescribing information, 9 pages, GlaxoSmithKline (Nov. 2008).
Lovaza [package insert]. Research Triangle Park, NC: GlaxoSmithKline (2012).
Lovaza, (omega-3-acid ethyl esters) Capsules, Prescribing information Smith Kline Beechum (Jul. 2009).
Lovaza, GlaxoSmithKline, Lovaza Prescribing Invormation, Jun. 2008 [retrieved from the internet Jun. 6, 2012 <http://web/archive/org/web/20090206170311/http://us.gsk/com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.'
Lovaza® (omega-3-acid ethyl esters) Capsules, Prescribing information, 12 pgs., GlaxoSmithKline, (Dec. 2010).
Lovaza®, Physicians' Desk Reference 2699-2701 (62d ed., 2008).
Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (2004).

Lu, G., et al., "Omega-3 fatty acids alter lipoprotein subfraction distributions and the in vitro conversion of very low density lipoproteins to lowdensity lipoproteins." J Nutr Biochem., 10:151-158 (1999).
Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).
Luria, MH, "Effect of low-dose niacin on high-density lipoprotein cholesterol and total cholesterol/high density lipoprotein cholesterol ratio", Arch. Int. Med., 148:2493-2495, (1998).
Lvovich V, Scheeline A. Amperometric sensors for simultaneous superoxide and hydrogen peroxide detection. Anal. Chern. 1997;69:454-462.
Madhavi et al., "Effect of n-6 and n-3 fatty acids on the survival of vincristine sensitive and resistant human cervical carcinoma cells in vitro", Cancer Letters, vol. 84. No. 1, pp. 31-41 (1994).
Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).
Mak IT, Weglicki WB. Antioxidant properties of calcium channel blocking drugs. Methods Enzymol. 1994;234:620-630.
Maki, K.C., et al., "Baseline lipoprotein lipids and low-density lipoprotein cholesterol response to prescription omega-3 acid ethyl ester added to simvastatin therapy." Am J Cardiol., 105:1409-1412 (2010).
Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).
Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007).
Malinski T, Taha Z. Nitric oxide release from a single cell measured in situ by a porphyrinic-based microsensor. Nature. 1992;358:676-678.
Mallat, Z., et al., "Apoptosis in the vasculature: mechanisms and functional importance." British Journal of Pharmacology 130:947-962 (2000).
Mallat, Z., et al., "Protective role of interleukin-10 in atherosclerosis." Circ. Res. 85:e17-e24 (1999).
Marangell, Lauren B., M.D., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003).
Marckmann, P., "Fishing for heart protection." Am J Clin Nutr, 78:1-2 (2003).
Marder, "An Approach to Treatment Resistance in Schizophrenia," British Journ. Psychiatry, 37:19-22 (1999).
Martinez-Gonzalez J, Raposo B, Rodriguez C, Badimon L. 3-hydroxy-3-methylglutaryl coenzyme a reductase inhibition prevents endothelial no synthase downregulation by atherogenic levels of native Idls: Balance between transcriptional and post-transcriptional regulation. Arterioscler. Thromb. Vasc. Biol. 2001;21:804-809.
Martin-Jadraque, R. et al., Effectiveness of low dose crystalline nicotinic acid in men with low density lipoprotein cholesterol levels. Arch. Int. Med. 156: 1081-1088. (1996).
Martz, "Moving Upstream in Huntington's," Science-Business eXchange, 2 pgs., 2008.
Mason et al., "Comparative lipid antioxidant effects of omega-3 fatty acids in combination with HMG-CoA reductase inhibitors," Journ. Clin. Lipidology (2011) 5(3):20.
Mason RP, Gonye GE, Chester DW, Herbette LG. Partitioning and location of Bay K 8644, 1,4-dihydropyridine calcium channel agonist, in model and biological membranes. Biophys. J. 1989;55(4):769-778.
Mason RP, Jacob RF, Kubant R, Walter MF, Bellamine A, Jacoby A, Mizuno Y, Malinski T. Effect of enhanced glycemic control with saxagliptin on endothelial nitric oxide release and CD40 levels in obese rats. J. Atheroscler. Thromb. 2011;18:774-783.

(56) References Cited

OTHER PUBLICATIONS

Mason Rp, Jacob RF. Membrane microdomains and vascular biology: Emerging role in atherogenesis. Circulation. 2003; 107:2270-2273.
Mason RP, Kalinowski L, Jacob RF, Jacoby AM, Malinski T. Nebivolol reduces nitroxidative stress and restores nitric oxide bioavailability in endothelium of black americans. Circulation. 2005;112:3795-3801.
Mason RP, Kubant R, Heeba G, Jacob RF, Day CA, Medlin YS, Funovics P, Malinski T. Synergistic effect of amlodipine and atorvastatin in reversing ldl-induced endothelial dysfunction. Pharm. Res. 2008;25:1798-1806.
Mason RP, Walter MF, Day CA, Jacob RF. Active metabolite of atorvastatin inhibits membrane cholesterol domain formation by an antioxidant mechanism. J. Biol. Chem. 2006;281(14):9337-9345.
Mason RP, Walter MF, Day CA, Jacob RF. Intermolecular differences for HMG-CoA reductase inhibitors contribute to distinct pharmacologic and pleiotropic actions. Am. J Cardiol. 2005;96(5A):11F-23F.
Mason RP, Walter MF, Jacob RF. Effects of hmg-coa reductase inhibitors on endothelial function: Role of microdomains and oxidative stress. Circulation. 2004;109:II34-II41.
Mason RP, Walter MF, Mason PE. Effect of oxidative stress on membrane structure: Small angle x-ray diffraction analysis. Free Radic. Biol. Med. 1997;23(3):419-425.
Mason RP. Molecular basis of differences among statins and a comparison with antioxidant vitamins. Am. J. Cardiol. 2006;98:34P-41P.
Mataki et al., "Effect of Eicosapentaenoic Acid in Combination with HMG-CoA Reductase Inhibitor on Lipid Metabolism," Int. Med. J. 5(1):35-36 (Mar. 1998).
Mater, M.K., et al., "Arachidonic acid inhibits lipogenic gene expression in 3T3-L1 adipocytes through a prostanoid pathway." J. Lipid Res. 39:1327-1334 (1998).
Matsumoto, M., et al., "Orally administered eicosapentaenoic acid reduces and stabilizes atherosclerotic lesions in ApoE-deficient mice." Atherosclerosis, 197(2):524-533 (2008).
Matsuzaki et al., "Incremental Effects of Eicosapentaenoic Acid on Cardiovascular Events in Statin-Treated Patients with Coronary Artery Disease," Circ. J. 73:1283-1290 (2009).
Matsuzawa, Y., et al., "Effect of Long-Term Administration of Ethyl Icosapentate (MND-21) in Hyperlipaemic Patients," J. Clin Therapeutic & Medicines, 7: 1801-16 (1991).
Mattson MP. Modification of ion homeostasis by lipid peroxidation: roles in neuronal degeneration and adaptive plasticity. Trends Neurosci. 1998;21(2):53-57.
Mayatepek, E., et al., The Lancet, vol. 352, Leukotriene C4-synthesis deficiency: a new inborn error of metabolism linked to a fatal developmental syndrome, pp. 1514-1517 (1998).
Mayo Clinic at http://www.mayoclinic.org.diseases-conditions/high-blood-cholesterol/in-depth/cholesterol (2014).
McElroy, S.L., et al., "Clozapine in the Treatment of Psychotic Mood Disorders, Schizoaffective Disorder, and Schizophrenia", Journal of Clinical Psychiatry, vol. 52, No. 10, pp. 411-414 (1991).
McIntyre M, Hamilton CA, Rees DD, Reid JL, Dominiczak AF. Sex differences in the abundance of endothelial nitric oxide in a model of genetic hypertension. Hypertension. 1997;30:1517-1524.
McKenney et al., "Prescription omega-3 fatty acids for the treatment of hypertriglyceridemia," Am. J. Health Syst. Pharm., 64(6):595-605 (2007).
McKenney et al., CMRO, "Comparison of the efficacy of rosuvastatin versus atorvastatin, simvastatin and pravastatin in achieving lipid goals: results from the STELLAR trial", 689-98 (2003).
McKenney, J., "Niacin for dyslipidemia: considerations in product selection", Am. J. Health Syst. Pharm., 60:995-1005, (2003).
McKenney, J.M. et al. Study of the pharmacokinetic interaction between simvastatin and prescription omega-3-acid ethyl esters. J. Clin. Pharmacol. 46, 785-791 (2006).

McKenney, James et al., "Role of prescription omega-3 fatty acids in the treatment of Hypertriglyceridemia," Pharmacotherapy, LNKD—Pubmed: 17461707, vol. 27, No. 5, pp. 715-728 (2007).
McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (1997).
McMurchie, E.J., et al., "Incorporation and effects of dietary eicosapentaenoate (20 : 5(n-3)) on plasma and erythrocyte lipids of the marmoset following dietary supplementation with differing levels of linoleic acid." Biochimica et Biophysics Acta, 1045:164-173 (1990).
McNamara JR, et al., Remnant-like particle (RLP) Cholesterol is an independent cardiovascular disease risk factor in women: results from the Framingham Heart Study, Atherosclerosis, vol. 154(1), pp. 229-236 (2001).
Menuet, R. et al., "Importance and management of dyslipidemia in the metabolic syndrome," American Journal of the Medical Sciences Dec. 2005 US, vol. 33, No. 6, pp. 295-302 (2005).
Merched, A.J., et al., "Atherosclerosis: evidence for impairment of resolution of vascular inflammation governed by specific lipid mediators." FASEB J. 22:3595-3606 (2008).
Mesa, M., "Effects of oils rich in Eicosapentaenoic and docosahexaenoic acids on the oxidizability and thrombogenicity of low-density lipoprotein," Artherosclerosis 175, pp. 333-343 (2004).
Metcalf, R.G. et al., "Effect of dietary n-3 polyunsaturated fatty acids on the inducibility of ventricular tachycardia in patients with ischemic cardiomyopathy." Am J Cardiol 101:758-761 (2008).
Metcalf, R.G., et al., "Effects of fish-oil supplementation on myocardial fatty acids in humans." Am J Clin Nutr 85:1222-28 (2007).
Meyer, et al., "Dose-Dependent Effects of Docosahexaenoic Acid Supplementation on Blood Lipids in Statin-Treated Hyperlipidaemic Subjects." Lipids, 42:109-115 (2007).
Meyers, et al., "Nicotinic acid induces secretion of prostaglandin D2 in human macrophages: An in vitro model of the niacin-flush", Atherosclerosis, 192:253-258, (2007).
Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. 2004;24:136-140.
Michos et al., "Niacin and Statin Combination Therapy for Atherosclerosis Regression and Prevention of Cardiovascular Disease Events," Journ. Amer. Coll. Cardiol., vol. 59, No. 23:2058-2064 (2012).
Mii, S. et al., "Perioperative use of eicosapentaenoic acid and patency of infrainguinal vein bypass: a retrospective chart review." Curr Ther Res Clin Exp. 68:161-174 (2007).
Miles, et al., "Effect of orlistat in overweight and obese patients with type 2 diabetes treated with metformin," Diabetes Care, 25(7):1123-1128 (2002).
Miller AK, DiCicco RA, Freed MI. The effect of ranitidine on the pharmacokinetics of rosiglitazone in healthy adult male volunteers. Clin. Ther. 2002;24:1062-1071.
Miller AK, Inglis AM, Culkin KT, Jorkasky DK, Freed MI. The effect of acarbose on the pharmacokinetics of rosiglitazone. Eur. J. Clin. Pharmacol. 2001;57:105-109.
Miller M, Stone NJ, Ballantyne C, et al. Triglycerides and cardiovascular disease: a scientific statement from the American Heart Association. Circulation. 2011;123:2292-2333.
Miller, M., et al., "Impact of lowering triglycerides on raising HDL-C in hypertriglyceridemic and non-hypertriglyceridemic subjects." International Journal of Cardiology 119:192-195 (2007).
Minihane, A.M., et al., "ApoE polymorphism and fish oil supplementation in subjects with an atherogenic lipoprotein phenotype." Arterioscler. Thromb. Vasc. Biol. 20:1990-1997 (2000).
Mishra, A., et al., "Oxidized omega-3 fatty acids inhibit NF-?B activation via a PPAR?-Dependent Pathway." Arterioscler Thromb Vasc Biol. 24:1621-1627 (2004).
Mita, T. et al., Eicosapentaenoic acid reduces the progression of carotid intima-media thickness in patients with type 2 diabetes, Atherosclerosis 191:162-167 (2007).
Mizota M, Katsuki Y, Mizuguchi K, Endo S, Miyata H, Kojima M, Kanehiro H et al. "Pharmacological studies of eicosapentaenoic

(56) References Cited

OTHER PUBLICATIONS acid ethylester (EPA E) on high cholesterol diet-fed rabbits," Nippon Yakurigaku Zasshi, 91:255-66 (1988) (with English abstract).

Mizota M, Katsuki Y, Mizuguchi K, Endo S, Miyata H, Kojima M, Kanehiro H et al. "The effects of eicosapentaenoic acid ethylester (EPA E) on arterial thrombosis in rabbits and vascular lesions in rats," Nippon Yakurigaku Zasshi, 91:81-9 (1988)(with English abstract).

Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol., 59:3307-12 (1992).

Mizuguchi, K., et al., "Ethyl all-cis-5,8,11,14,17-icosapentaenoate modifies the biochemical properties of rat very low-density lipoprotein." European Journal of Pharmacology, 231:221-227 (1993).

Mizuguchi, K., et al., "Mechanism of the lipid-lowering effect of ethyl all-cis-5,8,11,14,17-icosapentaenoate." European Journal of Pharmacology, 231:121-127 (1993).

Mochida Press Release, Pharmaceutical Col., Ltd.: Conclusion of Distributorship Agreement Concerning Switch-OTC Drug for Hyperlipidemia Treatment, Epadel, (2009).

Mochida, Announcement, Mochida Announces Completion of "JELIS" Major Clinical Trial for "Epadel," 2005.

Mochida's Epadel Reduces Risk of Stroke Recurrence—New Results of JELIS Major Clinical Trial, JCNNetwork Newswire Nov. 13, 2006.

Mora, S., et al., "LDL particle subclasses, LDL particle size, and carotid atherosclerosis in the Multi-Ethnic Study of Atherosclerosis (MESA)." Atherosclerosis. 2007;192:211-217 (2007).

Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (2000).

Mori TA, Woodman RJ. "The independent effects of eicosapentaenoic acid and docosahexaenoic acid on cardiovascular risk factors in humans," Curr Opin Clin Nutr Metab Care 2006; 9:95-104 (2006).

Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 2000; 71:1085-1094 (2000).

Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (2003).

Mori, Trevor A., et al., "Docosahexaenoic Acid but Not Eicosapentaenoic Acid Lowers Ambulatory Blood Pressure and Heart Rate in Humans", Hypertension, 34(2):253-60 (Aug. 1999).

Morita, I., et al., "Effects of purified eicosapentaenoic acid on arachidonic acid metabolism in cultured murine aortic smooth muscle cells, vessel walls and platelets." Lipids 18:42-490 (1983).

Morrow, JD, "Release of markedly increased quantities of prostaglandin D2 in vivo in humans following the administration of nicotinic acid", Prostaglandins, 38:263-274, (1989).

Morton, R.E., "Specificity of lipid transfer protein for molecular species of cholesteryl ester." J Lipid Res., 27:523-529 (1986).

Mosher LR et al., "Nicotinic Acid Side Effects and Toxicity: A review," Am J Psychiat., 126: 1290-1296 (1970).

Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).

Mozaffarian et al., "Omega-3 fatty acids and cardiovascular disease: effects on risk factors, molecular pathways and clinical events," J. Am. Coll. Cardiol. (2011) 58(2):2047-2067.

Mozaffarian, "JELIS, fish oil, and cardiac events," www.thelancet.com vol. 369, pp. 1062-1063 (2007).

Mozaffarian, D., "Fish and n-3 fatty acids for the prevention of fatal coronary heart disease and sudden cardiac death." Am J Clin Nutr, 87:1991S-6S (2008).

Mozaffarian, D. et al., "Dietary fish and ω-3 fatty acid consumption and heart rate variability in US adults." Circulation, 117:1130-1137 (2008).

Naba, H., et al., "Improving effect of ethyl eicosapentanoate on statin-induced rhabdomyolysis in Eisai hyperbilirubinemic rats." Biochemical and Biophysical Research Communications, 340:215-220 (2006).

Nagakawa et al., Effect of [EPA] on the Platelet Aggregation and Composition of Fatty Acidin Man: A Double Blind Study, Atherosclerosis 47(1):71-75 (1983).

Naik H, Wu JT, Palmer R, McLean L. The effects of febuxostat on the pharmacokinetic parameters of rosiglitazone, a CYP2C8 substrate. Br. J. Clin. Pharmacol. 2012;74:327-335.

Nakamura et al., Remnant lipoproteniemia is a risk factor for endothelial vasomotor dysfuction and coronary artery disease in metabolic syndrome, Atherosclerosis, vol. 181(2), pp. 321-327 (2005).

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).

Nakamura, H., et al., "Evaluation of ethyl icosapentate in the treatment of hypercholesterolemia in kidney transplant recipients." Transplantation Proceedings, 30:3047-3048 (1998).

Nakamura, N. et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999).

Nambi, V., et al., "Combination therapy with statins and omega-3 fatty acids." Am J Cardiol 98:34i-38i (2006).

Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).

Nattel, S., et al., "Atrial remodeling and atrial fibrillation: Mechanisms and implications." Circ Arrhythmia Electrophysiol, 1:62-73 (2008).

Negre-Salvayre, A., et al., "Advanced lipid peroxidation end products in oxidative damage to proteins. Potential role in diseases and therapeutic prospects for the inhibitors." British Journal of Pharmacology 153:6-20 (2008).

Nelson, G.J., et al., "The Effect of Dietary Docosahexaenoic Acid on Plasma Lipoproteins and Tissue Fatty Acid Composition in Humans", Lipids, 32(11):1137-1146, (1997).

Nemets, Boris, M.D., "Addition of Omega-3 Fatty Acid to Maintenance Medication Treatment for Recurrent Unipolar Depressive Disorder", Am. J. Psychiatry, 159(3):477-479, (Mar. 2002).

Nemoto et al., "Ethyl-eicosapentaenoic Acid Reduces Liver Lipids and Lowers Plasma Levels of Lipids in Mice Fed a High-Fat Diet, in vivo," 23:685-690 2009).

Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (1992).

Nestel, et al., "The n-3 fatty acids eicosapentaenoic acid and docosahexaenoic acid increase systemic arterial compliance in humans," Am J Clin Nutr., 76:326-30 (2002).

Nestel, P.J., "Effects of N-3 fatty acids on lipid metabolism." Ann Rev Nutr., 10:149-167 (1990).

Niemi M, Backman JT, Grantors M, Laitila J, Neuvonen M, Neuvonen PJ. Gemfibrozil considerably increases the plasma concentrations of rosiglitazone. Diabetologia. 2003;46: 1319-1323.

Niemi M, Backman JT, Neuvonen PJ. Effects of trimethoprim and rifampin on the pharmacokinetics of the cytochrome P450 2C8 substrate rosiglitazone. Clin. Pharmacol. Ther. 2004;76:239-249.

(56) References Cited

OTHER PUBLICATIONS

Nigon F, Lesnik P, Rouis M, Chapman MJ. Discrete subspecies of human low density lipoproteins are heterogeneous in their interaction with the cellular LDL receptor. J. Lipid Res. 1991;32(11):1741-1753.
Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (1997).
Nobukata, H., et al., "Age-related changes in coagulation, fibrinolysis, and platelet aggregation in male WBN/Kob rats." Thrombosis Research 98: 507-516 (2000).
Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).
Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).
Noguchi et al., "Chemoprevention of DMBA-induced mammary carcinogenesis in rats by low-dose EPA and DHA." Br. J. Cancer 75(3): 348-353 (1997).
Nomura et al., "The effects of pitavastatin, eicosapentaenoic acid and combined therapy on platelet-derived microparticles and adiponectin in hyperlipidemic, diabetic patients." Platelets, 20(10:16-22 (2009).
Nourooz-Zadeh, J., et al., "Urinary 8-epi-PGF2? and its endogenous ?-oxidation products (2,3-dinor and 2,3-dinor-5,6-dihydro) as biomarkers of total body oxidative stress." Biochemical and Biophysical Research Communications 330:731-736 (2005).
Nozaki S. et al., "Effects of purified Eicosapentaenoic acid ethyl ester on plasma lipoproteins in primary hypercholesterolemia" Int J Vitam Nutr Res. 62(3):256-60 (1992).
Obata, et al., "Eicosapentaenoic acid inhibits prostaglandin D2 generation by inhibiting cyclo-oxygenase in cultured human mast cells", Clin. & Experimental Allergy, 29:1129-1135, (1999).
O'Donnell, C.J., et al., "Leukocyte telomere length and carotid artery intimal medial thickness—the Framingham heart study." Arteriosclerosis, Thrombosis, and Vascular Biology.28:1165-1171 (2008).
Oemar BS, Tschudi MR, Godoy N, Brovkovich V, Malinski T, Luscher TF. Reduced endothelial nitric oxide synthase expression and production in human atherosclerosis. Circulation. 1998;97:2494-2498.
Oh, Robert C et al., Management of Hypertriglyceridemia, American Family Physician, LNKD-PUBMED: 17508532, vol. 75, No. 9, pp. 1365-1371 (2007).
Ohara Y, Peterson TE, Harrison DG. Hypercholesterolemia increases endothelial superoxide anion production. J. Clin. Invest. 1993;91:2546-2551.
Okuda, Y. et al., Eicosapentaenoic acid enhances nitric oxide production by cultured human endothelial cells. Biochem. Biophys. Res. Commun. 232: 487-491 (1997).
Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).
Okumura, T., et al., "Eicosapentaenoic acid improves endothelial function in hypertriglyceridemic subjects despite increased lipid oxidizability." Am J Med Sci 324(5):247-253 (2002).
Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126, 261-268 (1992).
Olofsson et al., "Apolipoprotein B : a clinically important apolipoprotein which assembles atherogenic lipoproteins and promotes the development of atherosclerosis" Journal of Internal Medicine, 258: 395-410 (2005).
Omacor® Prescribing Information (Omega-3-acid ethyl esters, capsules) (2004).
Omacor®, Physicians' Desk Reference 2735 (60th ed. 2006).
Ona, V.O., et al., Nature, vol. 399, Inhibition of caspase-1 slows disease progression in a mouse model of Huntington's disease, pp. 263-267 (1999).
Ooi EM, "Apolipoprotein C-III: Understanding an emerging cardiovascular risk factor", Clin.Sci. (London), vol. 114, pp. 611-624 (2008).
Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003).
Osher et al., "Omega-3 Eicosapentaenoic Acid in Bipolar Depression: Report of a Small Open-Label Study," J. Clin. Psych. 66:726-729 (2005).
Ou Z, Ou J, Ackerman AW, Oldham KT, Pritchard KA, Jr. L-4f, an apolipoprotein a-1 mimetic, restores nitric oxide and superoxide anion balance in low-density lipoprotein-treated endothelial cells. Circulation. 2003;107:1520-1524.
Ozaki M, Kawashima S, Yamashita T, Hirase T, Namiki M, Inoue N, Hirata K, Yasui H, Sakurai H, Yoshida Y, Masada M, Yokoyama M. Overexpression of endothelial nitric oxide synthase accelerates atherosclerotic lesion formation in apoe-deficient mice. J. Clin. Invest. 2002; 110:331-340.
Ozawa A, Nakamura E, Jinbo H. Fujita T, Hirai A, Terano T, Hamazaki T et al. "Measurement of higher lipids in the fractions of human red blood cell membranes, blood platelets and plasma, using thin layer chromatography and gas chromatography," Bunseki Kagaku, 32:174-8 (1982).
Park JH, Park DI, Kim HJ, et al. Metabolic syndrome is associated with erosive esophagitis. World J. Gastroenterol. Sep. 2008 14 (35): 5442-7.
Park JY, Kim KA, Kang MH, Kim SL, Shin JG. Effect of rifampin on the pharmacokinetics of rosiglitazone in healthy subjects. Clin. Pharmacol. Ther. 2004;75:157-162.
Park, Y., et al., "Omega-3 fatty acid supplementation accelerates chylomicron triglyceride clearance." J. Lipid Res. 44:455-463 (2003).
Patel et al., "Rosiglitazone monotherapy improves glycaemic control in patients with type 2 diabetes: a twelve-week randomized, placebo-controlled study," Diabetes, Obesity and Metabolism, vol. 1, pp. 165-172 (1999).
Paton, CM, Ntambi, JM., Biochemical and physiological function of stearoyl-CoA desaturase, Am. J. Physiol. Endocrinol. Metab. 2009;297:E28-E37.
PCT/GB00/00164 International Search Report dated Oct. 20, 2000.
PCT/US2011/062247 International Search Report and Written Opinion dated Jun. 14, 2012.
PCT/US2013/020526 International Search Report dated Mar. 29, 2013.
PCT/US2013/048241 International Search Report dated Dec. 13, 2013.
PCT/US2013/048516 International Search Report dated Dec. 20, 2013.
PCT/US2013/048559 International Search Report dated Dec. 13, 2013.
PCT/US2013/068647 International Search Report and Written Opinion dated May 13, 2014.
PCT/US2014/019454 International Search Report and Written Opinion dated Jun. 3, 2014.
Pedersen RS, Damkier P, Brosen K. The effects of human CYP2C8 genotype and fluvoxamine on the pharmacokinetics of rosiglitazone in healthy subjects. Br. J. Clin. Pharmacol. 2006;62:682-689.
Pedersen, T., et al., "Randomised trial of cholesterol lowering in 4444 patients with coronary heart disease: the Scandinavian Simvastation Survival Study (4S)", The Lancet, No. 19, vol. 344, 8934, p. 1383-1389 (1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919, (2002).

(56) References Cited

OTHER PUBLICATIONS

Peet, M., et al., Phospholipid Spectrum Disorder in Psychiatry pp. 1-19, (1999).
Pejic et al., "Hypertriglyceridimia," Journ. Amer. Board Fam. Med., vol. 19(3):310-316 (2006).
Pennathur S, Heinecke JW. Mechanisms for oxidative stress in diabetic cardiovascular disease. Antioxid. Redox Signal. 2007;9(7):955-969.
Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358 (1998).
Piche, "Tumor Necrosis Factor-Alpha, and Fi brinogen to Abdominal Adipose Tissue, Blood Pressure, and Cholesterol and Triglyceride Levels in Healthy Postmenopausal Women", American Journal of Cardiology, 2005, 96(1), 92-97.
Pike, NB, "Flushing out the role of GPR109A (HM74V) in the clinical efficacy of nicotinic acid", J. Clin. Invest., 115:3400-3403, (2005).
Plusepa® Product brochure "Super Critically" Different from Other Omega-3 Fish Oil Supplements for Depression and ADHD, by Minami Nutrition (Apr. 2009, pp. 1-6).
Pownall, H.J., et al., "Correlation of serum triglyceride and its reduction by ?-3 fatty acids with lipid transfer activity and the neutral lipid compositions of high-density and low-density lipoproteins." Atherosclerosis 143:285-297 (1999).
Press Release: Amarin Corporation Says Huntington's Diease Drug Failed in Trials, http://www.fiercebiotech.com/node/6607/print (Apr. 24, 2007) (Printed on Aug. 22, 2008).
Pritchard KA, Ackerman AW, Ou J, Curtis M, Smalley DM, Fontana JT, Stemerman MB, Sessa WC. Native low-density lipoprotein induces endothelial nitric oxide synthase dysfunction: Role of heat shock protein 90 and caveolin-1. Free Radic. Biol. Med. 2002;33:52-62.
Pritchard KA, Jr., Groszek L, Smalley DM, Sessa WC, Wu M, Villalon P, Wolin MS, Stemerman MB. Native low-density lipoprotein increases endothelial cell nitric oxide synthase generation of superoxide anion. Circ. Res. 1995;77:510-518.
Puri, B., et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (2001).
Puri, B., et al., Archives of General Psychiatry, No. 55, "Sustained remission of positive and negative symptoms of schizophrenia following treatment with eicosapentaenoic acid," pp. 188-189, (1998).
Puri, B.K., et al., "Ethyl-EPA in Huntington Disease: A Double-Blind, Randomized, Placebo-Controlled Trial", Neurology, 65:286-292, (2005).
Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).
Rader, Lipid Disorders, in Eric J. Topol (ed.)Textbook of Cardiovascular Medicine pp. 55-75 (2007).
Rahimy M, Hallen B, Narang P. Effect of tolterodine on the anticoagulant actions and pharmacokinetics of single-dose warfarin in healthy volunteers. Arzneimittelforschung 2002 52 (12): 890-5.
Raitt, M.H., et al., "Fish oil supplementation and risk of ventricular tachycardia and ventricular fibrillation in patients with implantable defibrillators—a randomized controlled trial." JAMA. 293(23):2884-2891 (2005).
Rambjor, Gro S., et al., "Elcosapentaenoic Acid is Primarily Responsible for Hypotrigylceridemic Effect of Fish Oil in Humans", Fatty Acids and Lipids from Cell Biology to Human Disease: Proceedings of the 2nd international Congress of the ISSFAL (International Society for the Study of Fatty Acids and Lipids, AOCS Press, 31:S-45-S-49, (1996).

Randomised trial of cholesterol lowering in 4444 patients with coronary heart disease. The Scandinavian Simvastatin Survival Study, Lancet. 344: 1383-1389 (1994).
Rao MN, Mullangi R, Katneni K, et al. Lack of effect of sucralfate on the absorption and pharmacokinetics of rosiglitazone. J. Clin. Pharmacol. 2002;42:670-675.
Recommendation for lipid plasma levels in Germany.
Rees DD, Palmer RM, Moncada S. The role of endothelium-derived nitric oxide in the regulation of blood pressure. Proc. Natl. Acad. Sci. USA. 1989;86:3375-3378.
Reiffel, J.A., et al., "Antiarrhythmic effects of omega-3 fatty acids." Am J Cardiol 98:50i-60i (2006).
Reiner Z, Catapano AL, De BG, et al. ESC/EAS Guidelines for the management of dyslipidaemias: the Task Force for the management of dyslipidaemias of the European Society of Cardiology (ESC) and the European Atherosclerosis Society (EAS). Eur. Heart J. 2011;32:1769-1818.
Ridker, "C-Reactive Protein : A Simple Test to Help Predict Risk of Heart Attack and Stroke", Circulation: Journal of the American Heart Association, 2003, 108, e81-e85.
Riediger, N.D., et al., "A systemic review of the roles of n-3 fatty acids in health and disease." J Am Diet Assoc. 109:668-679. (2009).
Rifai, "High-Sensitivity C-Reactive Protein: A Novel and Promising Marker of Coronary Heart Disease", Clinical Chemistry, 2001, 47(3), 403-411.
Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).
Rizzo M, Bemeis K. Low-density lipoprotein size and cardiovascular risk assessment. Q. J. Med. 2006;99(1): 1-14.
Roach, P.D., et al., "The effects of dietary fish oil on hepatic high density and low density lipoprotein receptor activities in the rat." FEBS Lett., 222: 159-162 (1987).
Robinson, J.G., et al., "Meta-analysis of the relationship between non-high-density lipoprotein cholesterol reduction and coronary heart risk." J Am Coll Cardiol., 53: 316-322 (2009).
Roche, H.M., et al., "Effect of long-chain n-3 polyunsaturated fatty acids on fasting and postprandial triacylglycerol metabolism." Am J Clin Nutr 71:232S-7S (2000).
Roche, H.M., et al., "Long-chain n-3 polyunsaturated fatty acids and triacylglycerol metabolism in the postprandial state." Lipids 34: S259-S265 (1999).
Rodriguez, Y., et al., "Long-chain ?6 polyunsaturated fatty acids in erythrocyte phospholipids are associated with insulin resistance in non-obese type 2 diabetics." Clinica Chimica Acta 354:195-199 (2005).
Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).
Rost KL, Roots I. Nonlinear kinetics after high-dose omeprazole caused by saturation of genetically variable CYP2C19. Hepatology Jun. 1996 23 (6): 1491-7.
Rubins, HB, et al., "Distribution of lipids in 8,500 men with coronary artery disease: Department of Veterans Affairs HDL Intervention Trial Study Group," Am. J. Cardiol, 75:1196-1201, (1995).
Rubins, HB, et al., "Gemfibrozil for the prevention of coronary heart disease in men with low levels of high-density lipoprotein cholesterol: Veterans Affairs HDL-C Intervention Trial Study Group", N. Eng. J. Med., 341:410-418, (1999).
Ruiz-Narváez, E.A., et al., "Abdominal obesity and hyperglycemia mask the effect of a common APOC3 haplotype on the risk of myocardial infarction." Am J Clin Nutr 87:1932-8 (2008).
Ruocco MJ, Shipley GG. Interaction of cholesterol with galactocerebroside and galactocerebroside phosphatidylcholine bilayer membranes. Biophys. J. 1984;46:695-707.
Rustan, A.C., et al., "Eicosapentaenoic acid inhibits cholesterol esterification in cultured parenchymal cells and isolated microsomes from rat liver." J. Bio. Chem. 263(17):8126-32 (1988).

(56) References Cited

OTHER PUBLICATIONS

Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).

Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).

Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).

Ryan, A.S., et al., "Clinical overview of algal-docosahexaenoic acid: effects on triglyceride levels and other cardiovascular risk factors." Am J Ther., 16:183-192 (2009).

Sacks, Frank M., "The apolipoprotein story," Atherosclerosis Supplements, 23-27 (2006).

Saito et al., "Effects of EPA on coronary artery disease in hypercholesterolemic patients with multiple risk factors: Sub-analysis of primary prevention cases from the Japan EPA Lipid Intervention Study (JELIS)," Atherosclerosis, 200:135-140 (2008).

Saito et al., "Results of Clinical Usage of Improved Formulation (MND-21S) Epadel Capsule 300 with Respect to Hyperlipidemia," 26(12) Jpn. Pharmacol. Ther. 2047-62 (1998).

Saito, J., et al., "Mechanisms of enhanced production of PGI2 in cultured rat vascular smooth muscle cells enriched with eicosapentaenoic acid." Atherosclerosis 131: 219-228 (1997).

Sampath H , Ntambi JM., Role of stearoyl-CoA desaturase in human metabolic disese, Future Lipidol. 2008;3.163-73.

Sampath H, Ntambi JM., The Role of stearoyl-CoA desaturase in obesity, insulin resistance, and inflammation, Ann. NY. Acad. Sci. 2011; 1243:4 7-53.

Samuels, Martin A., M. D., et al., "Huntington's Disease", Office Practice of Neurology, (122):654-655, (1996).

Sanders, A. Hinds and C.C. Pereira, "Influence of n-3 fatty acids on blood lipids in normal subjects" Journal of Internal Medicine. 225:99-104,(1989).

Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (2006).

Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).

Sanders, T.A., et al., "Triglyceride-lowering effect of marine polyunsaturates in patients with hypertriglyceridemia." Arterioscler. Thromb. Vasc. Biol. 5:459-465 (1985).

Sasaki J, Miwa T, Odawara M. Administration of highly purified eicosapentaenoic acid to statintreated diabetic patients further improves vascular function. Endocr. J. 2012;59:297-304.

Sasaki J, Yokoyama M, Matsuzaki M, et al. Relationship between coronary artery disease and non-HDL-C, and effect of highly purified EPA on the risk of coronary artery disease in hypercholesterolemic patients treated with statins: sub-analysis of the Japan EPA Lipid Intervention Study (JELIS). J. Atheroscler. Thromb. 2012;19:194-204.

Sasaki, Y.F., et al., "Bio-anticlastogenic effects of unsaturated fatty acids included in fish oil—docosahexaenoic acid, docosapentaenoic acid, and eicosapentaenoic acid in cultured Chinese hamster cells." Mutation Research, 320: 9-22 (1994).

Sato et al., "General Pharmacological Studies on 5 8 11 14 17 Eicosapentaenoic Acid Ethyl Ester EPA-E", Folia Pharmacol JPN, 94 (1), 35-48. (1989).

Sato, "Effects of Highly Purified Ethyl All-cis-5,8,11,14,17-icosapentaenoate (EPA-E) on Rabbit Platelets," Biol. Pharm. Bull., 16(4)362-367 (1993).

Satoh, N., et al., "Purified eicosapentaenoic acid reduces small dense LDL, remnant lipoprotein particles, and C-reactive protein in metabolic syndrome." Diabetes Care, 30(1): 144-146 (2007).

Satoh-Asahara N, Shimatsu A, Sasaki Y, Nakaoka H, Himeno A, Tochiya M, Kono S, Takaya T, Ono K, Wada H, Suganami T, Hasegawa K, Ogawa Y. Highly purified eicosapentaenoic acid increases interleukia-10 levels of peripheral blood monocytes in obese patients with dyslipidemia.Diabetes Care. 2012;35(12):2631-2639.

Schaefer, E.J., et al., "Effects of eicosapentaenoic acid, docosahexaenoic acid, and olive oil on cardiovascular disease risk factors [abstract 20007]." Circulation, 122:A20007 (2010).

Schectman, G. & Hiatt, J., "Drug therapy for hypercholesterolemia in patients with cardiovascular disease: factors limiting achievement of lipid goals", Am. J. Med., 100:197-204, (1996).

Schectman, G., et al., "Dietary fish oil decreases low-density-lipoprotein clearance in nonhuman primates." Am J Clin Nutr., 64:215-221 (1996).

Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).

Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).

Schmitz PG, McCloud LK, Reikes ST, et al. Prophylaxis of hemodialysis graft thrombosis with fish oil: double-blind, randomized, prospective trial. J. Am. Soc. Nephrol. Jan. 2002 13 (1): 184-90.

Schmitz, G., et al., "The opposing effects of n-3 and n-6 fatty acids." Progress in Lipid Research, 47:147-155 (2008).

Schreiner et al., Lipoprotein[a] as a Risk Factor for Preclinical Atherosclerosis, 13 Atherosclerosis, Thrombosis & Vascular Biology 826, 826 (1993).

Schuirmann, D.J. A comparison of the two one-sided tests procedure and the power approach for assessing the equivalence of average bioavailability. J. Pharmacokinet. Biopharm. 15, 657-680 (1987).

Schwarz, S., et al., "Lycopene inhibits disease progression in patients with benign prostate hyperplasia." J. Nutr. 138: 49-53 (2008).

Schwellenbach et al., "The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides." J. Am. Coll. Nutr. 25(6):480-485 (2006).

Segrest et al., Structure of Apolipoprotein B-100 in Low Density Lipoproteins, J. Lipid Res. 42(9):1346-1367 (2001).

Self-Medlin Y, Byun J, Jacob RF, Mizuno Y, Mason RP. Glucose promotes membrane cholesterol crystalline domain formation by lipid peroxidation. Biochim. Biophys. Acta. 2009; 1788(6): 1398-1403.

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Sevanian A, Ursini F. Lipid peroxidation in membranes and low-density lipoproteins: similarities and differences. Free Radic. Biol. Med. 2000;29(3-4):306-311.

Shah, S., et al., "Eicosapentaenoic Acid (EPA) as an Adjunct in the Treatment of Schizophrenia", Schizophrenia Research, vol. 29, No. 1/02 (1998).

Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).

Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (2003).

Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).

(56) References Cited

OTHER PUBLICATIONS

Shimokawa H, Flavahan NA, Vanhoutte PM. Loss of endothelial pertussis toxin-sensitive g protein function in atherosclerotic porcine coronary arteries. Circulation. 1991;83:652-660.
Shinozaki K. et al., "The long-term effect of Eicosapentaenoic acid on serum levels of lipoprotein (a) and lipids in patients with vascular disease" J Atheroscler Thromb. 2(2):207-9 (1996).
Shishehbor MH, Brenna ML, Aviles RJ, Fu X, Penn MS, Sprecher DL, Hazen SL. Statins promote potent systemic antioxidant effects through specific inflammatory pathways. Circulation. 2003;108(4):426-431.
Sierra, S., et al., "Dietary eicosapentaenoic acid and docosahexaenoic acid equally incorporate as decosahexaenoic acid but differ in inflammatory effects." Nutrition 24: 245-254 (2008).
Silvers, Karen M., et al., "Randomised double-blind placebo-controlled trial of fish oil in the treatment of depression", Prostagandins, Leukotrienes and Essential Fatty Acids, 72:211-218, (2005).
Simoens, C.M., et al., "Inclusion of 10% fish oil in mixed medium-chain triacylglycerol-longchain triacylglycerol emulsions increases plasma triacylglycerol clearance and induces rapid eicosapentaenoic acid (20:5n-3) incorporation into blood cell phospholipids." Am J Clin Nutr 88: 282-8 (2008).
Simon, Joel A., et al., "Serum Fatty Acids and the Risk of Coronary Heart Disease", American Journal of Epidemiology, 142(5):469-476, (1995).
Simopoulos, "Omega-3 fatty acids in health and disease and in growth and development," Am. J. Clin. Nutr. 54:438-63 (1991).
Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005).
Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).
Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).
Skinner JS, Cooper A, & Feder GS and on behalf of the Guideline Development Group. "Secondary prevention for patients following a myocardial infarction; summary of NICE guidance," Heart, 93:862-864 (2007).
Slides for the Oct. 16, 2013 Meeting of the Endocrinologic and Metabolic Drugs Advisory Committee, 158 pages.
Smith et al., Pharmacokinetics and Pharmacodynamics of Epoetin Delta in Two Studies in Health Volunteers and Two Studies in Patients with Chronic Kidney Disease, Clinical Therapeutics/vol. 29, pp. 1368-1380 (2007).
Sniderman A, Kwiterovich PO. Update on the detection and treatment of atherogenic low-density lipoproteins. Curr. Opin. Endocrinol. Diabetes Obes. 2013;20:140-147.
Sohma, R., et al., "Protective effect of n-3 polyunsaturated fatty acid on primary culture of rat hepatocytes without glycemic alterations." Journal of Gastroenterology and Hepatology 22: 1965-1970 (2007).
Spector, A.A., "Arachidonic acid cytochrome P450 epoxygenase pathway." Journal of Lipid Research, 50: S52-S56 (2009) (published online on Oct. 23, 2008.).
Spector, A.A., et al., "Epoxyeicosatrienoic acids (EETs): metabolism and biochemical function." Progress in Lipid Research 43: 55-90 (2004).
Springer, T.A., "Traffic signals for lymphocyte recirculation and leukocyte emigration: The multistep paradigm." Cell, 76: 301-314 (1994).
Squires, RW, et al., "Low-dose, time release nicotinic acid: effects in selected patients with low concentrations of high density lipoprotein cholesterol", Mayo Clinic Proc., 67:855-860, (1992).
Srinivas, et al., "Controlled release of lysozyme from succinylated gelatin microspheres," J. Biomater. Sci., Polymer Ed., vol. 12(2):137-148 (2001).
Stalenhoef, A.F.H., et al., "The effect of concentrated n-3 fatty acids versus gemfibrozil on plasma lipoproteins, low density lipoprotein heterogeneity and oxidizability in patients with hypertrygliceridemia." Atherosclerosis 153: 129-138 (2000).
Stampfer MJ, Krauss RM, Ma J, et al. A prospective study of trig lyceride level, lowdensity lipoprotein particle diameter, and risk of myocardial infarction. JAMA. 1996;276:882-888.
Stark, K.D. & Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (2004).
Stark, K.D., "The percentage of n-3 highly unsaturated fatty acids in total HUFA as a biomarker for omega-3 fatty acid status in tissues." Lipids 43:45-53 (2008).
Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).
Steinberg D, Witztum JL. Is the oxidative modification hypothesis relevant to human atherosclerosis? Do the antioxidant trials conducted to date refute the hypothesis? Circulation. 2002;105:2107-2111.
Steinberg D. Lewis A. Conner Memorial Lecture: Oxidative modification of LDL and atherogenesis. Circulation. 1997;95(4):1062-1071.
Stepp DW, Ou J, Ackerman AW, Welak S, Klick D, Pritchard KA, Jr. Native ldl and minimally oxidized ldl differentially regulate superoxide anion in vascular endothelium in situ. Am. J. Physiol. 2002;283:H750-H759.
Stoll, Andrew L. et al., Omega 3 Fatty Acids in Bipolar Disorder, Arch. Gen. Psychiatry, 56:407-412, (May 1999).
Su, Kuan-Pin, et al., "Omega-3 Fatty Acids in Major Depressive Disorder a Preliminary Double-Blind, Placebo-Controlled Trial", European Neuropsychopharmacology, 13:267-271, (2003).
Sugiyama, E., et al., "Eicosapentaenoic acid lowers plasma and liver cholesterol levels in the presence of peroxisome proliferators-activated receptor alpha." Life Sciences, 83:19-28 (2008).
Superko et al., "Lipid Management to Reduce Cardiovascular Risk: A New Strategy is Required," Circulation, 117:560-568 (2008).
Surette, M.E., et al., "Dependence on dietary cholesterol for n-3 polyunsaturated fatty acidinduced changes in plasma cholesterol in the Syrian hamster." J Lipid Res., 33:263-271 (1992).
Surette, M.E., et al., "Evidence for mechanisms of the hypotriglyceridemic effect of n-3 polyunsaturated fatty, acids." Biochimica et Biophysic Acta, 1126: 199-205 (1992).
Takaki A, Umemoto S, Ono K, Seki K, Ryoke T, Fujii A, Itagaki T, Harada M, Tanaka M, Yonezawa T, Ogawa H, Matsuzaki M. Add-on therapy of epa reduces oxidative stress and inhibits the progression of aortic stiffness in patients with coronary artery disease and statin therapy: A randomized controlled study. J. Atheroscler. Thromb. 2011;18:857-866.
Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991).
Talayero BG, Sacks FM. The role of triglycerides in atherosclerosis. Curr. Cardiol. Rep. 2011;13:544-552.
Tamura, et al., "Study of the Clinical Usefulness of Ethyl Icosapentate (MND-21) in Long-Term Treatment of Hyperlipaemic Patients." J Clin Thera & Medicines, 7:1817-1834 (1991).
Tanaka et al., "Genome-Wide Association Study of Plasma Polyunsaturated Fatty Acids in the InCHIANTI Study." PLoS Genetics 5(1):1-8 (Jan. 2009).
Tanaka et al., "Suppression of prostaglandin synthesis by arachidonic acid or eicosapentaenoic acid in a macrophage-like cell line, RAW 264.7, treated with LPS," Biol. Pharm. Bull., 22(10):1057-7 (1999).
Tanaka, K.T., et al., "Reduction in the recurrence of stroke by eicosapentaenoic acid for hypercholesterolemic patients—Subanalysis of the JELIS trial." Stroke, 39(7):2052-8 (2008).
Tatarczyk, et al., "Analysis of long-chain ?-3 fatty acid content in fish-oil supplements," Wien Klin Wochenschr, 119/13-14: 417-422 (2007).

(56) References Cited

OTHER PUBLICATIONS

Tatsuno et al., Efficacy and safety of TAK-085 compared with eicosapentaenoic acid in Japanese subjects with hypertriglyceridemia undergoing lifestyle modification: The omega-3 fatty acids randomized double-blind (ORL) study, J. Clin. Lipid; vol. 7(6), pp. 615-625 (2013).
Taylor, A.J., et al., "Arterial Biology for the Investigation of the Treatment Effects of Reducing Cholesterol (ARBITER) 2: a double-blind, placebo-controlled study of extended-release niacin on atherosclerosis progression in secondary prevention patients treated with statins", Circulation, 110:3512-3517, (2004).
Tedgui, A., et al., "Anti-inflammatory mechanisms in the vascular wall." Circ. Res. 88:877-887 (2001).
Teissier E, Nohara A, Chinetti G, Paumelle R, Cariou B, Fruchart JC, Brandes RP, Shah A, Staels B. Peroxisome proliferator-activated receptor alpha induces NADPH oxidase activity in macrophages, leading to the generation of LDL with PPAR-alpha activation properties. Circ. Res. 2004;95(12):1174-1182.
Terano, et al., "Effect of Oral Administration of Highly Purified Eicosapentaenoic Acid on Platelet Function, Blood Vicosity and Red Cell Deformability in Healthy Human Subjects," Atherosclerosis, 46, 321-331 (1983).
Theilla, M., et al., "A diet enriched in eicosapentanoic acid, gamma-linolenic acid and antioxidants in the prevention of new pressure ulcer formation in critically ill patients with acute lung injury: A randomized, prospective, controlled study." Clinical Nutrition 26: 752-757 (2007).
Theobald et al., "LDL Cholesterol-Raising Effect of Low-Dose Docosahexaenoic Acid in Middle-Aged Men and Women," Am. J. Clin. Nutr. 79:558-63 (2004).
Thies, F., et al., "Association of n-3 polyunsaturated fatty acids with stability of atherosclerotic plaques: a randomised controlled trial." Lancet 361: 477-85 (2003).
Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).
Third Report of the NCEP Expert Panel on Detection, Evaluation, and Treatment of High Blood Cholesterol in Adults (Adult Treatment Panel III) Final Report, NIH Publication No. 02-5215 Sep. 2012.
Thorwest M, Balling E, Kristensen SD, et al. Dietary fish oil reduces microvascular thrombosis in a porcine experimental model. Thromb. Res. Jul. 2000 99 (2): 203-8.
Tilg H, Moschen AR. Inflammatory Mechanisms in the Regulation of Insulin Resistance. Mol. Med. 2008;14(3-4):222-231.
Tirosh et al., "Changes in Triglyceride Levels and Risk for Coronary Heart Disease in Young Men," American College of Physicians, pp. 377-385 (2007).
Torrejon, C. et al., "n-3 Fatty acids and cardiovascular disease: Actions and molecular mechanisms," Prostaglandins Leukotrienes & Essent. Fatty Acids, doi:10.1016/j.plefa.2007.10.014 (2007).
Transcript from Oct. 16, 2013 Meeting of the Endocrinologic and Metabolic Drugs Advisory Committee, 76 pages.
TREND-HD Investigators, Randomized controlled trial of ethyl-eicosapentaenoic acid in Huntington disease: the TREND-HD study, Arch Neurol., vol. 65(12): 1582-9 (2008).
Tribble DL, Holl LG, Wood PD, Krauss RM. Variations in oxidative susceptibility among six low density lipoprotein subfractions of differing density and particle size. Atherosclerosis. 1992;93(3):189-199.
Tribble DL, Rizzo M, Chait A, Lewis DM, Blanche PJ, Krauss RM. Enhanced oxidative susceptibility and reduced antioxidant content of metabolic precursors of small, dense low-density lipoproteins. Am. J. Med. 2001;110(2):103-110.
Trilipix Package Insert (2010).
Tsimikas S, Witztum JL, Miller ER, Sasiela WJ, Szarek M, Olsson AG, Schwartz GG. High-dose atorvastatin reduces total plasma levels of oxidized phospholipids and immune complexes present on apolipoprotein B-1 00 in patients with acute coronary syndromes in the MIRACL trial. Circulation. 2004;110(11):1406-1412.
Tsuruta K., et al.,"Effects of purified eicosapentaenoate ethyl ester on fibriolytic capacity in patients with stable coronary artery disease and lower extremity ischaemia" Coron Artery Dis. 7(11):837-42 (Nov. 1996).
Tulenko TN, Chen M, Mason PE, Mason RP. Physical effects of cholesterol on arterial smooth muscle membranes: Evidence of immiscible cholesterol domains and alterations in bilayer width C during atherogenesis. J. Lipid Res. 1998;39:947-956.
Tungsiripat, et al., "Dyslipidemia in HIV patients," Cleveland Clinic Journal of Medicine, v. 72, No. 12 (2005).
Turini et al., "Short-term fish oil supplementation improved innate immunity, but increased ex vivo oxidation of LDL in man—a pilot study." Eur. J. Nutr. 40:56-65 (2001).
U.S. Appl. No. 14/245,499, filed Apr. 4, 2014 (now abandoned).
U.S. Appl. No. 14/261,160, filed Apr. 24, 2014.
Ullian, M.E., "Fatty acid inhibition of angiotensin II-stimulated inositol phosphates in smooth muscle cells." Am J Physiol Heart Circ Physiol (1996).
Urakaze, Masaharu, et al., "Infusion of emulsified trieicosapentaenoylglycerol into rabbits. The effects on platelet aggregation, polymorphonuclear leukocyte adhesion, and fatty acid composition in plasma and platelet phospholipids", Thromb. Res., 44(5):673-682 (1986).
Urquhart et al., "Profile of eicosanoids produced by human saphenous vein endothelial cells and the effect of dietary fatty acids," Prostaglandins Leukot. Essent. Fatty Acid, 65(1):15-22 (2001.
US Food and Drug Administration and Dept of Health and Human Services. Substances affirmed as generally recognized as safe: Menhaden Oil. Fed Register, 62:30751-30757 (1997).
Vaagenes et al., "The Hypolipidaemic Effect of EPA is Potentiated by 2- and 3-Methylation." in P. Quant & S. Eaton (eds.) Current Views of Fatty Acid Oxidation and Ketogenesis from Organelles to Point Mutations; Advances in Experimental Medicine and Biology, vol. 466 , pp. 221-226 (1999).
Vaddadi, K.S., et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002).
Van der Steeg, W.A., et al., "High-density lipoprotein cholesterol, high-density lipoprotein particle size, and apolipoprotein A-I: Significance for cardiovascular risk the IDEAL and EPIC-Norfolk studies." J. Am. Coll. Cardiol. 51;634-642 (2008).
Varbo et al., Remnant Cholesterol as a Causal Risk Factor for Ischemic Heart Disease, J. Am. Coll. Cardiol., vol. 61(4), pp. 427-436 (2013).
Varbo et al., Remnant cholesterol as a cause of ischemic heart disease: Evidence, definition, measurement, atherogenicity, high risk patients, and present and future treatment, Pharmacol. Ther., vol. 141(3), pp. 358-367 (2014).
Vascepa [package insert], Bedminster, NJ: Amarin Pharma Inc.; 2012.
Vascepa [package insert]. Bedminster, NJ: Amarin Pharma Inc.; 2013.
Vasudevan et al., "Effective Use of Combination of Lipid Therapy", Curr. Atheroscl. Rep., vol. 8, pp. 76-84 (2006).
Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).
Vergnani L, Hatrik S, Ricci F, Passaro A, Manzoli N, Zuliani G, Brovkovych V, Fellin R, Malinski T. Effect of native and oxidized low-density lipoprotein on endothelial nitric oxide and superoxide production : Key role of 1-arginine availability. Circulation. 2000;101:1261-1266.
Vidal F, Colome C, Martinez-Gonzalez J, Badimon L. Atherogenic concentrations of native low density lipoproteins down-regulate nitric-oxide-synthase mma and protein levels in endothelial cells. Eur. J. Biochem. 1998;252:378-384.
Vidgren, H.M., et al., "Incorporation of n-3 fatty acids into plasma lipid fractions, and erythrocyte membranes and platelets during

(56) References Cited

OTHER PUBLICATIONS dietary supplementation with fish, fish oil, and docosahexaenoic acid-rich oil among healthy young men." Lipids 32: 697-705 (1997).

Virani et al., "The Role of Lipoprotein-associated Phospholipase A2 as a marker for atherosclerosis" Curr. Atheroscler. Rep. 9[2]: 97-103 (2007).

Volcik, K.A., et al., "Peroxisome proliferator-activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

Von Schacky C, Baumann K, Angerer P. The effect of n-3 fatty acids on coronary atherosclerosis: results from SCIMO, an angiographic study, background and implications. Lipids 2001 36 Suppl: S99-102.

Von Schacky, C., "A review of omega-3 ethyl esters for cardiovascular prevention and treatment of increased blood triglyceride levels." Vascular Health and Risk Management 2(3): 251-262 (2006).

Von Schacky, C., et al., "The Effect of Dietary ω-3 Fatty Acids on Cornoray Atherosclerosis: A Randomized, Double-Blind, Placebo-Controlled Trial", American College of Physicians—American Society of Internal Medicine, 130(7):554-562, (1999).

Wada, M., et al., "Enzymes and receptors of prostaglandin pathways with arachidonic acid-derived versus eicosapentaenoic acid-derived substrates and products." J. Biol. Chem. 282(31): 22254-22266 (2007).

Wagner AH, Kohler T, Ruckschloss U, Just I, Hecker M. Improvement of nitric oxide-dependent vasodilation by hmg-coa reductase inhibitors through attenuation of endothelial superoxide anion formation. Arterioscler. Thromb. Vasc. Biol. 2000;20:61-69.

Walker G, Mandagere A, Dufton C, et al. The pharmacokinetics and pharmacodynamics of warfarin in combination with ambrisentan in healthy volunteers. Br. J. Clin. Pharmacol. May 2009 67 (5): 527-34.

Walldius, G., et al., "Editorial: Rationale for using apolipoprotein B and apolipoprotein A-I as indicators of cardiac risk and as targets for lipid-lowering therapy." European Heart Journal 26, 210-212 (2005).

Walter MF, Jacob RF, Bjork RE, Jeffers B, Buch J, Mizuno Y, Mason RP. Circulating lipid hydroperoxides predict cardiovascular events in patients with stable coronary artery disease: the PREVENT study. J. Am. Coll. Cardiol. 2008;51(12):1196-1202.

Walter MF, Jacob RF, Jeffers B, Ghadanfar MM, Preston GM, Buch J, Mason RP. Serum levels of TBARS predict cardiovascular events in patients with stable coronary artery disease: A longitudinal analysis of the PREVENT study. J. Am. Coll. Cardiol. 2004;44(10):1996-2002.

Wander, R.C., et al., "Influence of long.chain polyunsaturated fatty acids on oxidation of low density lipoprotein." Prostaglandins, Leukotrienes and Essential Fatty Acids 59(2):143-151 (1998).

Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).

Wang, L., et al., "Triglyceride-rich lipoprotein lipolysis releases neutral and oxidized FFAs that induce endothelial cell inflammation." J. Lipid Res. 50:204-213 (2009).

Warren, Stephen T., "The Expanding World of Trinucleotide Repeats", Science, 271:1374-1375, (1996).

Wassmann S, Laufs U, Muller K, Konkol C, Ahlbory K, Baumer AT, Linz W, Bohm M, Nickenig G. Cellular antioxidant effects of atorvastatin in vitro and in vivo. Arterioscler. Thromb. Vasc. Biol. 2002;22:300-305.

Watanabe, Ikuyoshi, et al., "Usefulness of EPA-E (eicosapentaenoic acid ethyl ester) in preventing neointimal formation after vascular injury", Kokyu to Junkan, 42(7):673-677, (1994).

Weaver, K.L., et al., "Effect of Dietary Fatty Acids on Inflammatory Gene Expression in Healthy Humans." J. Biol. Chem., 284(23): 15400-15407 (2009) (published online Apr. 9, 2009).

Webcast Information for the Oct. 16, 2013 Meeting of the Endocrinologic and Metabolic Drugs Advisory Committee, 1 page.

Weber, P. "Triglyceride-lowering effect of n-3 long chain polyunsaturated fatty acid: eicosapentaenoic acid vs. docosahexaenoic acid." Lipids 34: S269 (1999).

Wei et al., Effects of [EPA] Versus [DHA] on Serum Lipids: A Systematic Review and Meta-Analysis, 13 Current Atherosclerosis Rep. 13(6):474-483 (2011).

Werner, Hypertriglyceridamie: Ein klinischer•Leitfaden, Wissenschaftliche Verlagsgesellschaft mbH Stuttgart, 2008, front page to p. V, pp. 2 to 55, 64 to 85, 90 to 97.

Westerveld H.T. et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993).

Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).

Whelan, J., et al., "Evidence that dietary arachidonic acid increases circulating triglycerides." Lipids 30, 425-429 (1995).

Wierzbicki, A.S., "Editorial: Newer, lower, better? Lipid drugs and cardiovascular disease—the continuing story." Int J Clin Pract, 61(7):1064-1067 (2007).

Wierzbicki, A.S., "Editorial: Raising HDL-C: back to the future?" Int J Clin Pract, 61(7): 1069-1071 (2007).

Willumsen, N. et al., Biochimica et Biophysica Acta. vol. 1369, "On the effect of 2-deuterium- and 2-methyl-eicosapentaenoic acid derivatives on triglycerides, peroxisomal beta-oxidation and platelet aggregation in rats," pp. 193-203, (1998).

Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).

Wilson Omega 3 fish oil: EPA versus DHA (Dietivity.com, 1-16) (2006).

Wilt, VM & Gumm, JG, "Isolated low high-density lipoprotein cholesterol", Ann. Pharmacol., 31:89-97, (1997).

Wink, J., et al., "Effect of very-low-dose niacin on high-density lipoprotein in patients undergoing long-term statin therapy", Am. Heart J., 143:514-518, (2002).

Witztum JL. The oxidation hypothesis of atherosclerosis. Lancet. 1994;344(8925):793-795.

Wojenski, C.M., et al., "Eicosapentaenoic acid ethyl ester as an antithrombotic agent: comparison to an extract of fish oil." Biochimica et Biophysica Acta. 1081:33-38 (1991).

Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).

Woodman et al., "Effects of Purified Eicosapentaenoic and Docosahexaenoic Acids on Glycemic Control, Blood Pressure, and Serum Lipids in Type 2 Diabetic Patients with Treated Hypertension", The American Journal of Clinical Nutrition: Official Journal of the American Society for Clinical Nutrition, Inc., 76(5):1007-1015 (2002).

Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).

Wu, W.H., et al., "Effects of docosahexaenoic acid supplementation on blood lipids, estrogen metabolism, and in vivo oxidative stress in postmenopausal vegetarian women." Eur J Clin Nutr., 60:386-392 (2006).

Xiao, Y.F., et al., "Inhibitory effect of n-3 fish oil fatty acids on cardiac Na+/Ca2+ exchange currents in HEK293t cells." Biochemical and Biophysical Research Communications 321: 116-123 (2004).

(56) References Cited

OTHER PUBLICATIONS

Xiao, Y-F., et al., "Blocking effects of polyunsaturated fatty acids on Na+ channels of neonatal rat ventricular myocytes." Proc. Natl. Acad. Sci. 92: 11000-11004 (1995).
Xiao, Y-F., et al., "Fatty acids suppress voltage-gated Na+ currents in HEK293t cells transfected with the a-subunit of the human cardiac Na+ channel." Proc. Natl. Acad. Sci. 95: 2680-2685 (1998).
Xydakis, A M et al., "Combination therapy for combined dyslipidemia," American Journal of Cardiology, Nov. 20, 2002 US, vol. 90, No. 10 Suppl. 2, p. 21 K-29K (2002).
Yacyshyn BR, Thomson AB. The clinical importance of proton pump inhibitor pharmacokinetics. Digestion 2002 66 (2): 67-78.
Yagi K. Assay for blood plasma or serum. Methods Enzymol. 1984;105:328-331.
Yamamoto, H. et al., Improvement of coronary vasomotion with Eicosapentaenoic acid does not inhibit acetylcholine-induced coronary vasospasm in patients with variant angina: Jpn Cir J. 59(9):608-16 (1995).
Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).
Yamashita et al., J. Biochem., vol. 122, No. 1, "Acyl-transferases and Transaclyases Involved in Fatty Acid Remoding of Phospholipids and Metabolism of Bioactive Lipids in Mammalian Cells", pp. 1-16 (1997).
Yamashita, N., et al., "Inhibition of natural killer cell activity of human lymphocytes by eicosapentaenoic acid." Biochem. Biophys. Res. Comm. 138(3): 1058-1067 (1986).
Yamazaki et al., "Changes in fatty acid composition in rat blood and organs after infusion of eicosapentaenoic acid ethyl ester", Biochim. Biophys. ACTA, 1128(1):3543, (1992).
Yamazaki, et. al., "Dissolution tests by RDC method for soft gelatin capsules containing ethyl icosapentate,", Pharm. Tech. Japan, vol. 15, No. 4, pp. 595-603 Abstract (1999) (with English translation).
Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).
Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi, 115:843-51 (1995).
Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).
Yates RA, Wong J, Seiberling M, et al. The effect of anastrozole on the single-dose pharmacokinetics and anticoagulant activity of warfarin in healthy volunteers. Br. J. Clin. Pharmacol. May 2001 51 (5): 429-35.
Yerram, N.R., et al., "Eicosapentaenoic acid metabolism in brain microvessel endothelium: effect on prostaglandin formation." J. Lipid Res.30:1747-1757 (1989).
Yokoyama et al., "Effects of eicosapentaenoic acid on cardiovascular events in Japanese patients with hypercholesterolemia: Rationale, design, and baseline characteristics of the Japan EPA Lipid Intervention Study (JELIS)," Amer. Heart Journal 146(4):613-620 (2003).
Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).
Yorioka, N, "Lipid-lowering therapy and coagulation/fibrinolysis parameters in patients on peritoneal dialysis," The International Journal of Artificial Organs, vol. 23(1):27-32 2000.
Yoshimura et al., "Effects of highly purified eicosapentaenoic acid on plasma beta thromboglobulin level and vascular reactivity to angiotensin II", Artery, 14(5):295-303, (1987).

Zaima, N., et al., "Trans geometric isomers of EPA decrease LXRa-induced cellular triacylglycerol via suppression of SREBP-1c and PGC-1'?." J. Lipid Res. 47: 2712-2717 (2006).
Zalewski et al., Role of Lipoprotein-Associated Phospholipase A2 in Atherosclerosis: Biology, Epidemiology, and Possible Therapeutic Target, Arteriosclerosis, Thrombosis, & Vascular Biology 25(5):923-931 (2005).
Zanarini, et al., "Omega-3 Fatty Acid Treatment of Women with Borderline Personality Disorder: A Double-Blind, Placebo-Controlled Pilot Study," Am J Psychiatry, 160:167-169 (2003).
Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).
Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).
Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).
Zhao, G. et al., "Dietary ?-linolenic acid inhibits proinflammatory cytokine production by peripheral blood mononuclear cells in hypercholesterolemic subjects." Am J Clin Nutr 85:385-91 (2007).
Zhao, G., et al., "Dietary α-linolenic acid reduces inflammatory and lipid cardiovascular risk factors in hypercholesterolemic men and women." J. Nutr. 134: 2991-2997 (2004).
Ziegler, D., et al., "Treatment of symptomatic diabetic polyneuropathy with the antioxidant ?-lipoic acid: A 7-month multicenter randomized controlled trial (ALADIN III Study)." Diabetes Care 22:1296-1301 (1999).
Zimmerman JJ, Raible DG, Harper DM, et al. Evaluation of a potential tigecycline-warfarin drug interaction. Pharmacotherapy Jul. 2008 28 (7): 895-905.
Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, pp. 89-100 (2000).
Zuijdgeest-van Leeuwen, S.D., et al., "Incorporation and washout of orally administered n-3 fatty acid ethyl esters in different plasma lipid fractions." British Journal of Nutrition 82:481-488 (1999).
Zuijdgeest-van Leeuwen, SD, et al., "Eicosapentaenoic acid inhibits lipolysis in weight-losing cancer patients as well as in healthy volunteers," Eur J Gastroenterol & Hepatol., 10(12):A67 (1998).
Zvyaga T, Chang SY, Chen C, et al. Evaluation of six proton pump inhibitors as inhibitors of various human cytochromes P450: focus on cytochrome P450 2C19. Drug Metab. Dispos. Sep. 2012 40 (9): 1698-711.
Amarin Presentation "Next Generation Lipid Modification in Cardiovascular Disease," (Aug. 2011).
Ascenta Health "Fish Oil as Triglycerides vs. Ethyl Esters: Why this Matters." (2015).
Atovastatin Package Leaflet, Reg. No. LSR-005205/08, Sep. 30, 2016 [retrieved Sep. 30, 2016] retrieved from the internet: academ-clinic.ru/drugs/atorvastatin.
Beaumont et al., Design of Ester Prodrugs to Enhance Oral Absorption of Poorly Permeable Compounds: Challenges to the Discovery Scientist, Current Drug and Metabolism. (2003) 4:461-485.
Bild et at., "Multi-Ethnic Study of Atherosclerosis: objectives and design," Am J Epidemiol 156(9):871-81 (Nov. 1, 2002).
Braeckman et al., "Effect of Concomitant Icosapent Ethyl (Eicosapentaenoic Acid Ethyl Ester) on Pharmacokinetics of Atorvastatin," Clinical Drug Investigation. (2015) (3)45-51.
Carrero, J.J. et al. "Efectos cardiovasculares de los acidos grasos omega-3 y alternativas para incrementar su ingesta," Nutricion Hospitalaria. (2005) (1) 63-69 [with English abstract].
Ceci et al., "The effects of oral 5-hydroxytryptophan administration on feeding behavior in obese adult female subjects," J Neural. Transm (1989) 76:109-117.

(56) References Cited

OTHER PUBLICATIONS

Cromwell et al., "LDL particle number and risk of future cardiovascular disease in the Framingham Offspring Study—Implications for LDL Management," Journal of Lipidololgy. (2009) 1, 583-592.
Davies-Tuck et al., "Total cholesterol and triglycerides are associated with development of new bone marrow lesions in asymptomatic middle-aged women—a prospective cohort study," Arthritis Research & Therapy. (2009) pp. 1-7.
Essentialis Inc. press release, "Essentialis Meets Primary Endpoint in Phase 2b Trial of DCCR for Treatement of Hypertriglyceridemia and is Granted Extensive Patent Coverage in the US," PR Newswire (May 17, 2009).
FDA News Release, "FDA approves new orphan drug Kynamro to treat inherited cholesterol disorder," U.S. Food and Drug Administration, Protecting and Promoting Your Health (Jan. 29, 2013).
Higashihara et al. "Effects of Eicosapentaenoic Acid on Biochemical Failure after Radical Prostatectomy for Prostate Cancer," in vivo 24:561-566 (2010).
Horn et al., "Soft Gelatin Capsules II: Oxygen Permeability Study of Capsule Shells," J Pharm Sci. (1975) 64(5):851-857.
Jong et al., "Role of ApoCs in Lipoprotein Metabolism: Function Differences Between ApoC1, ApoC2, and ApoC3," Arteriosclerosis, Thrombosis and Vascular Biology. (1999) 19(3):472-484.
Kamido et al., Lipid Composition of Platelets from Patients with Atherosclerosis:Effect of Purified Eicosapentaenoic Acid Ethyl Ester Administration, 1988, Lipids, 23, pp. 917-923 [Abstract only].
Kholodov et al., "Clinical Pharmacokinetics," M. Medicine. (1985) pp. 89-98, 134-138, 160, 378-380 [with English Summary].
Labor Diagnostik Karlsruhe, "Target Values of Lipid Metabolism [Recommendation for lipid plasma levels in Germany]," (exact publication date unknown; circa 2006) (with English abstract).
Lada et al., "Associations of Low Density Lipoprotein Particle Compositions with Atherogenicity," Curr. Opin. Lipidol. (2004) 15(1):19-24.
Margolis, Simeon "What is Hyperlipidemia?" (http:www.healthcommunities.com/highcholesterol/whatishyperlipidemia.shtml, accessed Oct. 20, 2015, published Aug. 25, 2011).
Martinez-Gonzalez, Jose et al., "Estatinas y acidos grasos omega-3. Disminucion de la mortalidad cardiovascular dependiente e independiente de la reduccion de la colesterolemia," (2006) Rev Esp Cardiol Suppl., 6(D):20-30 [with English abstract].
Mason et al., "Eicosapentaenoic Acie (EPA) inhibits the formation of membrane cholesterol crystalline domains by a potent antioxidant mechanism," Journ. Clin. Lipid., 7(3): 272-273 (2013) [Abstract only].
Merkl et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, vol. 118, pp. 743-753 (2008).
Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (2007).
O'Riordan, "DHA and EPA have differential effects on LDL-cholsterol," May 24, 2011 [online][Retrieved on Aug. 21, 2015] Retrieved from website: http://www.medscape.com/viewarticle/743305.
Reich, "Formation and physical properties of soft capsules," Pharmaceutical capsules. (2004) Chapter 11:201-212.
Satoh et al., "Highly purified eicosapentaenoic acid reduces cardio-ankle vascular index in association with decreased serum amyloid A-LDL in metabolic syndrome," Hypertension Research (2009) (32):1004-1008.
Sternbach "The Glasgow Como Scale." The Journal of emergency medicine 19.1 (2000): 67-71.
Stiles, FDA approves EPA-only omega-3 PUFA capsule for high TG, http://www.medscape.com/viewarticle/791268, accessed Dec. 17, 2014.
Stojancevic et al., "The impact of farnesoid X receptor activation on intestinal permeability in inflammatory bowel disease," Can. J Gastroenterol. 26(9):631-637 (2012).
Taylor et al., "Fish allergy: fish and products thereof," Journal Food Science (2004) 69.8 R175-R180.
van Wijk et al. Rosiglitazone improves postprandial triglyceride and free fatty acid metabolism in type 2 diabetes. Diabetes Care, vol. 28, No. 4, (2005) pp. 844-849.
Velliquette et al., "Regulation of human stearoyl-CoA desaturase by omega-3 and omega-6 fatty acids: Implications for the dietary management of elevated serum triglycerides," Journal of Clinical Lipdology. (2009) 3:281-288.
Watanabe et al., "Bile acids lower triglyceride levels via a pathway involving FXR, SHP, and SREBP-1c," J Clin Invest. 113(10): 1408-1418 (May 2004).
Wood et al., "Carbohydrate Restriction Alters Lipoprotein Metabolism by Modifying VLDL, LDL and HDL Subraction Distribution and Size in Overweight Men," Journ. of Nutrition, 136(2):384-9 (2006).
Missouri DUReport, Statin Therapy (Oct./Nov. 2003) Drug Use Review Newsletter 8(6):1-9.
Arca et al., "Treating statin-intolerant patients," Diabetes, Metabolic Syndrome and Obesity: Targes and Therapy, 4:155-156 (Apr. 28, 2011) ("Arca").
Asahara, EPA Products What is the Clinical Significance of Epadel? Obesity and Diabetes 10(6):903-905 (2011) (with English translation).
Belikov, Pharmaceutical Chemistry in Two Parts, 1/General Pharmaceutical Chemistry 43-47 (1993) (with English translation).
Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation).
eNews, "Cholesterol Crystals Induce Atherosclerosis-Associated Inflammation in Mice," 1-4 (Jun. 14, 2010).
Epanova® (omega-3-carboxylic acids) capsules, for oral use, Prescribing information, 5 pgs., AstraZeneca Pharmaceuticals LP, (Revised: Mar. 2017).
Futata et al., "Effect of Eicosapentaenoic Acid (EPA) Formulation on Glucose Metabolism in Non-Insulin Dependent Diabetic Patients," Journal of Clinical and Experimental Medicine 169(8):889-890 (May 21, 1994).
Journal of the Japan Diabetes Society, "The Relationship Between Postprandial ApoB48 Increase and Insulin Resistance in Type-2 Diabetes," 55(Suppl. 1):5310 (Apr. 2012) (with English Translation).
Kitada, 9th Diabetes Drug and Drug Related Seminar Diabetes Q&A, Kanazawa Medical University, Diabetes and Endocrine Internal Medicine (Apr. 10, 2011) (with English translation).
Koyama et al., Plaque Reduction and Stabilization Observed in Borderline Diabetes Using Coronary CT Angiogram During Administration of Purified Eicosapentaenoic Acid (EPA) Ther. Res. 31(2):219-225 (2010) (with English translation).
Lawson et al., "Human absorption of fish oil fatty acids as triacyglycerolis, free acids or ethy esters," Biochemical and Biophysical Research Communications 152(1):328-335 (Apr. 15, 1988).
Mason et al., "Direct evidence for cholesterol crystalline domains in biological membranes: role in human pathobiology," Biochimica et Biophysica Acta 198-207 (2003).
Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005).
Sugiyama et al., "A Comparison of the Hypotensive Effects of Eicosapentaenoic Acid Ethyl (EPA) on Three Diseases (Occluded Arteriosclerosis, Hyperlipemia, and These Two Diseases Combined) P2-504 Abstract," Annual Meeting of the Japanese Society of Pharmaceutical Health Care and Sciences 20:473 (2010) (with English translation).
Williams et al., "NADPH Oxidase Inhibitors New Antihypertensive Agents?" J. Cardiovasc Pharmacol 50(1):9-16 (Jul. 1, 2007).

(56) References Cited

OTHER PUBLICATIONS

Avery et al., "Upper Gastrointestinal System," Integrating Therapeutic and Complementary Nutrition, Edited by Mary Marian, CRC Press (2006).
Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008).
Center for Drug Evaluation and Research. Approval Package for Application No. 202057Orig1s000. Review—Vascepa (formerly AMR101), 373 pages (Jul. 26, 2012).
Crevel et al., "Allergenicity of Refined Vegetable Oils," Food and Chemical Toxicology, 38, pp. 385-393 (2000).
Eilat-Adar et al. "Association of Intentional Changes in Body Weight with Coronary Heart Disease Event Rates in Overweight Subjects who have an Additional Coronary Risk Factor," Amer. Journ. Epidemiol.161(4) (Sep. 9, 2004).
Leaf, "Hypertriglyceridemia: A Guide to Assessment and Treatment," Hospital Physician 17-32 (Sep. 2008).
MedlinePlus. "Coronary heart disease," Available at: https://medlineplus.gov/ency/article/007115.htm (accessed Sep. 2, 2016).
Sicherer et al., "Prevalence of seafood allergy in the United States determined by a random telephone survey," J. Allergy Clin. Immunol., 114(1):159-165 (Jul. 2004).

\* cited by examiner

COMPOSITIONS AND METHODS FOR LOWERING LEVELS OF HIGH-SENSITIVITY C-REACTIVE PROTEIN (HS-CRP) IN A SUBJECT

PRIORITY CLAIM

This application claims priority to U.S. provisional application Ser. No. 61/584,013, filed Jan. 6, 2012, U.S. provisional application Ser. No. 61/656,347, filed Jun. 6, 2012, and U.S. provisional application Ser. No. 61/670,408, filed Jul. 11, 2012, each of which are incorporated by reference herein in their entireties.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke.

SUMMARY

The present disclosure generally provides pharmaceutical compositions comprising EPA or derivative thereof (e.g., ethyl-EPA) and uses of such compositions in methods for lowering high sensitivity CRP (hs-CRP) levels in a subject including, for example, a subject with a hemoglobin A1c ($HbA_{1c}$) value greater of about 4.90%-9.50%, or at least about 6.8%. Such compositions may be useful in the treatment of diseases or disorders characterized by an increased/elevated level of hs-CRP (e.g., inflammatory or cardiovascular diseases or disorders).

In various embodiments, the present disclosure provides methods of lowering high-sensitivity CRP (hs-CRP) levels in a subject with a $HbA_{1c}$ value of about 4.90% to about 9.50%, or at least about 6.8%, by administering to the subject about 1 g to about 4 g per day of a pharmaceutical composition comprising at least about 70%, at least about 80%, at least about 90%, at least about 95%, at least about 96%, at least about 97%, at least about 98%, or at least about 99%, by weight of all fatty acids present, eicosapentaenoic acid or a derivative thereof (e.g., ethyl eicosapentaenoate for a period of time (e.g., about 12 weeks) effective to hs-CRP levels in the subject compared to baseline or placebo control.

In one embodiment, which may be used or combined with any of the above or below mentioned embodiments, the disclosure provides a method of lowering high-sensitivity CRP (hs-CRP) in a subject in need thereof, the method comprising: administering to the subject a pharmaceutical composition comprising about 3 g to about 5 g (e.g. about 4 g) of EPA or derivative thereof per day for a period of time effective to lower hs-CRP. Optionally, the subject is on concomitant statin or stable statin therapy.

In one embodiment, which may be used or combined with any of the above or below mentioned embodiments, upon administering the composition to the subject daily for a period of 12 weeks and maintaining a placebo controlled subject on stable statin therapy without concomitant EPA therapy for a period of 12 weeks, the subject exhibits at least 5% lower, at least 10% lower, at least 15% lower, at least 20% lower, or at least 25% lower, hs-CRP levels than the placebo controlled subject. In one embodiment, the placebo controlled subject has a $HbA_{1c}$ value greater of about 5.00%-8.50%, or at least about 6.8%.

In various embodiments, the present invention provides methods of treating and/or preventing cardiovascular-related diseases and, in particular, a method of blood lipid therapy comprising administering to a subject in need thereof a pharmaceutical composition comprising eicosapentaenoic acid or a derivative thereof. In one embodiment, the composition contains not more than about 10%, not more than about 5% or not more than 3%, by weight of fatty acids, docosahexaenoic acid or derivative thereof (e.g. esters), substantially no docosahexaenoic acid or derivative thereof, or no docosahexaenoic acid or derivative thereof. In another embodiment, eicosapentaenoic acid ethyl ester comprises at least about 95%, by weight, of all fatty acids present in the composition; the composition contains not more than 4%, by weight, of total fatty acids other than eicosapentaenoic acid ethyl ester; and/or the composition contains about 0.1% to about 0.6% of at least one fatty acid other than eicosapentaenoic acid ethyl ester and docosahexaenoic acid (or derivative thereof).

In one embodiment, a pharmaceutical composition useful in accordance with the invention comprises, consists of or consists essentially of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In another embodiment, the composition contains substantially no or no amount of docosahexaenoic acid (DHA) or derivative thereof such as ethyl-DHA (DHA-E).

In another embodiment, the invention provides a method of treating moderate to severe hypertriglyceridemia comprising administering a composition as described herein to a subject in need thereof one to about four times per day.

In one embodiment, which may be used or combined with any of the above or below mentioned embodiments, the subject and/or the placebo controlled subject have baseline triglycerides of about 150-499 mg/dl.

In one embodiment, which may be used or combined with any of the above or below mentioned embodiments, the subject is on stable statin therapy.

In one embodiment, which may be used or combined with any of the above or below mentioned embodiments, the pharmaceutical composition comprises at least 96% by weight of fatty acids, ethyl eicosapentaenoate.

In one embodiment, which may be used or combined with any of the above or below mentioned embodiments, the pharmaceutical composition comprises substantially no DHA or derivative thereof.

In one embodiment, which may be used or combined with any of the above or below mentioned embodiments, the pharmaceutical composition is encapsulated in a capsule.

In one embodiment, which may be used or combined with any of the above or below mentioned embodiments, the capsule comprises gelatin.

In one embodiment, which may be used or combined with any of the above or below mentioned embodiments, 1 to 4 capsules are administered to the subject each day.

In one embodiment, which may be used or combined with any of the above or below mentioned embodiments, the statin is selected from the group consisting of lovastatin, mevastatin, pitavastatin, pravastatin, rosuvastatin, fluvastatin, atorvastatin and simvastatin.

In one embodiment, which may be used or combined with any of the above or below mentioned embodiments, the subject and the placebo controlled subject have a baseline body mass index not greater than 45 kg/m$^2$.

In one embodiment, which may be used or combined with any of the above or below mentioned embodiments, the subject and/or the placebo controlled subject is not on concomitant niacin or fibrate therapy.

In one embodiment, which may be used or combined with any of the above or below mentioned embodiments, the subject has a baseline sitting systolic blood pressure less than or equal to about 160 mmHg and a baseline sitting diastolic blood pressure less than about 100 mmHg.

In one embodiment, which may be used or combined with any of the above or below mentioned embodiments, the pharmaceutical composition contains substantially no ethyl-DHA.

In various embodiments, the present disclosure also provides methods of lowering high-sensitivity CRP (hs-CRP) levels in a subject on stable statin therapy with a HbA$_{1c}$ value greater of about 4.90% to 9.50% or at least about 6.8%, and baseline triglycerides of about 150-499 mg/dl by administering to the subject a pharmaceutical composition comprising about 1 to about 4 g of EPA or derivative thereof per day, wherein upon administering the composition to the subject daily for a period of about 12 weeks the subject exhibits a reduction in hs-CRP level compared to a baseline hs-CRP level prior to initial administration of the pharmaceutical composition.

In various embodiments, the present disclosure also provides methods of treating a subject to lower high-sensitivity CRP (hs-CRP) levels in the subject by selecting a subject with a HbA$_{1c}$ value of about 4.90%-9.50% or at least about 6.8%; and administering to the subject a pharmaceutical composition comprising about 1 to about 4 g of EPA or derivative thereof per day, wherein upon administering the composition to the subject daily for a period of about 12 weeks the subject exhibits a reduction in hs-CRP level compared to a baseline hs-CRP level prior to initial administration of the pharmaceutical composition.

In one embodiment, which may be used or combined with any of the above or below mentioned embodiments, the subject exhibits at least a 5%, 10%, 15%, 20%, or 25% lowering of hs-CRP levels compared to a placebo controlled subject on stable statin therapy with a HbA$_{1c}$ value greater than or equal to about 5.00-8.50% and baseline triglycerides of about 150-499 mg/dl but not on concomitant EPA therapy. In an embodiment, the placebo controlled subject has a HbA$_{1c}$ value greater than or equal to about 6.8%.

In one embodiment, which may be used or combined with any of the above or below mentioned embodiments, the subject and/or the placebo controlled subject have baseline triglycerides of about 150-499 mg/dl.

In one embodiment, which may be used or combined with any of the above or below mentioned embodiments, the subject and/or the placebo controlled subject is on a stable statin therapy.

In one embodiment, which may be used or combined with any of the above or below mentioned embodiments, the pharmaceutical composition comprises at least 90%, by weight of all fatty acids, ethyl eicosapentaenoate and substantially no DHA or derivative thereof.

In one embodiment, which may be used or combined with any of the above or below mentioned embodiments, the pharmaceutical composition comprises at least 95%, by weight ethyl of all fatty acids, eicosapentaenoate and substantially no ethyl-DHA.

In one embodiment, which may be used or combined with any of the above or below mentioned embodiments, the pharmaceutical composition is encapsulated in a capsule.

In one embodiment, which may be used or combined with any of the above or below mentioned embodiments, 1 to 4 capsules are administered to the subject each day, In one embodiment, which may be used or combined with any of the above or below mentioned embodiments, the statin is selected from the group consisting of lovastatin, mevastatin, pitavastatin, pravastatin, rosuvastatin, fluvastatin, atorvastatin and simvastatin.

In one embodiment, which may be used or combined with any of the above or below mentioned embodiments, the subject and the placebo controlled subject have a baseline body mass index not greater than 45 kg/m$^2$.

In one embodiment, which may be used or combined with any of the above or below mentioned embodiments, the subject and/or the placebo controlled subject is not on concomitant niacin or fibrate therapy.

In one embodiment, which may be used or combined with any of the above or below mentioned embodiments, the subject and the placebo controlled subject have a baseline sitting systolic blood pressure less than or equal to about 160 mmHg and a baseline sitting diastolic blood pressure less than about 100 mmHg.

These and other embodiments of the present invention will be disclosed in further detail herein below.

BRIEF DESCRIPTION OF THE DRAWINGS

The foregoing summary, as well as the following detailed description of the disclosure, will be better understood when read in conjunction with the appended figures. It should be understood, however, that the disclosure is not limited to the precise arrangements, examples and instrumentalities shown.

DETAILED DESCRIPTION

Figure 1:
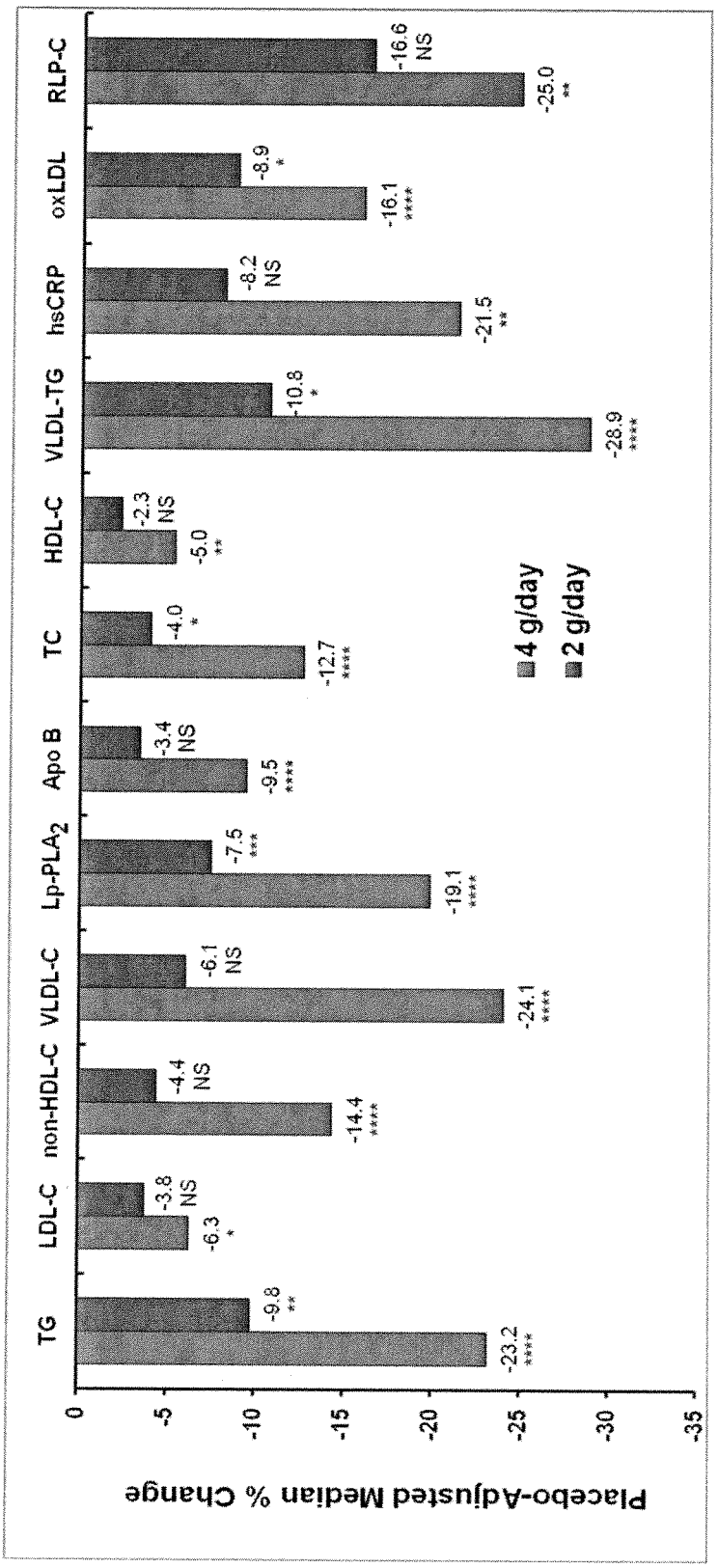
FIG. 1 shows a graphical depiction of the placebo-adjusted median percent change in levels of triglyceride (TG), low-density lipoprotein cholesterol (LDL-C), non-high-density lipoprotein cholesterol (non-HDL-C), very low-density lipoprotein cholesterol (VLDL-C), lipoprotein-associated phospholipase A2 (Lp-PLA$_2$), apolipoprotein B (Apo B), total cholesterol (TC), high-density lipoprotein cholesterol (HDL-C), very low-density lipoprotein-TG (VLDL-TG), high-sensitivity C-reactive protein (hs-CRP), oxidized low-density lipoprotein (oxLDL), and remnant-like particle cholesterol (RLP-C) in subjects with diabetes treated with 2 g/day or 4 g/day ultra-pure EPA for 12 weeks.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

In one embodiment, the present invention provides methods of treating or preventing a disease or disorder in a subject in need thereof including, for example, a subject with a HbA$_{1c}$ value of about 4.9 to about 10, for example greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50%, by administering a composition comprising EPA or derivative thereof to the subject, wherein the disease or disorder is characterized by an increased/elevated level of hs-CRP. In one embodiment, the subject has a HbA$_{1c}$ value greater than or equal to 6.8%. In related embodiments, the disease or disorder is a cardiovascular related disease or disorder.

In one embodiment, the invention provides a method for treatment and/or prevention of a cardiovascular-related disease. The term "cardiovascular-related disease" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

In some embodiments, a disease or disorder is characterized by an increased level of hs-CRP when the level of hs-CRP in a subject with the disease or disorder is increased/elevated as compared to the level of hs-CRP in a subject without the disease or disorder. Alternatively, a disease or disorder is characterized by an increased level of hs-CRP when the level of hs-CRP in a subject with the disease or disorder is elevated as compared to a control sample, or a baseline or threshold. In some embodiments, a disease or disorder is characterized by an increased level of hs-CRP when the level of hs-CRP in a subject with the disease or disorder is 5%, 10%, 15%, 20%, 25%, 30%, 35%, 40%, 45%, 50%, 55%, 60%, 65%, 70%, 75%, 80%, 85%, 90%, 95%, 100% or more, greater than the level of hs-CRP in a subject or subjects (mean or median) without the disease or disorder. In some embodiments, a disease or disorder is characterized by an increased level of hs-CRP when the level of hs-CRP in a subject with the disease or disorder is 5%, 10%, 15%, 20%, 25%, 30%, 35%, 40%, 45%, 50%, 55%, 60%, 65%, 70%, 75%, 80%, 85%, 90%, 95%, 100% or more, greater than the level of hs-CRP in a control sample (mean or median), or a baseline or threshold value. A baseline or a threshold value as provided herein may be an average or median obtained from two or more subjects.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides methods of blood lipid therapy comprising administering to a subject or subject group in need thereof including, for example, a subject or a subject group with a $HbA_{1c}$ value greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50% (or mean or median $HbA_{1c}$ value in the case of a subject group), a pharmaceutical composition as described herein. In one embodiment, the subject or the subject group has a $HbA_{1c}$ value greater than or equal to about 6.8%. In another embodiment, the subject or subject group has hypertriglyceridemia, hypercholesterolemia, mixed dyslipidemia and/or very high triglycerides.

In another embodiment, the subject or subject group being treated has a baseline triglyceride level (or mean or median baseline triglyceride level in the case of a subject group), fed or fasting, of about 150 mg/dl to about 499 mg/dl. In one embodiment, the subject or the subject group has a $HbA_{1c}$ value greater than or equal to 6.8%. In another embodiment, the subject or subject group has a baseline LDL-C level (or mean or median baseline LDL-C level), despite stable statin therapy, of about 40 mg/dl to about 115 or about 40 to about 100 mg/dl.

In one embodiment, the subject or subject group being treated in accordance with methods of the invention is on concomitant statin therapy, for example atorvastatin, rosuvastatin or simvastatin therapy (with or without ezetimibe). In another embodiment, the subject is on concomitant stable statin therapy at time of initiation of EPA therapy.

In another embodiment, the subject or subject group being treated in accordance with methods of the invention has a body mass index (BMI or mean BMI) of not more than about 45 kg/m².

In one embodiment, the present disclosure provides methods of lowering high-sensitivity CRP (hs-CRP) levels in a subject with a $HbA_{1c}$ value greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50% by administering to the subject a pharmaceutical composition comprising about 1 g to about 4 g of EPA (e.g. high purity or ultra-pure EPA) per day, wherein upon administering the composition to the subject daily for a period of about 12 weeks the subject exhibits a reduction in hs-CRP. In one embodiment, the subject has a $HbA_{1c}$ value greater than or equal to 6.8%. In an embodiment, the subject has baseline triglycerides of about 150-499 mg/dl. In another embodiment, the subject is on statin therapy, for example stable statin therapy. In yet another embodiment, upon administering the composition to the subject daily for a period of 12 weeks and maintaining a placebo controlled subject on stable statin therapy without concomitant EPA therapy for a period of 12 weeks, the subject exhibits at least 5% lower, at least 10% lower, at least 15% lower, at least 20% lower, at least 25% lower, at least 30% lower, at least 35% lower, at least 40% lower, at least 50% lower, at least 55% lower, at least 60% lower, at least 65% lower, at least 70% lower, or at least 75% lower hs-CRP levels than the placebo controlled subject.

In another embodiment, the present disclosure also provides methods of lowering high-sensitivity CRP (hs-CRP) levels in a subject on stable statin therapy with a $HbA_{1c}$ value greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50% and baseline triglycerides of about 150-499 mg/dl by administering to the subject a pharmaceutical composition comprising about 1 g to about 4 g of EPA (e.g. ultra-pure EPA) per day, wherein upon administering the composition to the subject daily for a period of about 12 weeks the subject exhibits a reduction in hs-CRP compared to a baseline hs-CRP level prior to initial administration of the pharmaceutical composition. In one embodiment, the subject has a $HbA_{1c}$ value greater than or equal to 6.8%. In an embodiment, the subject has baseline triglycerides of about 150-499 mg/dl. In another embodiment, the subject is on statin or stable statin therapy.

In another embodiment, the present disclosure also provides methods of treating a subject to lower high-sensitivity CRP (hs-CRP) levels in the subject by selecting a subject with a $HbA_{1c}$ value greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50%; and administering to the subject a pharmaceutical composition comprising about 1 g to about 4 g of EPA (e.g. ultra-pure EPA) per day, wherein upon administering the composition to the subject daily for a period of about 12 weeks the subject exhibits a reduction in hs-CRP compared to a baseline hs-CRP level prior to initial administration of the pharmaceutical composition. In one embodiment, the subject has a $HbA_{1c}$ value greater than or equal to 6.8%. In an embodiment, the subject has baseline triglycerides of about 150-499 mg/dl. In another embodiment, the subject is on stable statin therapy.

The term "stable statin therapy" herein means that the subject, subject group, control subject or control subject group in question has been taking a stable daily dose of a statin (e.g. atorvastatin, rosuvastatin or simvastatin) for at least 4 weeks prior to the baseline fasting triglyceride measurement (the "qualifying period"). For example, a subject or control subject on stable statin therapy would receive a constant daily (i.e. the same dose each day) statin dose for at least 4 weeks immediately prior to baseline fasting triglyceride measurement. In one embodiment, the subject's and control subject's LDL-C is maintained between about 40 mg/dl and about 115 mg/dl or about 40 mg/dl to about 100 mg/dl during the qualifying period. The subject and control subject are then continued on their stable statin dose for the 12 week period post baseline.

In one embodiment, the statin is administered to the subject and the control subject in an amount of about 1 mg to about 500 mg, about 5 mg to about 200 mg, or about 10 mg to about 100 mg, for example about 1 mg, about 2 mg, about 3 mg, about 4 mg, about 5 mg, about 6 mg, about 7 mg, about 8 mg, about 9 mg, or about 10 mg; about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In another embodiment, the subject (and optionally the control subject) has a baseline LDL-C level, despite stable statin therapy, of about 40 mg/dl to about 115 mg/dl or about 40 mg/dl to about 100 mg/dl. In another embodiment, the subject and/or control subject has a body mass index (BMI; or mean BMI) of not more than about 45 kg/m$^2$.

In another embodiment, the subject or subject group being treated in accordance with methods of the invention exhibits a fasting baseline absolute plasma level of free total fatty acid (or mean thereof) not greater than about 300 nmol/ml, not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of free EPA (or mean thereof) not greater than about 1 nmol/ml, not greater than about 0.75 nmol/ml, not greater than about 0.50 nmol/ml, not greater than about 0.4 nmol/ml, not greater than about 0.35 nmol/ml, or not greater than about 0.30 nmol/ml.

In another embodiment, the subject or subject group being treated in accordance with methods of the invention exhibits a fasting baseline plasma, serum or red blood cell membrane EPA level not greater than about 150 µg/ml, not greater than about 125 µg/ml, not greater than about 100 µg/ml, not greater than about 95 µg/ml, not greater than about 75 µg/ml, not greater than about 60 µg/ml, not greater than about 50 µg/ml, not greater than about 40 µg/ml, not greater than about 30 µg/ml, or not greater than about 25 µg/ml.

In another embodiment, methods of the present invention comprise a step of measuring the subject's (or subject group's mean or median) baseline lipid profile prior to initiating therapy. In another embodiment, methods of the invention comprise the step of identifying a subject or subject group having one or more of the following: baseline non-HDL-C value (or mean) of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value (or mean) of about 250 mg/dl to about 400 mg/dl, for example at least about 260 mg/dl, at least about 270 mg/dl, at least about 280 mg/dl or at least about 290 mg/dl; baseline vLDL-C value (or mean) of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value (or mean) of about 10 to about 100 mg/dl, for example not more than about 90 mg/dl not, not more than about 80 mg/dl, not more than about 70 mg/dl, not more than about 60 mg/dl, not more than about 60 mg/dl, not more than about 50 mg/dl, not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value (or mean) of about 30 to about 300 mg/dl, for example not less than about 40 mg/dl, not less than about 50 mg/dl, not less than about 60 mg/dl, not less than about 70 mg/dl, not less than about 90 mg/dl or not less than about 90 mg/dl.

In one embodiment, the present invention provides a method of blood lipid therapy comprising administering to a subject or subject group in need thereof a pharmaceutical composition as described herein. In another embodiment, the subject or subject group has hypertriglyceridemia, hypercholesterolemia, mixed dyslipidemia and/or very high triglycerides.

In another embodiment, the subject or subject group being treated has a baseline triglyceride level (or median baseline triglyceride level in the case of a subject group), fed or fasting, of at least about 135 mg/dl, at least about 150 mg/dl, at least about 200 mg/dl, at least about 300 mg/dl, at least about 400 mg/dl, at least about 500 mg/dl, at least about 600 mg/dl, at least about 700 mg/dl, at least about 800 mg/dl, at least about 900 mg/dl, at least about 1000 mg/dl, at least about 1100 mg/dl, at least about 1200 mg/dl, at least about 1300 mg/dl, at least about 1400 mg/dl, or at least about 1500 mg/dl, for example about 400 mg/dl to about 2500 mg/dl, about 450 mg/dl to about 2000 mg/dl or about 500 mg/dl to about 1500 mg/dl. In some embodiments, a subject group being treated has a median baseline triglyceride level of about 680 mg/dl, about 656 mg/dl, about 703 mg/dl, about 265 mg/dl, about 254 mg/dl, or about 259 mg/dl.

In another embodiment, the subject or subject group being treated has a baseline LDL-C level (or median baseline LDL-C level in the case of a subject group), fed or fasting, of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl. In some embodiments, the subject group being treated has a baseline LDL-C level (or median baseline LDL-C level in the case of a subject group), fed or fasting, of 90 mg/dl, about 84 mg/dl, about 86 mg/dl, or about 82 mg/dl.

In another embodiment, the subject or subject group being treated has a baseline non-HDL-C level (or a mean or median baseline non-HDL-C level in the case of a subject group), fed or fasting, of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl. In some embodiments, the subject or subject group being treated has a baseline non-HDL-C level (or a mean or median baseline non-HDL-C level in the case of a subject group), fed or fasting, of about 225 mg/dl, about 210 mg/dl, about 229 mg/dl, or about 128 mg/dl.

In another embodiment, the subject or subject group being treated has a baseline total cholesterol level (or a mean or median baseline total cholesterol level in the case of a subject group), fed or fasting, of about 150 mg/dl to about 400 mg/dl, for example at least about 150 mg/dl, at least about 160 mg/dl, at least about 170 mg/dl, at least about 180 mg/dl, at least about 190 mg/dl, at least about 200 mg/dl, at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl 300 mg/dl, at least about 310 mg/dl, at least about 320 mg/dl, at least about 330 mg/dl, at least about 340 mg/dl, at least about 350 mg/dl, at least about 360 mg/dl, at least about 370 mg/dl, at least about 380 mg/dl, at least about 390 mg/dl, or about 400 mg/dl. In some embodiments, the subject or subject group being treated has a baseline total cholesterol level (or a mean or median baseline total cholesterol level in the case of a subject group), fed or fasting, of about 253 mg/dl, about 236 mg/dl, about 256 mg/dl, about 167 mg/dl, about 169 mg/dl, or about 168 mg/dl.

In another embodiment, the subject or subject group being treated has a baseline HDL-C level (or a mean or median baseline HDL-C level in the case of a subject group), fed or fasting, of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl. In some embodiments, the subject or subject group being treated has a baseline HDL-C level (or a mean or median baseline HDL-C level in the case of a subject group), fed or fasting, of about 26.5 mg/dl, about 26 mg/dl, about 27 mg/dl, about 37 mg/dl, about 38 mg/dl, or about 39 mg/dl.

In another embodiment, the subject or subject group being treated has a baseline lipid profile comprising: (a) a baseline (or median baseline) triglyceride level of about 680 mg/dl, (b) a baseline (or median baseline) LDL-C level of about 90 mg/dl, (c) a baseline (or median baseline) non-HDL-C level of about 225 mg/dl, (d) a baseline (or median baseline) total cholesterol level of about 254 mg/dl, and (e) a baseline (or median baseline) HDL-C level of about 26.5 mg/dl. In another embodiment, the subject or subject group being treated has a baseline lipid profile comprising: (a) a baseline (or median baseline) triglyceride level of about 656 mg/dl, (b) a baseline (or median baseline) LDL-C level of about 84 mg/dl, (c) a baseline (or median baseline) non-HDL-C level of about 210 mg/dl, (d) a baseline (or median baseline) total cholesterol level of about 236 mg/dl, and (e) a baseline (or median baseline) HDL-C level of about 26 mg/dl. In another embodiment, the subject or subject group being treated has a baseline lipid profile comprising: (a) a baseline (or median baseline) triglyceride level of about 703 mg/dl, (b) a baseline (or median baseline) LDL-C level of about 86 mg/dl, (c) a baseline (or median baseline) non-HDL-C level of about 229 mg/dl, (d) a baseline (or median baseline) total cholesterol level of about 256 mg/dl, and (e) a baseline (or median baseline) HDL-C level of about 27 mg/dl. In another embodiment, the subject or subject group being treated has a baseline lipid profile comprising: (a) a baseline (or median baseline) triglyceride level of about 265 mg/dl, (b) a baseline (or median baseline) LDL-C level of about 82 mg/dl, (c) a baseline (or median baseline) non-HDL-C level of about 128 mg/dl, (d) a baseline (or median baseline) total cholesterol level of about 167 mg/dl, and (e) a baseline (or median baseline) HDL-C level of about 37 mg/dl. In another embodiment, the subject or subject group being treated has a baseline lipid profile comprising: (a) a baseline (or median baseline) triglyceride level of about 254 mg/dl, (b) a baseline (or median baseline) LDL-C level of about 82 mg/dl, (c) a baseline (or median baseline) non-HDL-C level of about 128 mg/dl, (d) a baseline (or median baseline) total cholesterol level of about 169 mg/dl, and (e) a baseline (or median baseline) HDL-C level of about 38 mg/dl. In another embodiment, the subject or subject group being treated has a baseline lipid profile comprising: (a) a baseline (or median baseline) triglyceride level of about 259 mg/dl, (b) a baseline (or median baseline) LDL-C level of about 84 mg/dl, (c) a baseline (or median baseline) non-HDL-C level of about 128 mg/dl, (d) a baseline (or median baseline) total cholesterol level of about 168 mg/dl, and (e) a baseline (or median baseline) HDL-C level of about 39 mg/dl.

In another embodiment, the subject or subject group being treated has baseline levels (or mean or median baseline levels in the case of a subject group), fed or fasting, of one or more inflammatory markers, for example ICAM-1, ox-LDL, Lp-PLA$_2$, IL-6, and/or hsCRP. In some embodiments, the subject or subject group being treated has a baseline ICAM-1 level (or mean or median baseline ICAM-1 level in the case of a subject group), fed or fasting, of about 200 to about 300 ng/ml, for example about 200 ng/ml, about 205 ng/ml, about 210 ng/ml, about 215 ng/ml, about 220 ng/ml, about 225 ng/ml, about 230 ng/ml, about 235 ng/ml, about 240 ng/ml, about 245 ng/ml, about 250 ng/ml, about 255 ng/ml, about 260 ng/ml, about 265 ng/ml, about 270 ng/ml, about 275 ng/ml, about 280 ng/ml, about 285 ng/ml, about 290 ng/ml, about 295 ng/ml, or about 300 ng/ml. In some embodiments, the subject or subject group being treated has a baseline ICAM-1 level (or mean or median baseline ICAM-1 level in the case of a subject group), fed or fasting, of about 250 ng/ml, about 256 ng/ml, about 248 ng/ml, about 273 ng/ml, about 267 ng/ml, or about 269 ng/ml.

In another embodiment, the subject or subject group being treated has a baseline ox-LDL level (or a mean or median baseline ox-LDL level in the case of a subject group), fed or fasting, of about 20 to about 100 U/L, for example about 20 U/L, about 25 U/L, about 30 U/L, about 35 U/L, about 40 U/L, about 45 U/L, about 50 U/L, about 55 U/L, about 60 U/L, about 65 U/L, about 70 U/L, about 75 U/L, about 80

U/L, about 85 U/L, about 90 U/L, about 95 U/L, or about 100 U/L. In some embodiments, the subject or subject group being treated has a baseline ox-LDL level (or mean or median baseline ox-LDL level in the case of a subject group), fed or fasting, of about 79 U/L, about 76 U/L, about 74 U/L, about 54 U/L, or about 52 U/L.

In another embodiment, the subject or subject group being treated has a baseline Lp-PLA$_2$ level (or a mean or median baseline Lp-PLA$_2$ level in the case of a subject group), fed or fasting, of about 150 ng/ml to about 300 ng/ml, for example about 150 ng/ml, about 155 ng/ml, about 160 ng/ml, about 165 ng/ml, about 170 ng/ml, about 175 ng/ml, about 180 ng/ml, about 185 ng/ml, about 190 ng/ml, about 195 ng/ml, about 200 ng/ml, about 205 ng/ml, about 210 ng/ml, about 215 ng/ml, about 220 ng/ml, about 225 ng/ml, about 230 ng/ml, about 235 ng/ml, about 240 ng/ml, about 245 ng/ml, about 250 ng/ml, about 255 ng/ml, about 260 ng/ml, about 265 ng/ml, about 270 ng/ml, about 275 ng/ml, about 280 ng/ml, about 285 ng/ml, about 290 ng/ml, about 295 ng/ml, or about 300 ng/ml. In some embodiments, the subject or subject group being treated has a baseline Lp-PLA$_2$ level (or a mean or median baseline Lp-PLA$_2$ level in the case of a subject group), fed or fasting, of about 246 ng/ml, about 235 ng/ml, about 253 ng/ml, about 180 ng/ml, about 190 ng/ml, or about 195 ng/ml.

In another embodiment, the subject or subject group being treated has a baseline IL-6 level (or a mean or median baseline IL-6 level in the case of a subject group), fed or fasting, of about 0.1 pg/ml to about 10 pg/ml, for example about 0.1 pg/ml, about 0.2 pg/ml, about 0.3 pg/ml, about 0.4 pg/ml, about 0.5 pg/ml, about 0.6 pg/ml, about 0.7 pg/ml, about 0.8 pg/ml, about 0.9 pg/ml, about 1 pg/ml, about 1.1 pg/ml, about 1.2 pg/ml, about 1.3 pg/ml, about 1.4 pg/ml, about 1.5 pg/ml, about 1.6 pg/ml, about 1.7 pg/ml, about 1.8 pg/ml, about 1.9 pg/ml, about 2 pg/ml, about 2.1 pg/ml, about 2.2 pg/ml, about 2.3 pg/ml, about 2.4 pg/ml, about 2.5 pg/ml, about 2.6 pg/ml, about 2.7 pg/ml, about 2.8 pg/ml, about 2.9 pg/ml, about 3 pg/ml, about 3.1 pg/ml, about 3.2 pg/ml, about 3.3 pg/ml, about 3.4 pg/ml, about 3.5 pg/ml, about 3.6 pg/ml, about 3.7 pg/ml, about 3.8 pg/ml, about 3.9 pg/ml, about 4 pg/ml, about 4.1 pg/ml, about 4.2 pg/ml, about 4.3 pg/ml, about 4.4 pg/ml, about 4.5 pg/ml, about 4.6 pg/ml, about 4.7 pg/ml, about 4.8 pg/ml, about 4.9 pg/ml, about 5 pg/ml, about 5.1 pg/ml, about 5.2 pg/ml, about 5.3 pg/ml, about 5.4 pg/ml, about 5.5 pg/ml, about 5.6 pg/ml, about 5.7 pg/ml, about 5.8 pg/ml, about 5.9 pg/ml, about 6 pg/ml, about 6.1 pg/ml, about 6.2 pg/ml, about 6.3 pg/ml, about 6.4 pg/ml, about 6.5 pg/ml, about 6.6 pg/ml, about 6.7 pg/ml, about 6.8 pg/ml, about 6.9 pg/ml, about 7 pg/ml, about 7.1 pg/ml, about 7.2 pg/ml, about 7.3 pg/ml, about 7.4 pg/ml, about 7.5 pg/ml, about 7.6 pg/ml, about 7.7 pg/ml, about 7.8 pg/ml, about 7.9 pg/ml, about 8 pg/ml, about 8.1 pg/ml, about 8.2 pg/ml, about 8.3 pg/ml, about 8.4 pg/ml, about 8.5 pg/ml, about 8.6 pg/ml, about 8.7 pg/ml, about 8.8 pg/ml, about 8.9 pg/ml, about 9 pg/ml, about 9.1 pg/ml, about 9.2 pg/ml, about 9.3 pg/ml, about 9.4 pg/ml, about 9.5 pg/ml, about 9.6 pg/ml, about 9.7 pg/ml, about 9.8 pg/ml, about 9.9 pg/ml, or about 10 pg/ml. In some embodiments, the subject or subject group being treated has a baseline IL-6 level (or a mean or median baseline IL-6 level in the case of a subject group), fed or fasting, of about 2.3 pg/ml, about 3 pg/ml, about 2.5 pg/ml, about 2.7 pg/ml, about 2.4 pg/ml, or about 3.2 pg/ml.

In another embodiment, the subject or subject group being treated has a baseline hsCRP level (or a mean or median baseline hsCRP level in the case of a subject group), fed or fasting, of about 0.1 mg/L to about 10 mg/L, for example about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1 mg/L, about 1.1 mg/L, about 1.2 mg/L, about 1.3 mg/L, about 1.4 mg/L, about 1.5 mg/L, about 1.6 mg/L, about 1.7 mg/L, about 1.8 mg/L, about 1.9 mg/L, about 2 mg/L, about 2.1 mg/L, about 2.2 mg/L, about 2.3 mg/L, about 2.4 mg/L, about 2.5 mg/L, about 2.6 mg/L, about 2.7 mg/L, about 2.8 mg/L, about 2.9 mg/L, about 3 mg/L, about 3.1 mg/L, about 3.2 mg/L, about 3.3 mg/L, about 3.4 mg/L, about 3.5 mg/L, about 3.6 mg/L, about 3.7 mg/L, about 3.8 mg/L, about 3.9 mg/L, about 4 mg/L, about 4.1 mg/L, about 4.2 mg/L, about 4.3 mg/L, about 4.4 mg/L, about 4.5 mg/L, about 4.6 mg/L, about 4.7 mg/L, about 4.8 mg/L, about 4.9 mg/L, about 5 mg/L, about 5.1 mg/L, about 5.2 mg/L, about 5.3 mg/L, about 5.4 mg/L, about 5.5 mg/L, about 5.6 mg/L, about 5.7 mg/L, about 5.8 mg/L, about 5.9 mg/L, about 6 mg/L, about 6.1 mg/L, about 6.2 mg/L, about 6.3 mg/L, about 6.4 mg/L, about 6.5 mg/L, about 6.6 mg/L, about 6.7 mg/L, about 6.8 mg/L, about 6.9 mg/L, about 7 mg/L, about 7.1 mg/L, about 7.2 mg/L, about 7.3 mg/L, about 7.4 mg/L, about 7.5 mg/L, about 7.6 mg/L, about 7.7 mg/L, about 7.8 mg/L, about 7.9 mg/L, about 8 mg/L, about 8.1 mg/L, about 8.2 mg/L, about 8.3 mg/L, about 8.4 mg/L, about 8.5 mg/L, about 8.6 mg/L, about 8.7 mg/L, about 8.8 mg/L, about 8.9 mg/L, about 9 mg/L, about 9.1 mg/L, about 9.2 mg/L, about 9.3 mg/L, about 9.4 mg/L, about 9.5 mg/L, about 9.6 mg/L, about 9.7 mg/L, about 9.8 mg/L, about 9.9 mg/L, or about 10 mg/L. In some embodiments, the subject or subject group being treated has a baseline hsCRP level (or a mean or median baseline hsCRP level in the case of a subject group), fed or fasting, of about 2.2 mg/L, about 2 mg/L, about 1.8 mg/L, or about 1.9 mg/L.

In another embodiment, the subject or subject group being treated has a baseline inflammatory marker profile (or mean or median baseline inflammatory marker profile in the case of a subject group), fed or fasting, of one or more of: (a) a baseline (or median baseline) ICAM-1 level of about 250 ng/ml, (b) a baseline (or median baseline) ox-LDL level of about 79 U/L, (c) a baseline (or median baseline) Lp-PLA$_2$ level of about 246 ng/ml, (d) a baseline (or median baseline) IL-6 level of about 2.3 pg/ml, and (e) a baseline (or median baseline) hsCRP level of about 2.2 mg/L. In another embodiment, the subject or subject group being treated has a baseline inflammatory marker profile (or mean or median baseline inflammatory marker profile in the case of a subject group), fed or fasting, of: (a) a baseline (or median baseline) ICAM-1 level of about 256 ng/ml, (b) a baseline (or median baseline) ox-LDL level of about 76 U/L, (c) a baseline (or median baseline) Lp-PLA$_2$ level of about 235 ng/ml, (d) a baseline (or median baseline) IL-6 level of about 3 pg/ml, and/or (e) a baseline (or median baseline) hsCRP level of about 2 mg/L. In another embodiment, the subject or subject group being treated has a baseline inflammatory marker profile (or mean or median baseline inflammatory marker profile in the case of a subject group), fed or fasting, of one or more of: (a) a baseline (or median baseline) ICAM-1 level of about 248 ng/ml, (b) a baseline (or median baseline) ox-LDL level of about 74 U/L, (c) a baseline (or median baseline) Lp-PLA$_2$ level of about 253 ng/ml, (d) a baseline (or median baseline) IL-6 level of about 2.5 pg/ml, and (e) a baseline (or median baseline) hsCRP level of about 1.8 mg/L. In another embodiment, the subject or subject group being treated has a baseline inflammatory marker profile (or mean or median baseline inflammatory marker profile in the case of a subject group), fed or fasting, of one or more of: (a) a baseline (or median baseline) ICAM-1 level of about 273 ng/ml, (b) a baseline (or median baseline) ox-LDL level of about 54 U/L, (c) a baseline (or median baseline) Lp-PLA$_2$ level of about 180 ng/ml, (d) a baseline (or median baseline) IL-6 level of about 2.7 pg/ml, and/or (e) a baseline (or median baseline) hsCRP level of about 2.2 mg/L. In another embodiment, the subject or subject group being treated has a baseline inflammatory marker profile (or mean or median baseline inflammatory marker profile in the case of a subject group), fed or fasting, of one or more of: (a) a baseline (or median baseline) ICAM-1 level of about 267 ng/ml, (b) a baseline (or median baseline) ox-LDL level of about 54 U/L, (c) a baseline (or median baseline) Lp-PLA$_2$ level of about 190 ng/ml, (d) a baseline (or median baseline) IL-6 level of about 2.4 pg/ml, and/or (e) a baseline (or median baseline) hsCRP level of about 1.9 mg/L. In another embodiment, the subject or subject group being treated has a baseline inflammatory marker profile (or mean or median baseline inflammatory marker profile in the case of a subject group), fed or fasting, of: (a) a baseline (or median baseline) ICAM-1 level of about 269 ng/ml, (b) a baseline (or median baseline) ox-LDL level of about 52 U/L, (c) a baseline (or median baseline) Lp-PLA$_2$ level of about 185 ng/ml, (d) a baseline (or median baseline) IL-6 level of about 3.2 pg/ml, and/or (e) a baseline (or median baseline) hsCRP level of about 2 mg/L.

In another embodiment, the subject or subject group being treated has baseline levels (or mean or median baseline levels in the case of a subject group), fed or fasting, of one or more of: (a) an age of about 51.9 years; (b) a weight of about 93.2 kg; (c) a BMI of about 30.4 kg/m$^2$; and/or (d) a baseline triglyceride level of at least about 750 mg/dl. In another embodiment, the subject or subject group being treated has baseline levels (or mean or median baseline triglyceride level in the case of a subject group), fed or fasting, of one or more of: (a) an age of about 53.4 years; (b) a weight of about 92.1 kg; (c) a BMI of about 30.8 kg/m$^2$; and/or (d) a baseline triglyceride level of at least about 750 mg/dl. In another embodiment, the subject or subject group being treated has baseline levels (or mean or median baseline triglyceride level in the case of a subject group), fed or fasting, of one or more of: (a) an age of about 53.4 years; (b) a weight of about 93.0 kg; (c) a BMI of about 31.0 kg/m$^2$; and/or (d) a baseline triglyceride level of at least about 750 mg/dl. In another embodiment, the subject or subject group being treated is on statin therapy and has baseline levels (or mean or median baseline triglyceride level in the case of a subject group), fed or fasting, of one or more of: (a) an age of about 61.1 years; (b) a weight of about 94.5 kg; and/or (c) a BMI of about 32.7 kg/m$^2$. In another embodiment, the subject or subject group being treated is on statin therapy and has baseline levels (or mean or median baseline triglyceride level in the case of a subject group), fed or fasting, of one or more of: (a) an age of about 61.8 years; (b) a weight of about 95.5 kg; and/or (c) a BMI of about 32.9 kg/m$^2$. In another embodiment, the subject or subject group being treated is on statin therapy and has baseline levels (or mean or median baseline triglyceride level in the case of a subject group), fed or fasting, of one or more of: (a) an age of about 61.2 years; (b) a weight of about 97.0 kg; and/or (c) a BMI of about 33.0 kg/m$^2$. In some embodiments, the statin therapy includes a regimen including one or more of: atorvastatin (10-20 mg/day), atorvastatin (40-80 mg/day), rosuvastatin (5-10 mg/day), rosuvastatin (20-40 mg/day), simvastatin (5-10 mg/day), simvastatin (10-20 mg/day), simvastatin (80 mg/day), simvastatin (10-20 mg/day) with ezetimibe (5-10 mg/day), and simvastatin (40-80 mg/day) with ezetimibe (5-10 mg/day).

In one embodiment, the subject or subject group being treated in accordance with methods of the invention has previously been treated with Lovaza® and has experienced an increase in, or no decrease in, LDL-C levels and/or non-HDL-C levels. In one such embodiment, Lovaza® therapy is discontinued and replaced by a method of the present invention.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of total fatty acid (or mean thereof) not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline plasma, serum or red blood cell membrane EPA level not greater than about 70 μg/ml, not greater than about 60 μg/ml, not greater than about 50 μg/ml, not greater than about 40 μg/ml, not greater than about 30 μg/ml, or not greater than about 25 μg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline VLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

(a) reduced triglyceride levels compared to baseline or placebo control;

(b) reduced Apo B levels compared to baseline or placebo control;

(c) increased HDL-C levels compared to baseline or placebo control;

(d) no increase in LDL-C levels compared to baseline or placebo control;

(e) a reduction in LDL-C levels compared to baseline or placebo control;

(f) a reduction in non-HDL-C levels compared to baseline or placebo control;

(g) a reduction in VLDL levels compared to baseline or placebo control;

(h) an increase in apo A-I levels compared to baseline or placebo control;

(i) an increase in apo A-I/apo B ratio compared to baseline or placebo control;

(j) a reduction in lipoprotein A levels compared to baseline or placebo control;

(k) a reduction in LDL particle number compared to baseline or placebo control;

(l) an increase in LDL size compared to baseline or placebo control;

(m) a reduction in remnant-like particle cholesterol compared to baseline or placebo control;

(n) a reduction in oxidized LDL compared to baseline or placebo control;

(o) no change or a reduction in fasting plasma glucose (FPG) compared to baseline or placebo control;

(p) a reduction in hemoglobin $A_{1c}$ ($HbA_{1c}$) compared to baseline or placebo control;

(q) a reduction in homeostasis model insulin resistance compared to baseline or placebo control;

(r) a reduction in lipoprotein associated phospholipase A2 compared to baseline or placebo control;

(s) a reduction in intracellular adhesion molecule-1 compared to baseline or placebo control;

(t) a reduction in interleukin-6 compared to baseline or placebo control;

(u) a reduction in plasminogen activator inhibitor-1 compared to baseline or placebo control;

(v) a reduction in high sensitivity C-reactive protein (hsCRP) compared to baseline or placebo control;

(w) an increase in serum or plasma EPA compared to baseline or placebo control;

(x) an increase in red blood cell (RBC) membrane EPA compared to baseline or placebo control; and/or (y) a reduction or increase in one or more of serum phospholipid and/or red blood cell content of docosahexaenoic acid (DHA), docosapentaenoic acid (DPA), arachidonic acid (AA), palmitic acid (PA), staeridonic acid (SA) or oleic acid (OA) compared to baseline or placebo control.

In one embodiment, upon administering a composition of the invention to a subject, the subject exhibits a decrease in triglyceride levels, an increase in the concentrations of EPA and DPA (n–3) in red blood cells, and an increase of the ratio of EPA:arachidonic acid in red blood cells. In a related embodiment the subject exhibits substantially no or no increase in RBC DHA.

In one embodiment, methods of the present invention comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 25 of outcomes (a)-(y) described immediately above.

In one embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group including, for example, a subject or a subject group with a $HbA_{1c}$ value greater than or equal to about 4.90%, 4.95%, 5.00%, 5.05%, 5.10%, 5.15%, 5.20%, 5.25%, 5.30%, 5.35%, 5.40%, 5.45%, 5.50%, 5.55%, 5.60%, 5.65%, 5.70%, 5.75%, 5.80%, 5.85%, 5.90%, 5.95%, 6.00%, 6.05%, 6.10%, 6.15%, 6.20%, 6.25%, 6.30%, 6.35%, 6.40%, 6.45%, 6.50%, 6.55%, 6.60%, 6.65%, 6.70%, 6.75%, 6.80%, 6.85%, 6.90%, 6.95%, 7.00%, 7.05%, 7.10%, 7.15%, 7.20%, 7.25%, 7.30%, 7.35%, 7.40%, 7.45%, 7.50%, 7.55%, 7.60%, 7.65%, 7.70%, 7.75%, 7.80%, 7.85%, 7.90%, 7.95%, 8.00%, 8.05%, 8.10%, 8.15%, 8.20%, 8.25%, 8.30%, 8.35%, 8.40%, 8.45%, 8.50%, 8.55%, 8.60%, 8.65%, 8.70%, 8.75%, 8.80%, 8.85%, 8.90%, 8.95%, 9.00%, 9.05%, 9.10%, 9.15%, 9.20%, 9.25%, 9.30%, 9.35%, 9.40%, 9.45%, or 9.50% (or mean or median $HbA_{1c}$ value in the case of a subject group), exhibits one or more of outcomes (a)-(y) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(d) a less than 60% increase, a less than 50% increase, a less than 40% increase, a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline or placebo control;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(f) a reduction in VLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(n) substantially no change, no significant change, or a reduction (e.g. in the case of a diabetic subject) in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(o) substantially no change, no significant change or a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline or placebo control;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline or placebo control;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline or placebo control;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control; and/or (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 25 of outcomes (a)-(y) described immediately above.

In another embodiment, upon treatment with a composition of the present invention, the subject or subject group including, for example, the subject or the subject group with a $HbA_{1c}$ value greater than or equal to 6.8% (or mean or median $HbA_{1c}$ value in the case of a subject group), exhibits one or more of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-2 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, subjects fast for up to 12 hours prior to blood sample collection, for example about 10 hours.

In another embodiment, upon treatment with a composition of the present invention for about 12 weeks, the subject or subject group exhibits a placebo-adjusted reduction in hsCRP of at least about 2%, for example at least about 2%, 2.7%, at least about 3%, at least about 3.8%, at least about 4%, at least about 5%, at least about 6%, at least about 7%, at least about 8%, at least about 8.3%, at least about 9%, at least about 9.3%, at least about 10%, at least about 11%, at least about 12%, at least about 13%, at least about 13.6%, at least about 14%, at least about 15%, at least about 16%, at least about 17%, at least about 18%, at least about 19%, at least about 20%, at least about 21%, at least about 22%, at least about 22.8%, at least about 23%, at least about 24%, at least about 25%, at least about 26%, at least about 27%, at least about 27.4%, at least about 28%, at least about 28.6%, at least about 29%, at least about 30%, at least about 31%, at least about 31.4%, at least about 32%, at least about 33%, at least about 33.2%, at least about 34%, at least about 35%, at least about 36%, at least about 36.7%, at least about 37%, at least about 38%, at least about 39%, at least about 40%, at least about 42%, at least about 44%, at least about 46%, at least about 48%, at least about 50%, at least about 52%, at least about 54%, at least about 56%, at least about 58%, at least about 60%, at least about 62%, at least about 64%, at least about 66%, at least about 67%, at least about 67.9%, at least about 68%, at least about 70%, at least about 75%, or at least about 80% as compared to baseline. In some embodiments, the subject or subject group exhibits a placebo-adjusted reduction in hsCRP of 2.7%, about 3.8%, about 8.3%, about 9.3%, about 11%, about 13.6%, about 22.8%, about 27.4%, about 28.6%, about 31.4%, about 33.2%, about 36.7%, or about 67.9% as compared to baseline.

In some embodiments, upon treatment with about 4 g/day of a composition of the present invention for about 12 weeks, the subject or subject group experiences a placebo-adjusted reduction in hsCRP of at least about 27.4% as compared to baseline, wherein the subject or subject group was not on concomitant statin therapy, and had a baseline (or median baseline) triglyceride level of at least about 500 mg/dl and no more than about 1,500 mg/dl.

In some embodiments, upon treatment with about 2 g/day of a composition of the present invention for about 12 weeks, the subject or subject group experiences a placebo-adjusted reduction in hsCRP of at least about 2.7% as compared to baseline, wherein the subject or subject group was not on concomitant statin therapy, and had a baseline (or median baseline) triglyceride level of at least about 500 mg/dl and no more than about 1,500 mg/dl.

In some embodiments, upon treatment with about 4 g/day of a composition of the present invention for about 12 weeks, the subject or subject group experiences a placebo-adjusted reduction in hsCRP of at least about 67.9% as compared to baseline, wherein the subject or subject group was on concomitant statin therapy, and had a baseline (or median baseline) triglyceride level of at least about 500 mg/dl and no more than about 1,500 mg/dl.

In some embodiments, upon treatment with about 2 g/day of a composition of the present invention for about 12 weeks, the subject or subject group experiences a placebo-adjusted reduction in hsCRP of at least about 33.2% as compared to baseline, wherein the subject or subject group was on concomitant statin therapy, and had a baseline (or median baseline) triglyceride level of at least about 500 mg/dl and no more than about 1,500 mg/dl.

In some embodiments, upon treatment with about 4 g/day of a composition of the present invention for about 12 weeks, the subject or subject group experiences a placebo-adjusted reduction in hsCRP of at least about 36.7% as compared to baseline, wherein the subject or subject group was on concomitant atorvastatin therapy, and had a baseline (or median baseline) triglyceride level of at least about 200 mg/dl and less than about 500 mg/dl.

In some embodiments, upon treatment with about 2 g/day of a composition of the present invention for about 12 weeks, the subject or subject group experiences a placebo-adjusted reduction in hsCRP of at least about 9.3% as compared to baseline, wherein the subject or subject group was on concomitant atorvastatin therapy, and had a baseline (or median baseline) triglyceride level of at least about 200 mg/dl and less than about 500 mg/dl.

In some embodiments, upon treatment with about 4 g/day of a composition of the present invention for about 12 weeks, the subject or subject group experiences a placebo-adjusted reduction in hsCRP of at least about 31.4% as compared to baseline, wherein the subject or subject group was on concomitant rosuvastatin therapy, and had a baseline (or median baseline) triglyceride level of at least about 200 mg/dl and less than about 500 mg/dl.

In some embodiments, upon treatment with about 2 g/day of a composition of the present invention for about 12 weeks, the subject or subject group experiences a placebo-adjusted reduction in hsCRP of at least about 11% as compared to baseline, wherein the subject or subject group was on concomitant rosuvastatin therapy, and had a baseline (or median baseline) triglyceride level of at least about 200 mg/dl and less than about 500 mg/dl.

In some embodiments, upon treatment with about 4 g/day of a composition of the present invention for about 12 weeks, the subject or subject group experiences a placebo-adjusted reduction in hsCRP of at least about 13.6% as compared to baseline, wherein the subject or subject group was on concomitant simvastatin therapy, and had a baseline (or median baseline) triglyceride level of at least about 200 mg/dl and less than about 500 mg/dl.

In some embodiments, upon treatment with about 2 g/day of a composition of the present invention for about 12 weeks, the subject or subject group experiences a placebo-adjusted reduction in hsCRP of at least about 3.8% as compared to baseline, wherein the subject or subject group was on concomitant simvastatin therapy, and had a baseline (or median baseline) triglyceride level of at least about 200 mg/dl and less than about 500 mg/dl.

In some embodiments, upon treatment with about 4 g/day of a composition of the present invention for about 12 weeks, the subject or subject group experiences a placebo-adjusted reduction in hsCRP of at least about 22.8% as compared to baseline, wherein the subject or subject group had a baseline (or median baseline) triglyceride level of at least about 200 mg/dl and less than about 500 mg/dl, and wherein the subject or subject group was on concomitant statin therapy selected from: concomitant rosuvastatin therapy (5-10 mg/day), concomitant atorvastatin therapy (10-20 mg/day), concomitant simvastatin therapy (20-40 mg/day without ezetimibe), and concomitant simvastatin therapy (10-20 mg/day with ezetimibe 5-10 mg/day).

In some embodiments, upon treatment with about 2 g/day of a composition of the present invention for about 12 weeks, the subject or subject group experiences a placebo-adjusted reduction in hsCRP of at least about 8.3% as compared to baseline, wherein the subject or subject group had a baseline (or median baseline) triglyceride level of at least about 200 mg/dl and less than about 500 mg/dl, and wherein the subject or subject group was on concomitant statin therapy selected from: concomitant rosuvastatin therapy (5-10 mg/day), concomitant atorvastatin therapy (10-20 mg/day), concomitant simvastatin therapy (20-40 mg/day without ezetimibe), and concomitant simvastatin therapy (10-20 mg/day with ezetimibe 5-10 mg/day).

In some embodiments, upon treatment with about 4 g/day of a composition of the present invention for about 12 weeks, the subject or subject group experiences a placebo-adjusted reduction in hsCRP of at least about 28.6% as compared to baseline, wherein the subject or subject group had a baseline (or median baseline) triglyceride level of at least about 200 mg/dl and less than about 500 mg/dl, and wherein the subject or subject group was on concomitant statin therapy selected from: concomitant rosuvastatin therapy (20-40 mg/day), concomitant atorvastatin therapy (40-80 mg/day), concomitant simvastatin therapy (80 mg/day without ezetimibe), and concomitant simvastatin therapy (40-80 mg/day with ezetimibe 5-10 mg/day).

In some embodiments, a subject or subject group treated according to one of the methods of the present disclosure experiences a placebo-adjusted reduction in hsCRP levels as compared to baseline without experiencing a significant reduction or a reduction as compared to baseline of one or more of: ICAM-1, ox-LDL, Lp-PLA$_2$, and/or IL-6. In some embodiments, a subject or subject group treated according to one of the methods of the present disclosure experiences a placebo-adjusted reduction in hsCRP levels as compared to baseline and a placebo-adjusted reduction as compared to baseline in ox-LDL and/or Lp-PLA$_2$.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the patient one or more compositions as disclosed herein.

In one embodiment, a composition of the invention is administered to a subject in an amount sufficient to provide a daily dose of EPA of about 1 mg to about 10,000 mg, about 5000 mg, about 50 to about 3000 mg, about 75 mg to about 2500 mg, or about 100 mg to about 1000 mg, for example about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, about or about 10,000 mg.

In another embodiment, any of the methods disclosed herein are used in treatment of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In another embodiment, any of the methods disclosed herein are used in treatment of a subject or subjects that consume less than (actual or average) about 150 g, less than about 125 g, less than about 100 g, less than about 75 g, less than about 50 g, less than about 45 g, less than about 40 g, less than about 35 g, less than about 30 g, less than about 25 g, less than about 20 g or less than about 15 g of fish per day.

In another embodiment, any of the methods disclosed herein are used in treatment of a subject or subjects that consume less than (actual or average) about 10 g, less than about 9 g, less than about 8 g, less than about 7 g, less than about 6 g, less than about 5 g, less than about 4 g, less than about 3 g, less than about 2 g per day of omega-3 fatty acids from dietary sources.

In another embodiment, any of the methods disclosed herein are used in treatment of a subject or subjects that consume less than (actual or average) about 2.5 g, less than about 2 g, less than about 1.5 g, less than about 1 g, less than about 0.5 g, less than about 0.25 g, or less than about 0.2 g per day of EPA and DHA (combined) from dietary sources.

In one embodiment, compositions useful in various embodiments of the invention comprise a polyunsaturated fatty acid as an active ingredient. In another embodiment, such compositions comprise EPA as an active ingredient. The term "EPA" as used herein refers to eicosapentaenoic acid (e.g. eicosa-5,8,11,14,17-pentaenoic acid) and/or a pharmaceutically acceptable ester, derivative, conjugate or salt thereof, or mixtures of any of the foregoing.

In one embodiment, the EPA comprises all-cis eicosa-5,8,11,14,17-pentaenoic acid. In another embodiment, the EPA is in the form of an eicosapentaenoic acid ester. In another embodiment, the EPA comprises a $C_1$-$C_5$ alkyl ester of EPA. In another embodiment, the EPA comprises eicosapentaenoic acid ethyl ester, eicosapentaenoic acid methyl ester, eicosapentaenoic acid propyl ester, or eicosapentaenoic acid butyl ester. In still another embodiment, the EPA comprises all-cis eicosa-5,8,11,14,17-pentaenoic acid ethyl ester.

In still other embodiments, the EPA comprises ethyl-EPA, lithium EPA, mono, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

The term "pharmaceutically acceptable" in the present context means that the substance in question does not produce unacceptable toxicity to the subject or interaction with other components of the composition.

In one embodiment, EPA present in a composition suitable for use according to the invention comprises ultra-pure EPA. The term "ultra-pure" as used herein with respect to EPA refers to a composition comprising at least 90% by weight EPA (as the term "EPA" is defined and exemplified herein). Ultra-pure EPA can comprise even higher purity EPA, for example at least 91%, at least 92%, at least 93%, at least 94%, at least 95%, at least 96%, at least 97%, at least 98% or at least 99%, by weight of all fatty acids, EPA, wherein the EPA is any form of EPA as set forth herein. Ultra-pure EPA can further be defined (e.g. impurity profile) by any of the description of EPA provided herein.

In some embodiments, EPA is present in a composition in an amount of about 50 mg to about 5000 mg, about 75 mg to about 2500 mg, or about 100 mg to about 1000 mg, for example about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, or about 5000 mg.

In various embodiments, one or more antioxidants can be present in the EPA (e.g. E-EPA or ultra pure E-EPA). Non-limiting examples of suitable antioxidants include tocopherol, lecithin, citric acid and/or ascorbic acid. One or more antioxidants, if desired, are typically present in the EPA in an amount of about 0.01% to about 0.1%, by weight, or about 0.025% to about 0.05%, by weight.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of total fatty acids, docosahexaenoic acid or derivative thereof such as E-DHA, if any. In another embodiment, a composition of the invention contains substantially no docosahexaenoic acid or derivative thereof such as E-DHA. In still another embodiment, a composition of the invention contains no docosahexaenoic acid or E-DHA.

In another embodiment, EPA represents at least about 60%, at least about 70%, at least about 80%, at least about 90%, at least about 95%, at least about 97%, at least about 98%, at least about 99%, or 100%, by weight, of all fatty acids present in a composition useful in accordance with the invention.

In another embodiment, a composition of the invention contains less than 30%, less than 20%, less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA, or derivative thereof. Illustrative examples of a "fatty acid other than EPA" include linolenic acid (LA) or derivative thereof such as ethyl-linolenic acid, arachidonic acid (AA) or derivative thereof such as ethyl-AA, docosahexaenoic acid (DHA) or derivative thereof such as ethyl-DHA, alpha-linolenic acid (ALA) or derivative thereof such as ethyl-ALA, stearadonic acid (STA) or derivative thereof such as ethyl-SA, eicosatrienoic acid (ETA) or derivative thereof such as ethyl-ETA and/or docosapentaenoic acid (DPA) or derivative thereof such as ethyl-DPA.

In another embodiment, a composition of the invention has one or more of the following features: (a) eicosapentaenoic acid ethyl ester represents at least 96%, at least 97%, or at least 98%, by weight, of all fatty acids present in the composition; (b) the composition contains not more than 4%, not more than 3%, or not more than 2%, by weight, of total fatty acids other than eicosapentaenoic acid ethyl ester; (c) the composition contains not more than 0.6%, 0.5%, 0.4% or 0.3% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (f) the composition contains not more than 20 ppm, 15 ppm or 10 ppm heavy metals, (g) the composition contains not more than 5 ppm, 4 ppm, 3 ppm, or 2 ppm arsenic, and/or (h) the composition has a peroxide value not more than 5, 4, 3, or 2 meq/kg.

In another embodiment, a composition useful in accordance with the invention comprises, consists essentially of or consists of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In still another embodiment, the capsule shell contains no chemically modified gelatin.

In another embodiment, compositions useful in accordance with the invention comprise, consist essentially of, or consist of at least 95%, 96% or 97%, by weight, ethyl eicosapentaenoate, about 0.2% to about 0.5% by weight ethyl octadecatetraenoate, about 0.05% to about 0.25% by weight ethyl nonaecapentaenoate, about 0.2% to about 0.45% by weight ethyl arachidonate, about 0.3% to about 0.5% by weight ethyl eicosatetraenoate, and about 0.05% to about 0.32% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell. In another embodiment, the capsule shell contains no chemically modified gelatin.

In another embodiment, compositions useful in accordance with the invention comprise, consist essentially of, or consist of at least 96% by weight ethyl eicosapentaenoate, about 0.22% to about 0.4% by weight ethyl octadecatetraenoate, about 0.075% to about 0.20% by weight ethyl nonaecapentaenoate, about 0.25% to about 0.40% by weight ethyl arachidonate, about 0.3% to about 0.4% by weight ethyl eicosatetraenoate and about 0.075% to about 0.25% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel- or liquid-containing capsule and is packaged in blister packages of about 1 to about 20 capsules per sheet.

In another embodiment, compositions useful in accordance with the invention comprise, consist essentially of or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In another embodiment, the capsule shell contains no chemically modified gelatin.

In another embodiment, a composition as described herein is administered to a subject once or twice per day. In another embodiment, 1, 2, 3 or 4 capsules, each containing about 1 g (e.g., about 850 mg to about 1150 mg, about 900 mg to about 1100 mg, about 950 mg to about 1050 mg, or about 1000 mg) of a composition as described herein, are administered to a subject daily. In another embodiment, 1 or 2 capsules, each containing about 1 g (e.g., about 850 mg to about 1150 mg, about 900 mg to about 1100 mg, about 950 mg to about 1050 mg, or about 1000 mg) of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In one embodiment, a subject being treated in accordance with methods of the invention is not otherwise on lipid-altering therapy, for example statin, fibrate, niacin and/or ezetimibe therapy. In one embodiment, a subject being treated in accordance with methods of the invention is not on fibrate or nitrate therapy.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, the composition comprises about 1 g to about 4 g of eicosapentaenoic acid ethyl ester, wherein the composition contains substantially no docosahexaenoic acid.

In another embodiment, the invention provides use of any composition described herein for treating moderate to severe hypertriglyceridemia in a subject in need thereof, comprising: providing a subject having a fasting baseline triglyceride level of about 500 mg/dl to about 1500 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid.

In one embodiment, compositions of the invention, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

In one embodiment, the invention provides use of a composition as described herein in manufacture of a medicament for treatment of any of a cardiovascular-related disease. In another embodiment, the subject is diabetic.

In one embodiment, a composition as set forth herein is packaged together with instructions for using the composition to treat a cardiovascular disorder.

EXAMPLES

Example 1

Improvement of Cognitive Performance in Subjects with Age-Associated Memory Impairment A single-center, 6-week, double-blind, randomizes, parallel-group, placebo-controlled, dose-ranging pilot study was performed to evaluate the efficacy, tolerability, and safety of >96% ethyl-EPA in subjects with subjective and objective memory impairment according to generally accepted criteria for Age-Associated Memory Impairment ("AAMI"). The primary objective of the study was to determine the effect of >96% ethyl-EPA 1 g, 2 g, and 4 g daily, compared to placebo, on cognitive performance in subjects with AAMI.

The secondary objectives of this study were the following:
1. To determine the effect of >96% E-EPA on the following tests in the computerized cognitive battery:
   Continuity of attention tasks;
   Quality of working memory tasks;
   Quality of episodic memory tasks; and
   Speed of attention tasks;
2. To determine the safety and tolerability of >96% E-EPA from routine clinical laboratory tests, adverse events ("AE") monitoring, and vital signs; and
3. To determine the potential dose-effect relationship of >96% E-EPA on the cognitive endpoints by measurement of essential fatty acids in plasma and red blood cell membranes.

The population for this study was men and women between ages 50 and 70 with self-reported complaints of memory loss, subjective and objective cognitive impairment with a score of at least one standard deviation below that of the mean for age-matched elderly population as determined by the total score of between 13 and 20 from the Paired Associated Learning ("PAL") subset of the Wechsler Memory Scale, evidence of adequate intellectual function as determined by a scaled score of at least 9 (raw score of at least 32) on the Vocabulary subtest of the Wechsler Adult Intelligence Scale and absence of dementia as determined by a score of 24 or higher on the Mini-Mental State Examination ("MMSE").

Potential subjects were excluded based on the following exclusion criteria:
  Unlikely or unable to comply with investigational medication dosing requirements;
  Diagnosis of major depressive disorder, Alzheimer's or vascular dementia as defined according to the Mini International Neuropsychiatric Interview ("MINI")/Diagnostic and Statistical Manual of Mental Disorders (4th edition) Text Revision ("TR") criteria;
  Past or current history of:
    a neurological or psychiatric disorder that could have affected cognitive function;

inflammatory gastrointestinal disease such as Crohn's Disease or ulcerative colitis;

cancer other than basal cell carcinoma;

clinically significant cardiac abnormality as measured by 12-lead ECG;

Any other medical condition or intercurrent illness not adequately controlled, which, in the opinion of the study investigator, may have put the subject at risk when participating in the study or may have influenced the results of the study or affected the subject's ability to take part in the study;

Clinically significant abnormal screening results (e.g., haematology, biochemistry) on screening or vital signs that fell outside the normal range for this population, which in the opinion of the study investigator affected the subject's suitability for the study;

Changes to prescribed medication for a medical condition within 4 weeks of the baseline visit;

Omega-3 supplementation within 4 weeks of the baseline visit or during the study treatment period;

Currently taking anticoagulants or daily dose of aspirin greater than 325 mg.

Cough or flu remedies containing opiates or antihistamines within 2 weeks of the baseline visit or during the 6-week treatment period; and Known allergy to any ingredients of the study drug or placebo.

Ninety-four subjects were randomized into one of six groups: 1 g E-EPA daily (n=23), 2 g E-EPA daily (n=24), 4 g E-EPA daily (n=24), 1 g placebo daily (n=7), 2 g placebo daily (n=8), and 4 g placebo daily (n=8). E-EPA was provided as 500 mg soft gel capsules containing >96% E-EPA and 0.2% dl-$\alpha$-tocopherol as an antioxidant. Placebo capsules contained 467 mg of liquid paraffin and 0.2% dl-$\alpha$-tocopherol. Ninety-one subjects completed the study. Two subjects in the 2 g E-EPA group and one subject in the 2 g placebo group discontinued the study.

The study consisted of a screening visit, a training visit, and four study visits. At the screening visit, subjects' eligibility was determined through cognitive tests (verbal paired associated learning [PAL] subscale, vocabulary subtest, Memory Assessment Clinics Questionnaire [MAC-Q], mini mental state evaluation [MMSE] and MINI [mini international neuropsychiatric interview; sections 1 and 2 of Diagnostic and Statistical Manual of Mental Disorders, 4th Edition (DSM-IV) plus dysthymia]), haematology, clinical chemistry and 12-lead electrocardiogram (ECG). At the training visit, subjects were shown how to use the CDR computerized system. Subjects took study drug for 6 weeks and on Days 0, 14, 28 and 42, subjects underwent the CDR cognitive test battery.

At screening cognitive testing and suitability for the study were assessed using the Verbal Paired Associates 1 (Wechsler Memory Scale), Vocabulary Subtest of the WAIS, MAC-Q, MMSE and MINI (DSM-IV Sections 1 and 2 plus Dysthymia).

A selection of tasks from the CDR computerized cognitive assessment system were administered at Visit 2 (training visit), Visit 3 (baseline), Visit 4 (Day 14), Visit 5 (Day 28) and Visit 6 (Day 42). Parallel forms of the tests were presented at each testing session. All tasks were computer-controlled, the information presented on high resolution monitors, and the responses recorded via a response model containing two buttons: one marked 'no' and the other 'yes'. Five CDR composite scores were used as the primary/secondary outcome variables. The task titles were:

Word Presentation
Immediate Word Recall
Picture Presentation
Simple Reaction Time
Digit Vigilance
Choice Reaction Time
Spatial Working Memory
Numeric Working Memory
Delayed Word Recall
Word Recognition
Picture Recognition
Bond-Lader Visual Analogue Scales of Mood and Alertness
Screen, Using the Computer Mouse To ensure consistency of approach, full training on the cognitive tests and CDR test battery was provided to study site staff and study subjects. The results of each variable were automatically recorded using the machine interface developed by CDR.

Blood samples (10 mL) were collected at Visit 1 (screening) and at Visits 4, 5 and 6. Analysis was performed by MSR Lipid Analysis, Scottish Crop Research Institute, Dundee, UK. The screening sample acted as baseline for the EFA measurements. Lipid was extracted from plasma, serum and RBC suspensions and converted into fatty acid methyl esters which were analyzed by gas chromatography to give fatty acid profiles as micrograms fatty acid per gram of sample ($\mu$gFA/g) and normalized area percent.

All randomized subjects with at least 1 visit post-baseline were included in the Intent to Treat ("ITT") population, regardless of treatment actually received.

All randomized subjects that completed the study, excluding significant protocol deviators, were defined as the Safety Per Protocol population. An Efficacy Per Protocol population was based on the Efficacy completers. The intercept of the Safety and Efficacy Per Protocol populations defined the Study Per Protocol Population.

All randomized subjects that received at least 1 dose of study medication were included in the Safety Population.

Summary statistics were provided for the ITT and Study Per Protocol Populations separately for all composite scores, major and supportive variables. Summary statistics were performed for both the unadjusted and difference from baseline data (i.e. the difference from the time matched predose assessments on Day 0). Summary statistics were calculated by treatment, day and time-point. The summary statistics comprised n, mean, median, SD, standard error of mean ("SEM"), minimum and maximum values.

Difference from baseline data for each major variable was evaluated by an Analysis of Covariance ("ANCOVA") using SAS® PROC MIXED Version 8.2. Fixed effects for treatment, day, time point, treatment by day, treatment by time point, treatment by day by time-point were fitted. Subject within treatment was fitted as a repeated effect using the repeated statement. The compound symmetry covariance structure was used. Subjects' time-matched predose assessments on Day 0 were used as a covariate in the analysis.

Least squares means (LS means) were calculated for treatment by day, treatment by time-point and treatment by day by time-point interaction. This formal analysis was conducted for the ITT and Study PP Populations separately.

Safety evaluations were based on the safety population. Safety and tolerability were assessed in terms of AEs, vital signs, 12-lead ECG, clinical laboratory data, medical history, and study drug compliance. Safety and tolerability data were presented by treatment group.

RBC and plasma EFA data were collected at baseline, Day 14, 28 and 42 and summarized by visit for each treatment group. Change from baseline and percent change from baseline were also summarized. ANCOVA comparison of ethyl-EPA dose groups and ethyl-EPA versus placebo was performed.

Efficacy Results.

All CDR cognitive test battery analyses were completed for the ITT and Study PP analysis populations.

For the Intent-to-Treat Analysis for Power of Attention, there was no statistically significant effect of treatment, nor any treatment by day, treatment by time-point or treatment by day by time-point interactions. There was no LS mean difference between active treatment and placebo at any time-point.

For the contributing subtasks Simple Reaction Time and Digit Vigilance Speed, there were no statistically significant effects of treatment, nor any treatment by day, treatment by time-point or treatment by day by time-point interactions. For the subtask measure Choice Reaction Time, there was a statistically significant treatment by day interaction ($p=0.011$).

For the Study Per-Protocol Power of Attention, there was no statistically significant effect of treatment, nor any treatment by day, treatment by time-point or treatment by day by time-point interactions. There was no difference between active treatment and placebo at any time-point.

For the subtasks Simple Reaction Time and Digit Vigilance Speed, there were no statistically significant effects of treatment, nor any treatment by day, treatment by time-point or treatment by day by time-point interactions. For the subtask measure, Choice Reaction Time, there was a statistically significant treatment by day interaction ($p=0.013$).

The Intent-to-Treat Continuity of Attention and the contributing subtask Digit Vigilance Targets Detected tests showed no statistically significant effect of treatment, nor any treatment by day, treatment by time-point or treatment by day by time-point interactions.

For the Study Per Protocol Continuity of Attention test, there was no statistically significant effect of treatment, nor any treatment by day, treatment by time-point or treatment by day by time-point interactions.

For the subtask Digit Vigilance Targets Detected, there was a statistically significant treatment by time-point interaction ($p=0.040$).

For the Intent-to-Treat Quality of Working Memory test, there was a statistically significant treatment by day interaction ($p=0.019$).

For the contributing subtask Spatial Working Memory Sensitivity Index, there was a statistically significant treatment by day interaction ($p=0.015$).

For Numeric Working Memory Sensitivity Index, there was a statistical trend for a treatment by day interaction ($p=0.089$).

For the Study Per-Protocol Quality of Working Memory test, there was a statistically significant treatment by day interaction ($p=0.021$).

For the contributing subtask Spatial Working Memory Sensitivity Index, there was a statistically significant treatment by day interaction ($p=0.014$).

For the Intent-to-Treat Quality of Episodic Secondary Memory test, there was no statistically significant effect of treatment, nor any treatment by day, treatment by time-point or treatment by day by time-point interactions. The LS mean differences showed overall statistically significant decreases versus placebo for ethyl-EPA 1 g and 2 g ($p=0.040$ and $p=0.035$, respectively).

For the contributing subtasks Immediate and Delayed Word Recall Accuracies and for Word and Picture Recognition Sensitivity Indices, there were no statistically significant effects of treatment or treatment by day, treatment by time-point or treatment by day by time-point interactions. For Immediate Word Recall Accuracy, the LS mean differences showed statistically significant decreases for 1 g on Day 14 ($p=0.028$) and for 2 g on Day 28 ($p=0.017$). There were statistically significant decreases versus placebo for 1 g and 2 g at AM 1 ($p=0.040$ and $p=0.028$, respectively). There were statistically significant decreases for ethyl-EPA 1 g versus placebo on Day 14 at PM 2 ($p=0.020$) and for 2 g on Day 28 at AM 1 ($p=0.006$). For Word Recognition Sensitivity Index, the LS mean differences showed statistically significant decreases for ethyl-EPA 1 g on Day 28 ($p=0.024$) and for 4 g on Day 42 ($p=0.038$) versus placebo. There was a statistically significant decrease for 4 g at PM 2 ($p=0.045$) and a statistically significant decrease for 4 g versus placebo on Day 28 at PM 2 ($p=0.030$). For Picture Recognition Sensitivity Index, the LS mean differences showed statistically significant decrease for 1 g versus placebo on Day 28 at AM 2 ($p=0.017$) and at PM 2 ($p=0.040$). For the Study Per-Protocol Quality of Episodic Secondary Memory test, there were no statistically significant effects of treatment, nor treatment by day, treatment by time-point or treatment by day by time-point interactions. The LS mean differences showed overall statistically significant decreases versus placebo for 1 g and 2 g ($p=0.043$ and $p=0.036$, respectively).

For the contributing subtasks Immediate and Delayed Word Recall Accuracies and for Word and Picture Recognition Sensitivity Indices, there were no statistically significant effects of treatment or treatment by day, treatment by time-point or treatment by day by time-point interactions. For Immediate Word Recall Accuracy, the LS mean differences to placebo showed statistically significant decreases for ethyl-EPA 1 g on Day 14 ($p=0.024$) and for 2 g on Day 28 ($p=0.017$). There were statistically significant decreases for 1 g and 2 g at AM 1 ($p=0.038$ and $p=0.029$, respectively) and for 1 g at AM 2 ($p=0.048$). There were statistically significant decreases for 1 g versus placebo on Day 14 at PM 2 ($p=0.019$) and for 2 g on Day 28 at AM 1 ($p=0.006$).

For Word Recognition Sensitivity Index, the LS mean differences to placebo showed statistically significant decreases for 4 g on Day 42 ($p=0.038$) and for 1 g on Day 28 ($p=0.027$).

For Picture Recognition Sensitivity Index, the LS mean differences showed statistically significant decreases versus placebo for 1 g on Day 28 at AM 2 ($p=0.020$) and PM 2 ($p=0.026$).

For Intent-to-Treat Speed of Memory and the contributing subtasks Spatial and Numeric Working Memory Speeds and Word, and Picture Recognition Speeds, there were no statistically significant effects of treatment, nor treatment by day, treatment by time-point or treatment by day by time-point interactions. For Spatial Working Memory Speed, the LS mean differences showed a statistically significant benefit versus placebo for ethyl-EPA 4 g on Day 14 at PM 1 ($p=0.048$) and a trend for a benefit for 4 g on Day 42 at AM 1 ($p=0.061$). For Picture Recognition Speed, there were trends for benefits versus placebo for 1 g on Day 14 at AM 2 ($p=0.084$) and on Day 28 at AM 1 ($p=0.085$).

For Study Per-Protocol Speed of Memory and the contributing subtasks Spatial and Numeric Working Memory Speed and Word, and Picture Recognition Speed, there were no statistical significant effects of treatment, nor any treatment by day, treatment by time-point or treatment by day by time-point interactions.

For Intent-to-Treat Self-Rated Alertness, there was no statistically significant effect of treatment, nor any treatment by day, treatment by time-point or treatment by day by time-point interactions. The LS mean differences showed a statistically significant decrease in ratings for ethyl-EPA 2 g on Day 28 (p=0.047) versus placebo. There was a statistically significant decrease in ratings versus placebo for 2 g on Day 28 at AM 2 (p=0.041). For Study Per-Protocol Self-Rated Alertness, there was no statistically significant effect of treatment, nor any treatment by day, treatment by time-point or treatment by day by time-point interactions. The LS mean differences showed a statistically significant decrease in ratings for ethyl-EPA 2 g on Day 28 (p=0.035) versus placebo. There was a statistically significant decrease in ratings versus placebo for 2 g on Day 28 at AM 2 (p=0.033).

For Intent-to-Treat Self-Rated Contentment, there was a statistically significant treatment by day interaction (p<0.001). The LS mean difference to placebo showed no statistically significant effects. For Study Per-Protocol Self-Rated Contentment, there was a statistically significant treatment by day interaction (p<0.001). The LS mean difference to placebo showed no statistically significant effects.

For Intent-to-Treat Self-Rated Calmness, there was no statistically significant effect of treatment, nor any treatment by day, treatment by time-point or treatment by day by time-point interactions. For Study Per-Protocol Self-Rated Calmness, there was no statistically significant effect of treatment, nor any treatment by day, treatment by time-point or treatment by day by time-point interactions. The LS mean differences showed a statistical trend for an increase in ratings versus placebo for ethyl-EPA 4 g on Day 42 at PM 1 (p=0.071).

A post-hoc analysis compared the individual placebo groups (1 g, 2 g and 4 g paraffin oil) with the corresponding ethyl-EPA doses.

The pattern of data provided evidence that ethyl-EPA 4 g might improve speed in the attention based measures. For Power of Attention, there was an overall benefit versus the corresponding placebo for 4 g on Day 42. The subtask Simple Reaction Time showed improvements in performance for 4 g at PM 2 collapsed across days and at several time-points on Days 14 and 42. The improvements for 4 g were most pronounced in the Choice Reaction Time task, where there was an overall benefit versus corresponding placebo for 4 g, reflecting a benefit for 4 g over placebo on all study days. The pattern of improvement in performance throughout the assessment days was quite convincing as the improvements began on Day 14 with improvements seen at 2 time points, whereas on Day 42 ethyl-EPA 4 g was superior to placebo at every time point.

For Continuity of Attention, there were isolated declines or improvements in performance, but there was no general pattern of effects and it was considered unlikely these differences were due to the study compound. For Quality of Working Memory and in the subtask measure Numeric Working Memory Sensitivity Index, there were, as in the original analyses, only isolated improvements and declines in performance that were most likely not treatment-related. However, for Spatial Working Memory Sensitivity Index, there was an overall benefit for ethyl-EPA 4 g over placebo on Day 42 in the Study PP Population, which corresponds to the improvements seen for the attention based measures.

For Quality of Episodic Secondary Memory and contributing subtasks, there were a number of decreases for ethyl-EPA that could be explained by the pre-existing differences in performance between the placebo and active treatment groups which was seen in the original analyses. In contrast to the original analysis, the subtask measures of Speed of Memory showed some signs of improvement in performance for active treatment, mostly for 1 g versus placebo. For Self-rated Alertness and Self-rated Contentment, the 1 g dose showed decreases in ratings on Days 14 and 28. However, these decreases were not correlated with a decline in performance in the CDR attention tasks. As with the original planned analysis, there were no differences between active treatment and placebo in Self-Rated Calmness.

Safety Results.

Subjects who used less than 80% of the prescribed dose were to be considered non-compliant; other than those subjects who withdrew for other reasons only 1 subject fell into this category and was withdrawn.

Overall, 139 treatment emergent AEs ("TEAEs") were reported by 62 (66.0%) of subjects during the study. Most TEAEs were considered mild in severity and unrelated to study drug. More TEAEs were reported for the ethyl-EPA treatment groups (105 events) compared to the placebo treatment groups (34 events). One SAE was reported for the ethyl EPA 2 g treatment group and 3 subjects discontinued due to TEAEs: 2 subjects from the ethyl-EPA 2 g treatment group (the primary reason for discontinuation for 1 of these subjects was non-compliance), and 1 subject from the placebo 2 g treatment group.

There were no deaths during the study. No TEAEs were Definitely Related to the study drug. One subject receiving 1 g ethyl-EPA experienced nausea that was Probably Related to the study drug. Another subject receiving 4 g ethyl-EPA experienced diarrhea that was Probably Related to the study drug; another subject receiving 2 g placebo also experienced diarrhea that was Probably Related to the study drug. Five subjects experienced nausea that was Possibly Related to the study drug; two were in the 1 g ethyl-EPA cohort; one was in the 2 g ethyl-EPA cohort; two were in the 4 g ethyl-EPA cohort. One subject receiving 2 g placebo experienced headache that was Possibly Related to the study drug. All other TEAEs were Not Related or Unlikely Related to the study drug, and included nasopharyngitis (n=3), cystitis (n=2), cough (n=7), toothache (n=2), pharyngolaryngeal pain (n=2), back pain (n=2), pollakiuria (n=2), influenza-like illness (n=2), headache (n=15), diarrhea (n=2), and nausea (n=1).

One subject with a history of transient ischaemic attack, hypertension and osteoarthritis of the hand and osteopaenia receiving 2 g ethyl-EPA experienced worsening epigastric chest pain 17 days after the start of the study and 9 days after the last dose of the study drug. A planned endoscopy revealed oesophagitis and a small hiatus hernia. The subject was treated with omeprazole, which settled her symptoms. The subject had taken felodipine, rosuvastatin, aspirin, glucosamine, and quinine within 14 days of the onset of her symptoms. The study investigator determined that her symptoms were unrelated to the study drug and withdrew the subject from the study. No other Serious Adverse Events occurred during the study.

Essential fatty acid parameters in plasma and RBCs was measured at baseline and on Day 14, 28 and 48 (shown in Tables 1-6). Notable changes for these parameters occurred in the ethyl-EPA treatment groups at Days 14, 28 and 42 compared to placebo. EPA, DPAn-3 and EPA/AA ratio values increased substantially from baseline, in plasma and RBC, to Day 42 for the ethyl-EPA 1, 2 and 4 g treatment groups, but remained similar to baseline in the placebo treatment groups. AA, DHA and DGLA values decreased substantially from baseline, in plasma and RBC, to day 42 for the ethyl EPA 1, 2 and 4 g treatment groups, but remained similar to baseline in the placebo treatment groups. The difference in EPA, AA (RBC only), DPAn-3, DGLA (1 g only for plasma) and EPA/AA ratio levels in the plasma and RBC were significantly (LS means, p<0.05) different for the ethyl-EPA 4 g treatment group compared to the ethyl-EPA 1 g and 2 g treatment groups.

TABLE 1

EFA Parameter EPA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 48.3 (31.03) | 44.9 (25.01) | 49.1 (17.23) | 47.5 (26.41) | 42.1 (16.18) | 42.5 (11.86) |
| Day 14: n | 23 | 22 | 24 | 7 | 7 | 8 |
| Mean (SD) | 61.2 (26.61) | 124.6 (42.25) | 207.7 (57.05) | 1.6 (24.69) | −1.2 (19.82) | 21.9 (32.91) |
| Day 28: n | 22 | 22 | 24 | 7 | 7 | 8 |
| Mean (SD) | 60.3 (36.03) | 142.2 (46.23) | 215.2 (58.68) | 6.5 (15.46) | 1.6 (13.64) | 1.3 (14.03) |
| Day 42: n | 23 | 22 | 24 | 7 | 7 | 8 |
| Mean (SD) | 62.0 (39.43) | 133.4 (43.34) | 204.6 (80.69) | 11.9 (26.34) | 0.4 (21.18) | 4.4 (23.32) |
| 1 or 2 g versus 4 g | | | | | | |
| LS Mean | −111.8 | −60.9 | — | — | — | — |
| CI | −123.6, −100 | −72.7, −49.0 | — | — | — | — |
| p-value | <0.001 | <0.001 | — | — | — | — |
| RBC | | | | | | |
| Baseline: n | 23 | 24 | 24 | 7 | 7 | 8 |
| Mean (SD) | 19.8 (10.85) | 18.9 (8.91) | 19.8 (5.28) | 20.4 (5.77) | 19.3 (6.58) | 17.2 (4.94) |
| Day 14: n | 23 | 22 | 24 | 7 | 7 | 8 |
| Mean (SD) | 12.3 (7.39) | 26.9 (9.15) | 39.5 (13.16) | −0.5 (6.32) | 0.0 (7.17) | 2.6 (6.73) |
| Day 28: n | 22 | 22 | 24 | 7 | 7 | 8 |
| Mean (SD) | 14.5 (10.47) | 32.9 (10.11) | 50.2 (15.82) | 1.5 (4.16) | 0.0 (7.06) | 0.6 (4.42) |
| Day 42: n | 23 | 22 | 24 | 7 | 7 | 8 |
| Mean (SD) | 17.6 (11.89) | 38.3 (12.46) | 52.5 (20.56) | −0.2 (5.90) | 1.0 (8.01) | −0.2 (6.97) |
| 1 or 2 g versus 4 g | | | | | | |
| LS Mean | −24.4 | −11.8 | — | — | — | — |
| CI | −27.6, −21.2 | −15.0, −8.6 | — | — | — | — |
| p-value | <0.001 | <0.001 | — | — | — | — |

TABLE 2

EFA Parameter AA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 202.5 (44.40) | 227.3 (42.26) | 220.9 (42.80) | 210.7 (35.68) | 191.6 (28.24) | 248.0 (53.52) |
| Day 14: n | 23 | 22 | 24 | 7 | 7 | 8 |
| Mean (SD) | −9.7 (22.20) | −13.9 (22.13) | −27.2 (28.39) | 0.8 (40.0) | −14.4 (19.45) | −5.9 (25.00) |
| Day 28: n | 22 | 22 | 24 | 7 | 7 | 8 |
| Mean (SD) | −11.3 (28.13) | 21.6 (28.32) | −43.7 (32.24) | 3.8 (28.11) | −7.4 (23.72) | −16.4 (31.42) |
| Day 42: n | 23 | 22 | 24 | 7 | 7 | 8 |
| Mean (SD) | −8.7 (31.35) | −27.3 (26.76) | −48.3 (22.20) | 8.2 (20.30) | −11.5 (20.88) | −11.0 (25.82) |
| 1 or 2 g versus 4 g | | | | | | |
| LS Mean | 4.2 | 15.6 | — | — | — | — |
| CI | −8.0, 16.4 | 3.4, 27.8 | — | — | — | — |
| p-value | 0.496 | 0.013 | — | — | — | — |
| RBC | | | | | | |
| Baseline: n | 23 | 24 | 24 | 7 | 8 | 8 |
| Mean (SD) | 171.2 (19.79) | 172.8 (22.79) | 171.0 (25.17) | 176.4 (17.65) | 152.8 (17.36) | 180.4 (23.68) |
| Day 14: n | 23 | 22 | 24 | 7 | 7 | 8 |
| Mean (SD) | −8.1 (21.95) | −3.1 (25.84) | −15.7 (26.76) | −8.5 (22.75) | 3.0 (18.28) | −8.1 (27.53) |
| Day 28: n | 22 | 22 | 24 | 7 | 7 | 8 |
| Mean (SD) | −17.0 (20.69) | −14.1 (26.89) | −22.8 (29.56) | 5.2 (22.95) | −2.6 (17.78) | −8.2 (26.89) |

TABLE 2-continued

EFA Parameter AA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Day 42: n | 23 | 22 | 24 | 7 | 7 | 8 |
| Mean (SD) | −14.2 (27.69) | −18.8 (25.62) | −34.4 (31.44) | −9.8 (21.59) | 9.7 (16.58) | −10.6 (33.49) |
| 1 or 2 g versus 4 g | | | | | | |
| LS Mean | 8.4 | 9.8 | — | — | — | — |
| CI | 2.0, 14.9 | 3.3, 16.2 | — | — | — | — |
| p-value | 0.010 | 0.003 | — | — | — | — |

TABLE 3

EFA Parameter DHA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 73.1 (30.43) | 75.1 (24.02) | 78.8 (19.00) | 73.7 (14.21) | 73.3 (27.74) | 76.7 (15.68) |
| Day 14: n | 23 | 22 | 24 | 7 | 7 | 8 |
| Mem (SD) | −6.4 (13.30) | −5.4 (14.29) | −10.3 (13.35) | 0.4 (18.16) | −0.8 (14.28) | 13.8 (21.05) |
| Day 28: n | 22 | 22 | 24 | 7 | 7 | 8 |
| Mean (SD) | −6.6 (15.53) | −8.1 (15.82) | −13.5 (14.10) | 4.7 (16.31) | −0.6 (8.29) | 6.0 (17.36) |
| Day 42: n | 23 | 22 | 24 | 7 | 7 | 8 |
| Mean (SD) | −5.4 (18.17) | −6.0 (16.69) | −13.8 (15.31) | 11.8 (21.27) | 0.8 (17.57) | 6.2 (13.40) |
| 1 or 2 g versus 4 g | | | | | | |
| LS Mean | −0.8 | 1.5 | — | — | — | — |
| CI | −7.3, 5.7 | −5.0, 8.1 | — | — | — | — |
| p-value | 0.810 | 0.644 | — | — | — | — |
| RBC | | | | | | |
| Baseline: n | 23 | 24 | 24 | 7 | 8 | 8 |
| Mean (SD) | 66.5 (18.65) | 64.8 (17.65) | 68.3 (14.24) | 71.1 (7.48) | 66.0 (15.90) | 66.2 (15.83) |
| Day 14: n | 23 | 22 | 24 | 7 | 7 | 8 |
| Mean (SD) | −4.6 (9.76) | −2.0 (9.46) | −6.9 (9.13) | −5.5 (11.93) | −0.2 (12.39) | −0.4 (12.50) |
| Day 28: n | 22 | 22 | 24 | 7 | 7 | 8 |
| Mean (SD) | −6.4 (11.57) | −6.2 (9.34) | −8.7 (11.63) | 0.6 (12.86) | −0.3 (11.29) | 1.1 (12.54) |
| Day 42: n | 23 | 22 | 24 | 7 | 7 | 8 |
| Mean (SD) | −7.0 (12.20) | −6.3 (9.42) | −13.8 (13.76) | −4.1 (12.02) | 4.6 (12.94) | −0.1 (17.63) |
| 1 or 2 g versus 4 g | | | | | | |
| LS Mean | 1.0 | 1.0 | — | — | — | — |
| CI | −3.5, 5.4 | −3.5, 5.5 | — | — | — | — |
| p-value | 0.674 | 0.664 | — | — | — | — |

TABLE 4

EFA Parameter DPAn-3 (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 21.1 (6.62) | 19.7 (4.50) | 21.7 (4.69) | 17.9 (5.18) | 18.0 (4.39) | 19.0 (2.67) |
| Day 14: n | 23 | 22 | 24 | 7 | 7 | 8 |
| Mean (SD) | 7.5 (5.11) | 17.4 (7.49) | 24.5 (11.28) | −0.2 (3.13) | −1.0 (3.59) | 2.2 (4.98) |
| Day 28: n | 22 | 22 | 24 | 7 | 7 | 8 |

TABLE 4-continued

EFA Parameter DPAn-3 (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Mean (SD) | 8.9 (5.62) | 19.4 (8.48) | 29.7 (13.23) | 1.2 (2.06) | 0.6 (3.44) | 1.3 (3.40) |
| Day 42: n | 23 | 22 | 24 | 7 | 7 | 8 |
| Mean (SD) | 11.3 (6.61) | 19.3 (8.63) | 32.0 (16.01) | 2.2 (3.29) | 0.1 (3.61) | 0.8 (6.70) |
| 1 or 2 g versus 4 g | | | | | | |
| LS Mean | −15.1 | −9.5 | — | — | — | — |
| CI | −17.6, −12.7 | −12.0, −7.1 | — | — | — | — |
| p-value | <0.001 | <0.001 | — | — | — | — |
| RBC | | | | | | |
| Baseline: n | 23 | 24 | 24 | 7 | 8 | 8 |
| Mean (SD) | 34.1 (5.43) | 33.2 (4.51) | 34.5 (4.34) | 34.0 (4.27) | 33.0 (1.20) | 32.4 (2.41) |
| Day 14: n | 23 | 22 | 24 | 7 | 7 | 8 |
| Mean (SD) | 0.9 (5.03) | 5.6 (6.28) | 5.4 (5.38) | −2.8 (4.86) | −0.3 (4.96) | −0.9 (4.74) |
| Day 28: n | 22 | 22 | 24 | 7 | 7 | 8 |
| Mean (SD) | 3.3 (5.42) | 9.4 (6.74) | 12.4 (6.98) | 0.1 (4.51) | −0.8 (4.03) | −0.6 (5.19) |
| Day 42: n | 23 | 22 | 24 | 7 | 7 | 8 |
| Mean (SD) | 6.5 (6.19) | 13.2 (7.23) | 16.2 (10.07) | −1.8 (4.64) | 2.2 (4.44) | −0.9 (6.03) |
| 1 or 2 g versus 4 g | | | | | | |
| LS Mean | −6.2 | −2.5 | — | — | — | — |
| CI | −7.8, −4.7 | −4.1, −1.0 | — | — | — | — |
| p-value | <0.001 | 0.002 | — | — | — | — |

TABLE 5

EFA Parameter DGLA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 7) |
| Plasma | | | | | | |
| Baseline: n | 23 | 24 | 24 | 7 | 8 | 7 |
| Mean (SD) | 51.2 (15.01) | 53.5 (14.12) | 57.1 (14.73) | 51.6 (9.20) | 41.6 (10.30) | 52.6 (7.74) |
| Day 14: n | 23 | 22 | 24 | 7 | 7 | 8 |
| Mean (SD) | −10.4 (10.90) | −14.1 (6.88) | −22.9 (9.00) | −4.1 (8.07) | −0.0 (8.63) | −1.0 (11.58) |
| Day 28: n | 22 | 22 | 24 | 7 | 7 | 8 |
| Mean (SD) | −10.6 (10.23) | −16.2 (9.88) | −24.2 (10.73) | −4.6 (7.43) | −0.6 (5.91) | 1.5 (11.78) |
| Day 42: n | 23 | 22 | 24 | 7 | 7 | 8 |
| Mean (SD) | −9.4 (9.41) | −17.3 (9.92) | −22.5 (10.87) | −3.9 (12.90) | 0.9 (9.34) | 0.8 (11.04) |
| 1 or 2 g versus 4 g | | | | | | |
| LS Mean | 3.7 | 2.5 | — | — | — | — |
| CI | 0.4, 7.0 | −0.9, 5.8 | — | — | — | — |
| p-value | 0.028 | 0.143 | — | — | — | — |
| RBC | | | | | | |
| Baseline: n | 23 | 24 | 24 | 7 | 8 | 7 |
| Mean (SD) | 23.0 (5.19) | 23.0 (5.76) | 24.0 (5.77) | 22.4 (5.06) | 19.7 (5.87) | 22.4 (4.91) |
| Day 14: n | 23 | 22 | 24 | 7 | 7 | 8 |
| Mean (SD) | −2.7 (3.82) | −2.6 (3.54) | −5.3 (4.10) | −1.5 (2.08) | 0.2 (1.76) | −1.8 (4.00) |
| Day 28: n | 22 | 22 | 24 | 7 | 7 | 8 |
| Mean (SD) | −3.8 (3.31) | −4.5 (3.58) | −7.1 (4.63) | 0.2 (3.63) | −0.7 (4.06) | −0.7 (3.81) |
| Day 42: n | 23 | 22 | 24 | 7 | 7 | 8 |
| Mean (SD) | −3.5 (4.51) | −5.3 (3.65) | −8.0 (4.98) | −1.6 (4.93) | 1.9 (3.61) | −1.1 (5.31) |
| 1 or 2 g versus 4 g | | | | | | |
| LS Mean | 1.5 | 1.5 | — | — | — | — |
| CI | 0.2, 2.9 | 0.1, 2.9 | — | — | — | — |
| p-value | 0.027 | 0.032 | — | — | — | — |

TABLE 6

EFA Parameter EPA/AA (Plasma and RBC) Mean change from Baseline to Days 14, 28 and 42.

|  | Ethyl-EPA | | | Placebo | | |
|---|---|---|---|---|---|---|
| EFA Parameter | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 0.2 (0.14) | 0.2 (0.12) | 0.2 (0.07) | 0.2 (0.11) | 0.2 (0.10) | 0.2 (0.07) |
| Day 14: n | 23 | 22 | 24 | 7 | 7 | 8 |
| Mean: (SD) | 0.3 (0.4) | 0.6 (0.23) | 1.1 (0.28) | 0.0 (0.09) | 0.0 (0.12) | 0.1 (0.12) |
| Day 28: n | 22 | 22 | 24 | 7 | 7 | 8 |
| Mean (SD) | 0.3 (0.20) | 0.8 (0.35) | 1.3 (0.42) | 0.0 (0.08) | 0.0 (0.09) | 0.0 (0.06) |
| Day 42: n | 23 | 22 | 24 | 7 | 7 | 8 |
| Mean (SD) | 0.3 (0.24) | 0.7 (0.29) | 1.3 (0.45) | 0.0 (0.10) | 0.0 (0.12) | 0.0 (0.08) |
| 1 or 2 g versus 4 g | | | | | | |
| LS Mean | −0.66 | −0.41 | — | — | — | — |
| CI | −0.731, −0597 | −0.475, −0.341 | — | — | — | — |
| p-value | <0.001 | <0.001 | — | — | — | — |
| RBC | | | | | | |
| Baseline: n | 23 | 24 | 24 | 7 | 8 | 8 |
| Mean (SD) | 0.1 (0.07) | 0.1 (0.06) | 0.1 (0.04) | 0.1 (0.04) | 0.1 (0.06) | 0.1 (0.03) |
| Day 14: n | 23 | 22 | 24 | 7 | 7 | 8 |
| Mean (SD) | 0.1 (0.04) | 0.2 (0.04) | 0.3 (0.07) | 0.0 (0.03) | −0.0 (0.05) | 0.0 (0.03) |
| Day 28: n | 22 | 22 | 24 | 7 | 7 | 8 |
| Mean (SD) | 0.1 (0.05) | 0.02 (0.06) | 0.4 (0.11) | 0.0 (0.01) | −0.0 (0.04) | 0.0 (0.02) |
| Day 42: n | 23 | 22 | 24 | 7 | 7 | 8 |
| Mean (SD) | 0.1 (0.06) | 0.3 (0.06) | 0.4 (0.14) | 0.0 (0.03) | −0.0 (0.05) | 0.0 (0.03) |
| 1 or 2 g versus 4 g | | | | | | |
| LS Mean | −0.18 | −0.11 | — | — | — | — |
| CI | −0.204, −0.162 | −0.126, −0.085 | — | — | — | — |
| p-value | <0.001 | <0.001 | — | — | — | — |

Example 2

Effect of EPA on Lipid and Inflammatory Parameters in Patients with Diabetes Mellitus-2

The effect of >96% E-EPA on lipid and inflammatory parameters was evaluated in patients with fasting triglyceride levels ≥150 mg/dl and <499 mg/dl on concomitant statin therapy. Patients with diabetes mellitus-2 were randomized and treated with either 2 g/day >96% E-EPA, 4 g/day >96%, or placebo for twelve weeks. At the end of the treatment period, several diabetes efficacy endpoints were evaluated including, TG, LDL-C, non-HDL-C, VLDL-C, Lp-PLA2, Apo B, TC, HDL-C, VLDL-TG, hs-CRP, oxLDL, and RLP-C.

Figure 2:
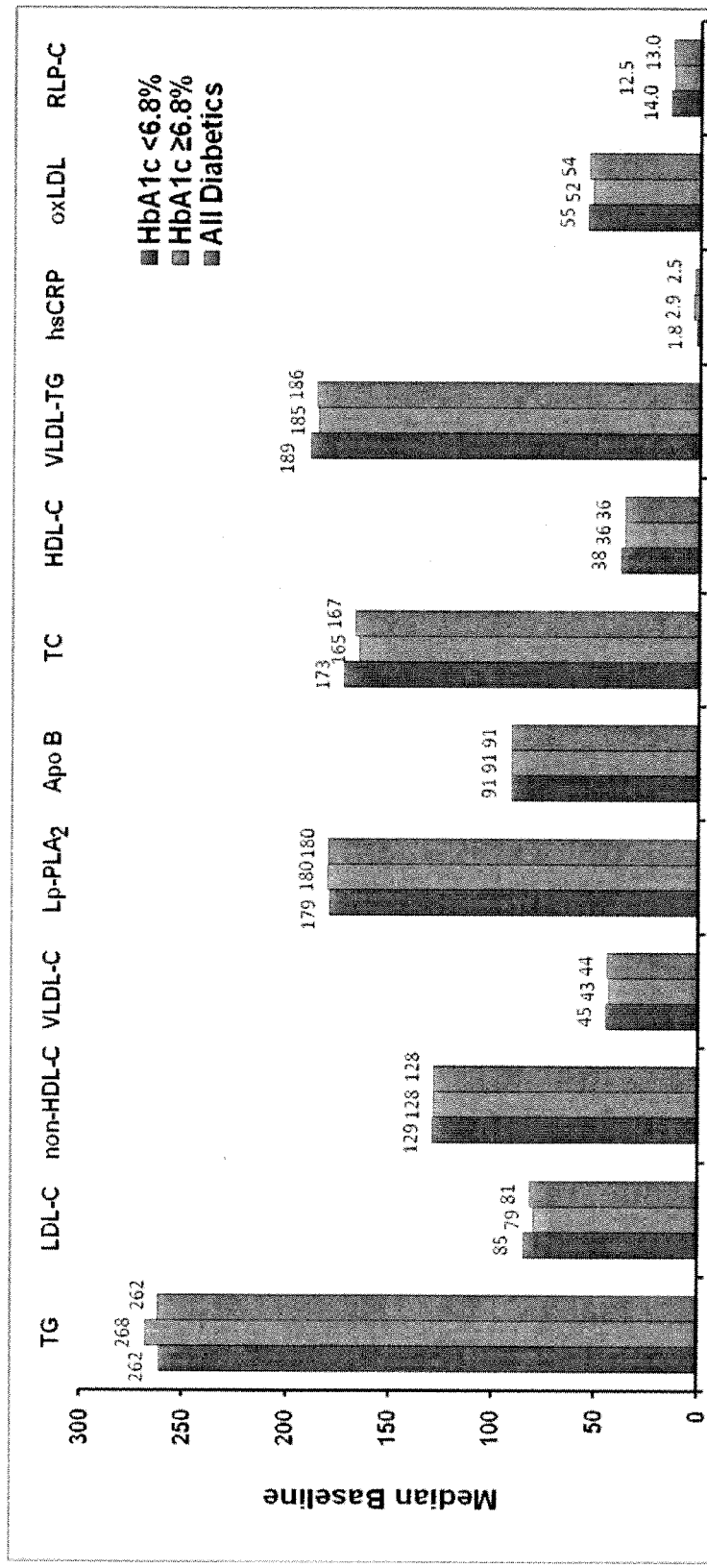
FIG. 2 shows a graphical depiction of the median baseline levels of TG, LDL-C, non-HDL-C, VLDL-C, Lp-PLA$_2$, Apo B, TC, HDL-C, VLDL-TG, hs-CRP, oxLDL, and RLP-C in diabetic subjects with a HbA$_{1c}$ value ≥6.8%, diabetic subjects with a HbA$_{1c}$ value <6.8%, and all diabetic subjects (subjects with a HbA$_{1c}$ value ≥6.8% and subjects with a HbA$_{1c}$ value <6.8%) that were treated with 4 g/day ultra-pure EPA for 12 weeks.
Figure 3:
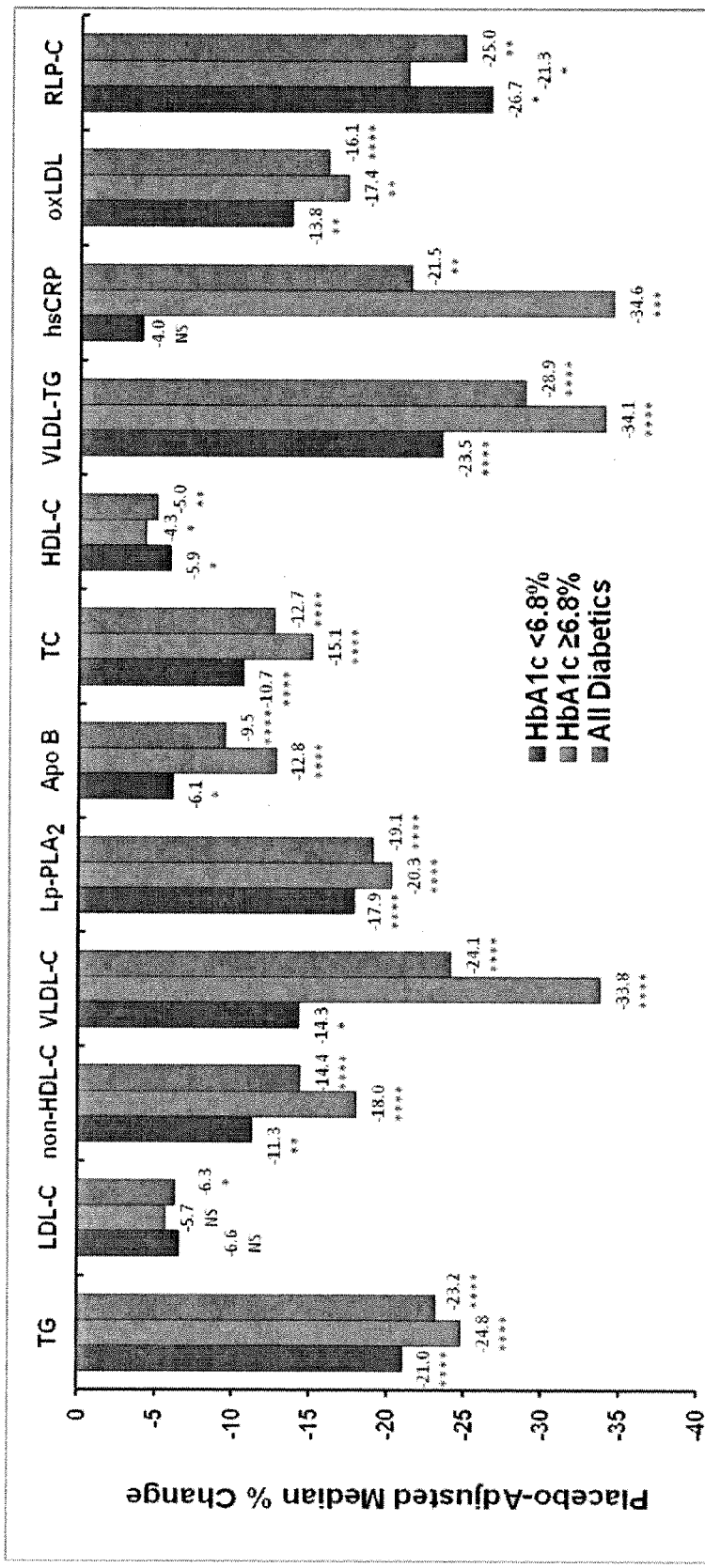
FIG. 3 shows a graphical depiction of the placebo adjusted median percent change in levels of TG, LDL-C, non-HDL-C, VLDL-C, Lp-PLA$_2$, Apo B, TC, HDL-C, VLDL-TG, hs-CRP, oxLDL, and RLP-C in diabetic subjects with a HbA$_{1c}$ value ≥6.8%, diabetic subjects with a HbA$_{1c}$ value <6.8%, and all diabetic subjects (subjects with a HbA$_{1c}$ value ≥6.8% and subjects with a HbA$_{1c}$ value <6.8%) that were treated with 4 g/day ultra-pure EPA for 12 weeks.

Each of the evaluated endpoints, when adjusted for placebo, showed a decrease in patients treated with either the 2 g/day or 4 g/day dose of >96% E-EPA (FIG. 1). Interestingly, median baseline levels of each endpoint in well-controlled diabetic subjects (HbA1c value <6.8%) treated with a 4 g/day dose of >96% E-EPA, less-controlled diabetic subjects (HbA1c value >6.8%) treated with a 4 g/day dose of >96% E-EPA, and all diabetics (well-controlled and less-controlled diabetic subjects) were similar for all endpoints with the exception of hsCRP (FIG. 2). Additionally, when these median baseline levels were adjusted for placebo, more pronounced effects were observed in less-controlled diabetics for non-HDL-C, VLDL-C, Apo B, TC, VLDL-TG, hsCRP, and oxLDL versus well-controlled subjects (Table 7 and FIG. 3).

TABLE 7

Median Placebo-adjusted Percent Change in Lipid and Inflammatory Parameters From Baseline to Study End in Patients With Diabetes Treated With Ultra-pure EPA 4 g/day.

| % Change in: | Well-controlled Diabetes*, P | Less-controlled Diabetes**, P | Total Diabetes, P |
|---|---|---|---|
| TG | −21.0 | −24.8 | −23.2 |
| (n = 78, 87, 165) | <0.0001 | <0.0001 | <0.0001 |
| LDL-C | −6.6 | −5.7 | −6.3 |
| (n = 78, 87, 165) | 0.0831 | 0.1304 | 0.0227 |
| Non-HDL-C | −11.3 | −18.0 | −14.4 |
| (n = 78, 87, 165) | 0.0019 | <0.0001 | <0.0001 |
| hsCRP | −4.0 | −34.6 | −21.5 |
| (n = 75, 85, 160) | 0.7372 | 0.0002 | 0.0028 |
| RLP-C | −26.7 | −21.3 | −25.0 |
| (n = 28, 32, 60) | 0.0468 | 0.0364 | 0.0024 |
| Apo B | −6.1 | −12.8 | −9.5 |
| (n = 75, 85, 160) | 0.0170 | <0.0001 | <0.0001 |

P-values are from Wilcoxon rank-sum test
*HbA1c < median of 6.8%
**HbA1c ≥ median of 6.8%

Figure 4:
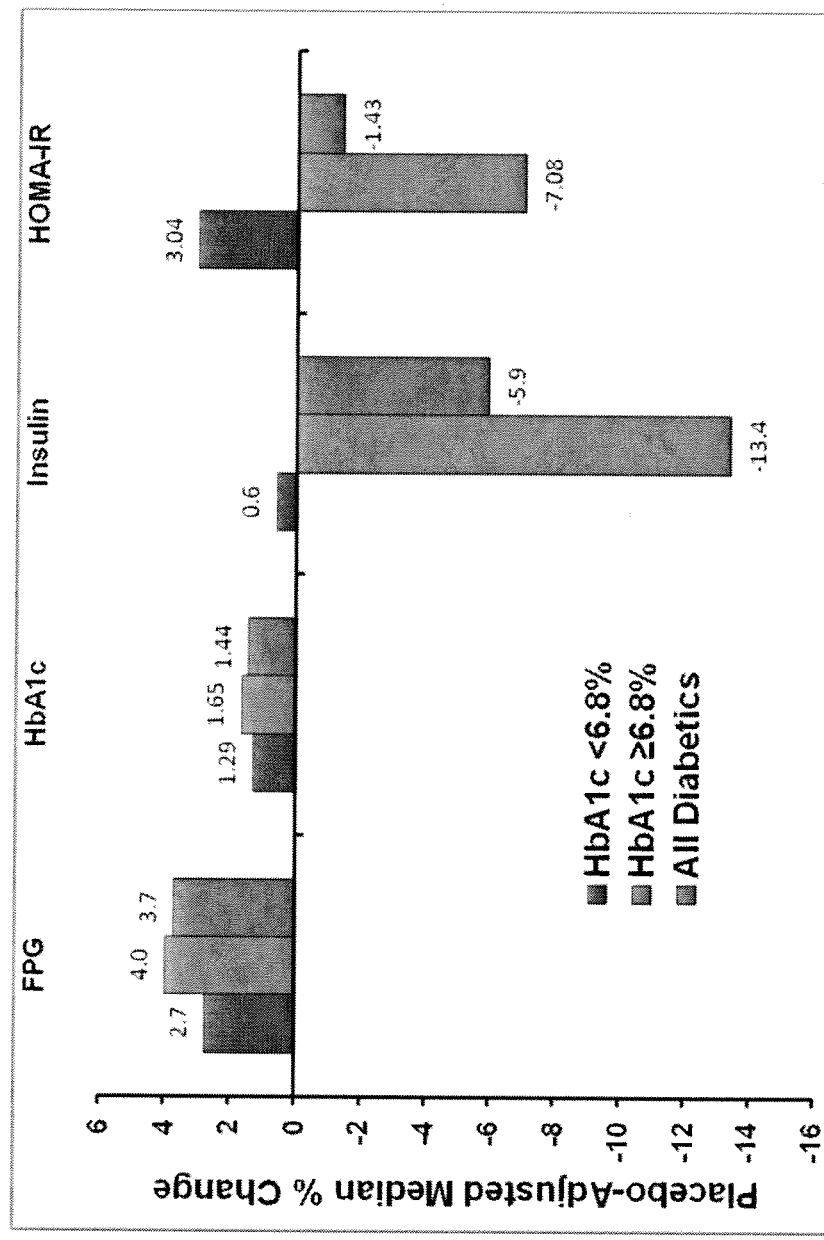
FIG. 4 shows a graphical depiction of the placebo-adjusted median percent change in diabetes endpoints including fasting plasma glucose (FPG), hemoglobin A$_1$, (HbA$_{1c}$), insulin, and homeostasis model assessment of insulin resistance (HOMA-IR) in diabetic subjects with a HbA$_{1c}$ value ≥6.8%, diabetic subjects with a HbA$_{1c}$ value <6.8%, and all diabetic subjects (subjects with a HbA$_{1c}$ value ≥6.8% and subjects with a HbA$_{1c}$ value <6.8%) that were treated with 4 g/day ultra-pure EPA for 12 weeks.

Further, there was no significant decrease in LDL-C levels between well-controlled subjects, less-controlled diabetic subjects, and all diabetic subjects. Importantly, no statistically significant changes in diabetes parameters including FPG, HbA1c, insulin and HOMA-IR were observed between well-controlled subjects, less-controlled diabetic subjects, and all diabetic subjects suggesting that treatment with a 4 g/day dose of >96% E-EPA did not worsen glycemic control (FIG. 4).

Example 3

Marine Study

A multi-center, placebo-controlled randomized, double-blind, 12-week study with an open-label extension was performed to evaluate the efficacy and safety of AMR101 in patients with fasting triglyceride levels ≥500 mg/dL. The primary objective of the study was to determine the efficacy of AMR101 2 g daily and 4 g daily, compared to placebo, in lowering fasting TG levels in patients with fasting TG levels ≥500 mg/dL and ≤1500 mg/dL (≥5.65 mmol/L and ≤16.94 mmol/L).

The secondary objectives of this study were the following:
 To determine the safety and tolerability of AMR101 2 g daily and 4 g daily;
 To determine the effect of AMR101 on lipid and apolipoprotein profiles;
 To determine the effect of AMR101 on low-density lipoprotein (LDL) particle number and size;
 To determine the effect of AMR101 on oxidized LDL;
 To determine the effect of AMR101 on fasting plasma glucose (FPG) and hemoglobin $A_{1c}$ ($HbA_{1c}$);
 To determine the effect of AMR101 on insulin resistance;
 To determine the effect of AMR101 on high-sensitivity C-reactive protein (hsCRP);
 To determine the effects of AMR101 2 g daily and 4 g daily on the incorporation of fatty acids into red blood cell membranes and into plasma phospholipids;
 To explore the relationship between baseline fasting TG levels and the reduction in fasting TG levels; and
 To explore the relationship between an increase in red blood cell membrane eicosapentaenoic acid (EPA) concentrations and the reduction in fasting TG levels.

The population for this study was men and women (women of childbearing potential will need to be on contraception or practice abstinence)>18 years of age with a body mass index ≤45 kg/m² who were not on lipid-altering therapy or were currently on lipid-altering therapy. Patients currently on statin therapy (with or without ezetimibe) were evaluated by the investigator as to whether this therapy can be safely discontinued at screening, or if it should be continued. If statin therapy (with or without ezetimibe) was to be continued, dose(s) must have been stable for ≥4 weeks prior to randomization. Patients taking non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Approximately 240 patients were randomized at approximately 50 centers in North America, South America, Central America, Europe, India, and South Africa. The study was a 58- to 60-week, Phase 3, multi-center study consisting of 3 study periods: (1) A 6- to 8-week screening period that included a diet and lifestyle stabilization and washout period and a TG qualifying period; (2) A 12-week, double-blind, randomized, placebo-controlled treatment period; and (3) A 40-week, open-label, extension period.

During the screening period and double-blind treatment period, all visits were to be within ±3 days of the scheduled time. During the open-label extension period, all visits were/are to be within ±7 days of the scheduled time. The screening period included a 4- or 6-week diet and lifestyle stabilization period and washout period followed by a 2-week TG qualifying period. Dose(s) must be stable for ≥4 weeks prior to randomization.

The screening visit (Visit 1) occurred for all patients at either 6 weeks (for patients not on lipid-altering therapy at screening or for patients who did not need to discontinue their current lipid-altering therapy) or 8 weeks (for patients who required washout of their then-current lipid-altering therapy at screening) before randomization, as follows:

Patients who did not require a washout: The screening visit occurred at Visit 1(Week −6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received instructions on how to follow this diet. Patients who required a washout: The screening visit occurred at Visit 1 (Week −8). Eligible patients began a 6-week washout period at the screening visit. Patients received counseling regarding the NCEP TLC diet and received instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week TG qualifying period and had their fasting TG level measured at Visit 2 (Week −2) and Visit 3 (Week −1). Eligible patients must have had an average fasting TG level 500 mg/dL and 1500 mg/dL (5.65 mmol/L and 16.94 mmol/L) to enter the 12-week double-blind treatment period. The TG level for qualification was based on the average (arithmetic mean) of the Visit 2 (Week −2) and Visit 3 (Week −1) values. If a patient's average TG level from Visit 2 and Visit 3 fell outside the required range for entry into the study, an additional sample for fasting TG measurement was collected 1 week later at Visit 3.1. If a third sample was collected at Visit 3.1, entry into the study was based on the average (arithmetic mean) of the values from Visit 3 and Visit 3.1.

After confirmation of qualifying fasting TG values, eligible patients entered a 12-week, randomized, double-blind treatment period. At Visit 4 (Week 0), patients were randomly assigned to 1 of the following treatment groups:
 AMR101 2 g daily,
 AMR101 4 g daily, or
 Placebo.

During the double-blind treatment period, patients returned to the site at Visit 5 (Week 4), Visit 6 (Week 11), and Visit 7 (Week 12) for efficacy and safety evaluations.

Patients who completed the 12-week double-blind treatment period were eligible to enter a 40-week, open-label, extension period at Visit 7 (Week 12). All patients received open-label AMR101 4 g daily. From Visit 8 (Week 16) until the end of the study, changes to the lipid-altering regimen were permitted (e.g., initiating or raising the dose of statin or adding non-statin, lipid-altering medications to the regimen), as guided by standard practice and prescribing information. After Visit 8 (Week 16), patients returned to the site every 12 weeks until the last visit at Visit 11 (Week 52).

Eligible patients were randomly assigned at Visit 4 (Week 0) to receive orally AMR101 2 g daily, AMR101 4 g daily, or placebo for the 12-week double-blind treatment period. AMR101 was provided in 1 g liquid-filled, oblong, gelatin capsules. The matching placebo capsule was filled with light liquid paraffin and contained 0 g of AMR101. During the double-blind treatment period, patients took 2 capsules (AMR101 or matching placebo) in the morning and 2 in the evening for a total of 4 capsules per day. Patients in the AMR101 2 g/day treatment group received 1 AMR101 1 g capsule and 1 matching placebo capsule in the morning and in the evening. Patients in the AMR101 4 g/day treatment group received 2 AMR101 1 g capsules in the morning and evening.

Patients in the placebo group received 2 matching placebo capsules in the morning and evening. During the extension period, patients received open-label AMR101 4 g daily. Patients took 2 AMR101 1 g capsules in the morning and 2 in the evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), calculated low-density lipoprotein cholesterol (LDL-C), calculated non-high-density lipoprotein cholesterol (non-HDL-C), and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-i/apo B ratio from baseline to Week 12;

Percent changes in lipoprotein(a) from baseline to Week 12 (selected sites only);

Percent changes in LDL particle number and size, measured by nuclear magnetic resonance, from baseline to Week 12 (selected sites only);

Percent change in remnant-like particle cholesterol from baseline to Week 12 (selected sites only);

Percent change in oxidized LDL from baseline to Week 12 (selected sites only);

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase A2 from baseline to Week 12 (selected sites only);

Change in intracellular adhesion molecule-1 from baseline to Week 12 (selected sites only);

Change in interleukin-6 from baseline to Week 12 (selected sites only);

Change in plasminogen activator inhibitor-1 from baseline to Week 12 (selected sites only);

Change in hsCRP from baseline to Week 12 (selected sites only);

Change in serum phospholipid EPA content from baseline to Week 12;

Change in red blood cell membrane EPA content from baseline to Week 12; and

Change in serum phospholipid and red blood cell membrane content in the following fatty acids from baseline to Week 12: docosapentaenoic acid, docosahexaenoic acid, arachidonic acid, palmitic acid, stearic acid, and oleic acid.

The efficacy variable for the open-label extension period was percent change in fasting TG from extension baseline to end of treatment. Safety assessments included adverse events, clinical laboratory measurements (chemistry, hematology, and urinalysis), 12-lead electrocardiograms (ECGs), vital signs, and physical examinations For TG, TC, HDL-C, calculated LDL-C, calculated non-HDL-C, and VLDL-C, baseline was defined as the average of Visit 4 (Week 0) and the preceding lipid qualifying visit (either Visit 3 [Week −1] or if it occurs, Visit 3.1) measurements. Baseline for all other efficacy parameters was the Visit 4 (Week 0) measurement.

For TC, HDL-C, calculated LDL-C, calculated non-HDL-C, and VLDL-C, Week 12 endpoint was defined as the average of Visit 6 (Week 11) and Visit 7 (Week 12) measurements. Week 12 endpoint for all other efficacy parameters was the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison was estimated. The same 2-way ANCOVA model was used for the analysis of secondary efficacy variables.

The primary analysis was repeated for the per-protocol population to confirm the robustness of the results for the intent-to-treat population.

The primary efficacy variable was the percent change in fasting TG levels from baseline to Week 12. A sample size of 69 completed patients per treatment group provided ≥90% power to detect a difference of 30% between AMR101 and placebo in percent change from baseline in fasting TG levels, assuming a standard deviation of 45% in TG measurements and a significance level of p<0.01. To accommodate a 15% drop-out rate from randomization to completion of the double-blind treatment period, a total of 240 randomized patients were planned (80 patients per treatment group).

Characteristics of the randomized subjects in this study are shown in Table 8 below.

TABLE 8

Patient Characteristics (Randomized Population)

|  | AMR101 4 g/day (n = 77) | AMR101 2 g/day (n = 76) | Placebo (n = 76) |
| --- | --- | --- | --- |
| Age, y, mean (SD) | 51.9 (10.27) | 53.4 (9.34) | 53.4 (8.34) |
| Male, n (%) | 59 (76.6) | 58 (76.3) | 58 (76.3) |
| White, n (%) | 67 (87.0) | 67 (88.2) | 68 (89.5) |
| Weight, kg, mean (SD) | 93.2 (18.27) | 92.1 (15.57) | 93.0 (16.92) |
| BMI, $kg/m^2$, mean (SD) | 30.4 (4.29) | 30.8 (4.24) | 31.0 (4.25) |
| Diabetes, n (%) | 22 (28.6) | 20 (26.3) | 21 (27.6) |
| Baseline TG >750 mg/dL, n (%) | 29 (37.7) | 29 (38.2) | 32 (42.1) |
| Statin use (any), n (%) | 20 (26.0) | 19 (25.0) | 18 (23.7) |

Baseline lipid parameters for subjects in the intent-to-treat ("ITT") population of this study are shown in Table 9 below. Data are presented as median (interquartile range) values.

TABLE 9

Baseline Lipid Parameters (ITT Population)

| Lipid Parameter (mg/dL) | AMR101 4 g/day (IQR) (n = 77) | AMR101 2 g/day (IQR) (n = 76) | Placebo 0 g/day (IQR) (n = 76) |
| --- | --- | --- | --- |
| TG | 679.5 (265.3) (n = 76) | 656.5 (303.5) (n = 73) | 703.0 (426.5) (n = 75) |
| LDL-C | 90.5 (42.5) (n = 76) | 84.0 (58.0) (n = 73) | 86.0 (58.0) (n = 75) |
| Non-HDL-C | 225.0 (89.5) (n = 76) | 210.0 (75.0) (n = 73) | 229.0 (85.0) (n = 75) |

TABLE 9-continued

Baseline Lipid Parameters (ITT Population)

| Lipid Parameter (mg/dL) | AMR101 4 g/day (IQR) (n = 77) | AMR101 2 g/day (IQR) (n = 76) | Placebo 0 g/day (IQR) (n = 76) |
|---|---|---|---|
| TC | 253.5 (86.5) (n = 76) | 236.0 (79.0) (n = 73) | 256.0 (97.0) (n = 75) |
| HDL-C | 26.5 (10.0) (n = 76) | 26.0 (6.0) (n = 73) | 27.0 (8.0) (n = 75) |

A summary of baseline values, end-of-treatment values, and median placebo-adjusted percent change from baseline to study end of inflammation-associated end points in each of the three ITT sub-populations is shown in Table 10.

Figure 5:
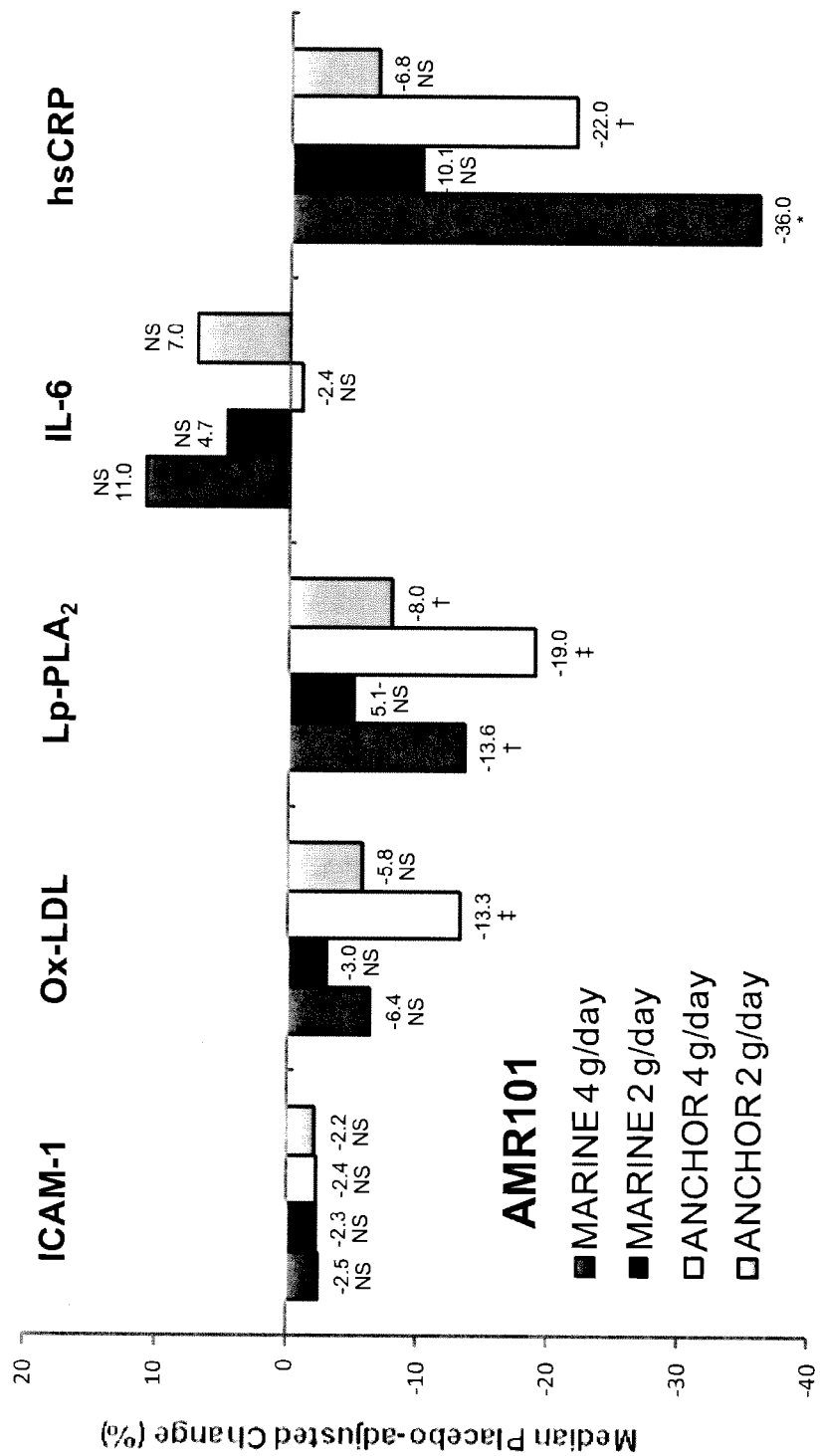
FIG. 5 depicts median placebo-adjusted percent change of five inflammatory markers from baseline to study end for subjects randomly assigned to 2 g/day and 4 g/day treatment groups in the MARINE and ANCHOR studies.

As shown Table 10 and corresponding FIG. 5, patients in the 4 g/day AMR101 study group experienced a median placebo-adjusted percent change in hsCRP levels of −36.0% compared to baseline (p<0.01), a median placebo-adjusted percent change in Lp-PLA$_2$ levels of −13.6% compared to baseline (p<0.001), and statistically insignificant median placebo-adjusted changes in ICAM-1, ox-LDL, and IL-6 levels compared to baseline.

Also as shown in Table 10 and corresponding FIG. 5, patients in the 2 g/day AMR101 study group experienced a median placebo-adjusted percent change in hsCRP levels of −10.1% compared to baseline (p>0.05), and statistically insignificant median placebo-adjusted changes in ICAM-1, ox-LDL, Lp-PLA$_2$, and IL-6 levels compared to baseline.

A summary of baseline hs-CRP values, end-of-treatment hs-CRP values, and median placebo-adjusted percent change from baseline to study end of hs-CRP levels in each of the three ITT sub-populations is shown in Table 11.

Figure 6A:
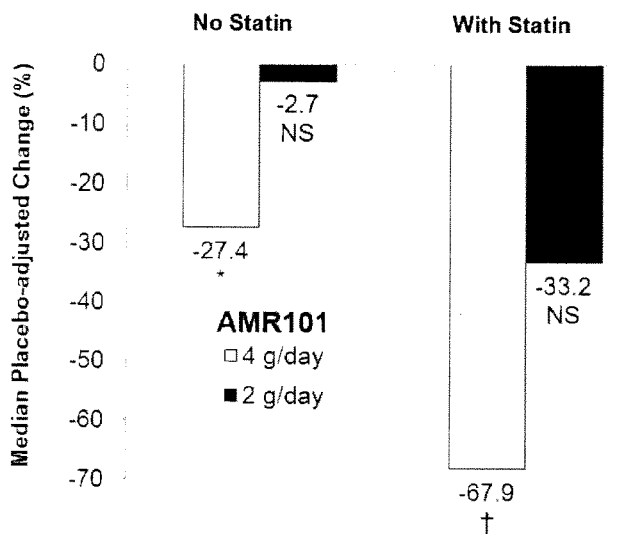
FIG. 6A depicts median placebo-adjusted percent change of hs-CRP from baseline to study end for subjects randomly assigned to 2 g/day and 4 g/day treatment groups in the ANCHOR study as a function of concomitant statin use (yes/no).

As shown in Table 11 and corresponding FIG. 6A, patients in the 2 g/day AMR101 treatment group had statistically insignificant median placebo-adjusted changes in hsCRP levels compared to baseline, regardless of concomitant statin therapy. However, patients in the 4 g/day AMR101 treatment group experienced a median placebo-adjusted change in hsCRP levels of −27.4% without concomitant statin therapy (p<0.05), and −67.9% with concomitant statin therapy (p<0.01).

Example 4

Anchor Study

A multi-center, placebo-controlled, randomized, double-blind, 12-week study was performed to evaluate the efficacy and safety of >96% E-EPA in patients with fasting triglyceride levels ≥200 mg/dl and <500 mg/dl despite statin therapy (the mean of two qualifying entry values needed to be ≥185 mg/dl and at least one of the values needs to be ≥200 mg/dl). The primary objective of the study was to determine the efficacy of >96% E-EPA 2 g daily and 4 g daily, compared to placebo, in lowering fasting TG levels in patients with high risk for cardiovascular disease and with fasting TG levels ≥200 mg/dL and <500 mg/dL, despite treatment to LDL-C goal on statin therapy.

The secondary objectives of this study were the following:
To determine the safety and tolerability of >96% E-EPA 2 g daily and 4 g daily;
To determine the effect of >96% E-EPA on lipid and apolipoprotein profiles including total cholesterol (TC), non-high-density lipoprotein cholesterol (non-HDL-C), low density lipoprotein cholesterol (LDL-C), high density lipoprotein cholesterol (HDL-C), and very high density lipoprotein cholesterol (VHDL-C);
To determine the effect of >96% E-EPA on lipoprotein associated phospholipase A$_2$ (Lp-PLA$_2$) from baseline to week 12;
To determine the effect of >96% E-EPA on low-density lipoprotein (LDL) particle number and size;
To determine the effect of >96% E-EPA on oxidized LDL;
To determine the effect of >96% E-EPA on fasting plasma glucose (FPG) and hemoglobin A$_{1c}$ (HbA$_{1c}$);
To determine the effect of >96% E-EPA on insulin resistance;
To determine the effect of >96% E-EPA on high-sensitivity C-reactive protein (hsCRP);
To determine the effects of >96% E-EPA 2 g daily and 4 g daily on the incorporation of fatty acids into red blood cell membranes and into plasma phospholipids;
To explore the relationship between baseline fasting TG levels and the reduction in fasting TG levels; and
To explore the relationship between changes of fatty acid concentrations in plasma and red blood cell membranes, and the reduction in fasting TG levels.

The population for this study was men and women >18 years of age with a body mass index ≤45 kg/m$^2$ with fasting TG levels greater than or equal to 200 mg/dl and less than 500 mg/dl and on a stable does of statin therapy (with or without ezetimibe). The statin must have been atorvostatin, rosuvastatin or simvastatin. The dose of statin must have been stable for ≥4 weeks prior to the LDL-C/TG baseline qualifying measurement for randomization. The statin dose was optimal such that the patients are at their LDL-C goal at the LDL-C/TG baseline qualifying measurements. The same statin at the same dose was continued until the study ended.

Patients taking any additional non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Patients at high risk for CVD, i.e., patients with clinical coronary heart disease (CHD) or clinical CHD risk equivalents (10-year risk >20%) as defined in the National Cholesterol Education Program (NCEP) Adult Treatment Panel III (ATP III) Guidelines were eligible to participate in this study. Those included patients with any of the following criteria: (1) Known CVD, either clinical coronary heart disease (CHD), symptomatic carotid artery disease (CAD), peripheral artery disease (PAD) or abdominal aortic aneurism; or (2) Diabetes Mellitus (Type 1 or 2).

Approximately 648 patients were randomized at approximately 80 centers in the U.S. The study was a 18- to 20-week, Phase 3, multi-center study consisting of 2 study periods: (1) A 6- to 8-week screening period that included a diet and lifestyle stabilization, a non-statin lipid-altering treatment washout, and an LDL-C and TG qualifying period and (2) A 12-week, double-blind, randomized, placebo-controlled treatment period.

During the screening period and double-blind treatment period, all visits were to be within ±3 days of the scheduled time. All patients continued to take the statin product (with or without ezetimibe) at the same dose they were taking at screening throughout their participation in the study.

The 6- to 8-week screening period included a diet and lifestyle stabilization, a non-statin lipid-altering treatment washout, and an LDL-C and TG qualifying period. The screening visit (Visit 1) occurred for all patients at either 6 weeks (for patients on stable statin therapy—with or without ezetimibe—at screening) or 8 weeks (for patients who required washout of their then-current non-statin lipid-altering therapy at screening) before randomization, as follows:

Patients who did not require a washout: The screening visit occurred at Visit 1 (Week −6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received basic instructions on how to follow this diet.

Patients who required a washout: The screening visit occurred at Visit 1 (Week −8). Eligible patients began a 6-week washout period at the screening visit (i.e. 6 weeks washout before the first LDL-C/TG qualifying visit). Patients received counseling regarding the NCEP TLC diet and received basic instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week LDL-C and TG qualifying period and had their fasting LDL-C and TG levels measured at Visit 2 (Week −2) and Visit 3 (Week −1). Eligible patients must have had an average fasting LDL-C level ≥40 mg/dL and <100 mg/dL and an average fasting TG level ≥200 mg/dL and <500 mg/dL to enter the 12-week double-blind treatment period. The LDL-C and TG levels for qualification were based on the average (arithmetic mean) of the Visit 2 (Week −2) and Visit 3 (Week −1) values. If a patient's average LDL-C and/or TG levels from Visit 2 and Visit 3 fall outside the required range for entry into the study, an additional fasting lipid profile was collected 1 week later at Visit 3.1. If a third sample was collected at Visit 3.1, entry into the study was based on the average (arithmetic mean) of the values from Visit 3 and Visit 3.1.

After confirmation of qualifying fasting LDL-C and TG values, eligible patients entered a 12-week, randomized, double-blind treatment period. At Visit 4 (Week 0), patients were randomly assigned to 1 of the following treatment groups:

>96% E-EPA 2 g daily,
>96% E-EPA 4 g daily, or
Placebo.

Approximately 216 patients per treatment group were randomized in this study. Stratification was by type of statin (atorvastatin, rosuvastatin or simvastatin), the presence of diabetes, and gender. Baseline parameters for randomized subjects in this study are shown in Table 12 below. The lower-efficacy statin regimen included administration of 5-10 mg of simvastatin per day; the medium-efficacy statin regimens included administration of 5-10 mg rosuvastatin per day, 10-20 mg of atorvastatin per day, 20-40 mg of simvastatin per day, or 10-20 mg of simvastatin and 5-10 mg of ezetimibe per day; and the higher-efficacy statin regimens included administration of 20-40 mg of rosuvastatin per day, 40-80 mg of atorvastatin per day, 80 mg of simvastatin per day, or 40-80 mg of simvastatin and 5-10 mg of ezetimibe per day.

TABLE 12

Patient Characteristics (Randomized Population)

|  | AMR101 4 g/day (n = 233) | AMR101 2 g/day (n = 236) | Placebo (n = 233) |
| --- | --- | --- | --- |
| Age, y, mean (SD) | 61.1 (10.03) | 61.8 (9.42) | 61.2 (10.05) |
| Male, n (%) | 142 (60.9) | 144 (61.0) | 145 (62.2) |
| White, n (%) | 226 (97.0) | 226 (95.8) | 224 (96.1) |
| Weight, kg, mean (SD) | 94.5 (18.30) | 95.5 (18.29) | 97.0 (19.14) |
| BMI, kg/m$^2$, mean (SD) | 32.7 (4.99) | 32.9 (4.98) | 33.0 (5.04) |
| Diabetes, n (%) | 171 (73.4) | 172 (72.9) | 171 (73.4) |
| Baseline TG >750 mg/dL, n (%) | NA | NA | NA |
| Statin use, n (%): |  |  |  |
| Any | 233 (100) | 236 (100) | 233 (100) |
| Atorvastatin | 44 (18.9) | 43 (18.2) | 45 (19.3) |
| Simvastatin | 134 (57.5) | 136 (57.6) | 133 (57.1) |
| Rosuvastatin | 55 (23.6) | 57 (24.2) | 55 (23.6) |
| Statin efficacy regimens, n (%) |  |  |  |
| Lower | 16 (6.9) | 17 (7.2) | 15 (6.4) |
| Medium | 148 (63.5) | 148 (62.7) | 144 (61.8) |
| Higher | 69 (29.6) | 71 (30.1) | 74 (31.8) |

Baseline lipid parameters for subjects in the intent-to-treat ("ITT") population of this study are shown in Table 13 below. Data are presented as median (interquartile range) values.

TABLE 13

Baseline Lipid Parameters (ITT Population)

| Lipid Parameter (mg/dL) | AMR101 4 g/day (IQR) (n = 233) | AMR101 2 g/day (IQR) (n = 236) | Placebo (IQR) (n = 233) |
| --- | --- | --- | --- |
| TG | 264.8 (93.0) (n = 226) | 254.0 (92.5) (n = 234) | 259.0 (81.0) (n = 227) |
| LDL-C | 82.0 (25.0) (n = 225) | 82.0 (24.0) (n = 233) | 84.0 (27.0) (n = 226) |
| Non-HDL-C | 128.0 (32.0) (n = 226) | 128.0 (33.0) (n = 234) | 128.0 (34.0) (n = 227) |
| TC | 167.0 (38.0) (n = 226) | 169.0 (34.0) (n = 234) | 168.0 (38.0) (n = 227) |
| HDL-C | 37.0 (12.0) (n = 226) | 38.0 (13.0) (n = 234) | 39.0 (12.0) (n = 227) |

During the double-blind treatment period, patients returned to the site at Visit 5 (Week 4), Visit 6 (Week 11), and Visit 7 (Week 12) for efficacy and safety evaluations.

Eligible patients were randomly assigned at Visit 4 (Week 0) to receive orally >96% E-EPA 2 g daily, >96% E-EPA 4 g daily, or placebo.

>96% E-EPA was provided in 1 g liquid-filled, oblong, gelatin capsules. The matching placebo capsule was filled with light liquid paraffin and contains 0 g of >96% E-EPA. >96% E-EPA capsules were to be taken with food (i.e. with or at the end of a meal).

During the double-blind treatment period, patients took 2 capsules (>96% E-EPA or matching placebo) in the morning and 2 capsules in the evening for a total of 4 capsules per day.

Patients in the >96% E-EPA 2 g/day treatment group received 1 >96% E-EPA 1 g capsule and 1 matching placebo capsule in the morning and in the evening.

Patients in the >96% E-EPA 4 g/day treatment group received 2 >96% E-EPA 1 g capsules in the morning and evening.

Patients in the placebo group received 2 matching placebo capsules in the morning and evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), LDL-C, calculated non-HDL-C, and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12;

Percent changes in LDL particle number and size, measured by nuclear magnetic resonance, from baseline to Week 12;

Percent change in remnant-like particle cholesterol from baseline to Week 12;

Percent change in oxidized LDL from baseline to Week 12;

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase $A_2$ ($Lp-PLA_2$) from baseline to Week 12;

Change in intracellular adhesion molecule-1 from baseline to Week 12;

Change in interleukin-2 from baseline to Week 12;

Change in plasminogen activator inhibitor-1 from baseline to Week 12. Note: this parameter will only be collected at sites with proper storage conditions;

Change in hsCRP from baseline to Week 12; and

Change in plasma concentration and red blood cell membrane content of fatty acid from baseline to Week 12 including EPA, docosapentaenoic acid (DPA), docosahexaenoic acid (DHA), arachidonic acid (AA), dihomo-γ-linolenic acid (DGLA), the ratio of EPA/AA, ratio of oleic acid/stearic acid (OA/SA), and the ratio of total omega-3 acids over total omega-6 acids.

Safety assessments included adverse events, clinical laboratory measurements (chemistry, hematology, and urinalysis), 12-lead electrocardiograms (ECGs), vital signs, and physical examinations.

For TG, TC, HDL-C, LDL-C, calculated non-HDL-C, and VLDL-C, baseline was defined as the average of Visit 4 (Week 0) and the preceding lipid qualifying visit (either Visit 3 [Week −1] or if it occurs, Visit 3.1) measurements. Baseline for all other efficacy parameters was the Visit 4 (Week 0) measurement.

For TG, TC, HDL-C, LDL-C, calculated non-HDL-C, and VLDL-C, Week 12 endpoint was defined as the average of Visit 6 (Week 11) and Visit 7 (Week 12) measurements.

Week 12 endpoint for all other efficacy parameters was the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison was estimated. The same 2-way ANCOVA model was used for the analysis of secondary efficacy variables.

The primary analysis was repeated for the per-protocol population to confirm the robustness of the results for the intent-to-treat population.

Non-inferiority tests for percent change from baseline in LDL-C were performed between >96% E-EPA doses and placebo using a non-inferiority margin of 6% and a significant level at 0.05.

For the following key secondary efficacy parameters, treatment groups were compared using Dunnett's test to control the Type 1 error rate: TC, LDL-C, HDL-C, non-HDL-C, VLDL-C, $Lp-PLA_2$, and apo B. For the remaining secondary efficacy parameters, Dunnett's test was not used and the ANCOVA output was considered descriptive.

The evaluation of safety was based primarily on the frequency of adverse events, clinical laboratory assessments, vital signs, and 12-lead ECGs. The primary efficacy variable was the percent change in fasting TG levels from baseline to Week 12. A sample size of 194 completed patients per treatment group provided 90.6% power to detect a difference of 15% between >96% E-EPA and placebo in percent change from baseline in fasting TG levels, assuming a standard deviation of 45% in TG measurements and a significance level of $p<0.05$.

Previous data on fasting LDL-C showed a difference in percent change from baseline of 2.2%, with a standard deviation of 15%, between study drug and placebo. A sample size of 194 completed patients per treatment group provided 80% power to demonstrate non-inferiority ($p<0.05$, one-sided) of the LDL-C response between >96% E-EPA 4 g daily and placebo, within a 6% margin. To accommodate a 10% drop-out rate from randomization to completion of the double-blind treatment period, a total of 648 randomized patients were planned (216 patients per treatment group).

A summary of baseline values, end-of-treatment values, and median placebo-adjusted percent change from baseline to study end of inflammation-associated end points in each of the three ITT sub-populations is shown in Table 10.

As shown in Table 10 and corresponding FIG. 5, patients in the 4 g/day AMR101 study group experienced a median placebo-adjusted percent change in hsCRP levels of −22.0% compared to baseline ($p<0.001$), a median placebo-adjusted percent change in $Lp-PLA_2$ levels of −19.0% compared to baseline ($p\leq0.0001$), a median placebo-adjusted percent change in ox-LDL levels of −13.3% compared to baseline ($p\leq0.0001$), and statistically insignificant median placebo-adjusted changes in ICAM-1 and IL-6 levels compared to baseline.

Also as shown in Table 10 and corresponding FIG. 5, patients in the 2 g/day AMR101 study group experienced a median placebo-adjusted percent change in hsCRP levels of −6.8% compared to baseline ($p>0.05$), a median placebo-adjusted percent change in $Lp-PLA_2$ levels of −8.0% compared to baseline ($p<0.001$), and statistically insignificant median placebo-adjusted changes in ICAM-1, ox-LDL, and IL-6 levels compared to baseline.

A summary of baseline hs-CRP values, end-of-treatment hs-CRP values, and median placebo-adjusted percent change from baseline to study end of hs-CRP levels in each of the three ITT sub-populations is shown in Table 11.

Figure 6B:
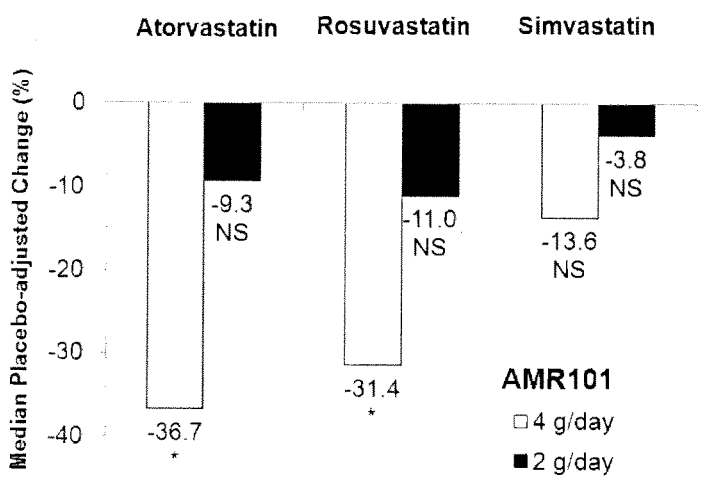
FIG. 6B depicts median placebo-adjusted percent change of hs-CRP from baseline to study end for subjects randomly assigned to 2 g/day and 4 g/day treatment groups in the MARINE study as a function of concomitant use of atorvastatin, rosuvastatin, or simvastatin.

As shown in Table 11 and corresponding FIG. 6B, patients in the 2 g/day AMR101 treatment group experienced a statistically insignificant median placebo-adjusted change in hsCRP levels (compared to baseline) regardless of concomitant atorvastatin, rosuvastatin or simvastatin therapy. Patients in the 4 g/day AMR101 treatment group also experienced a statistically insignificant median placebo-adjusted change in hsCRP levels (compared to baseline) with concomitant simvastatin therapy. However, patients in the 4 g/day AMR101 treatment group experienced a median placebo-adjusted change in hsCRP levels of −31.4% (compared to baseline) when on concomitant rosuvastatin therapy, and −36.7% (compared to baseline) when on concomitant atorvastatin therapy.

Figure 6C:
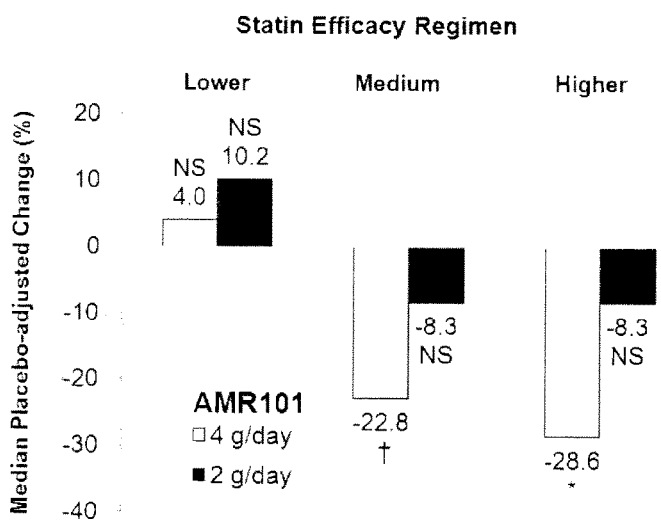
FIG. 6C depicts median placebo-adjusted percent change of hs-CRP from baseline to study end for subjects randomly assigned to 2 g/day and 4 g/day treatment groups in the MARINE study as a function of lower-, medium-, or higher-efficacy statin regimen.

As shown in Table 11 and corresponding FIG. 6C, patients in the 2 g/day AMR101 treatment group experienced a statistically insignificant median placebo-adjusted change in hsCRP levels (compared to baseline) regardless of concomitant low-medium-or high-efficacy statin therapy. Patients in the 4 g/day AMR101 treatment group also experienced a statistically insignificant median placebo-adjusted change in hsCRP levels (compared to baseline) with concomitant low-efficacy statin therapy (e.g., simvastatin 5-10 mg/day). However, patients in the 4 g/day AMR101 treatment group experienced a median placebo-adjusted change in hsCRP levels of −22.8% (compared to baseline, p<0.01) when on concomitant medium-efficacy statin therapy (e.g., rosuvastatin 5-10 mg/day, atorvastatin 10-20 mg/day, simvastatin 20-40 mg/day, or simvastatin 10-20 mg/day with ezetimibe 5-10 mg/day); and −28.6% (compared to baseline, p<0.05) when on concomitant high-efficacy statin therapy (e.g., rosuvastatin 20-40 mg/day, atorvastatin 40-80 mg/day, simvastatin 80 mg/day, or simvastatin 40-80 mg/day with ezetimibe 5-10 mg/day).

TABLE 10

Median Placebo-adjusted Percent Change From Baseline to Study End in Inflammation-associated End Points (ITT Populations).

| | AMR101 4 g/day | | | AMR101 2 g/day | | | Placebo | | | Median Placebo-adjusted % Change From Baseline | |
|---|---|---|---|---|---|---|---|---|---|---|---|
| | Baseline value (IQR) | End-of-treatment value (IQR) | Change from baseline, % (IQR) | Baseline value (IQR) | End-of-treatment value (IQR) | Change from baseline, % (IQR) | Baseline value (IQR) | End-of-treatment value (IQR) | Change from baseline, % (IQR) | AMR101 4 g/day vs placebo, P | AMR101 2 g/day vs placebo, P |
| MARINE | n = 76 | | | n = 73 | | | n = 75 | | | | |
| ICAM-1 (ng/mL) | 250.0 | 253.0 | −0.9 | 255.5 | 257.5 | −0.4 | 247.5 | 246.0 | 2.6 | −2.5 | −2.3 |
| (n = 75, 70, 72) | (85.00) | (89.00) | (10.69) | (86.00) | (102.00) | (12.29) | (101.00) | (89.50) | (13.43) | 0.1188 | 0.2201 |
| Ox-LDL (U/L) | 78.8 | 74.8 | −3.0 | 76.2 | 75.2 | 0.4 | 74.3 | 74.8 | 3.3 | −6.4 | −3.0 |
| (n = 74, 70, 71) | (26.51) | (26.52) | (2.35) | (24.00) | (23.52) | (2.41) | (24.86) | (23.32) | (2.39) | 0.0599 | 0.3818 |
| Lp-PLA$_2$ (ng/mL) | 246.0 | 201.0 | −17.1 | 235.0 | 220.5 | −5.1 | 253.0 | 256.0 | −2.4 | −13.6 | −5.1 |
| (n = 73, 70, 70) | (116.00) | (100.00) | (24.43) | (106.00) | (101.00) | (24.14) | (126.00) | (146.00) | (29.35) | 0.0003 | 0.1529 |
| IL-6 (pg/mL) | 2.3 | 2.4 | 0.3 | 3.0 | 3.0 | 3.4 | 2.5 | 2.3 | 5.3 | 11.0 | 4.7 |
| (n = 60, 62, 61) | (3.34) | (3.32) | (93.07) | (2.78) | (5.39) | (76.70) | (4.12) | (1.85) | (79.27) | 0.3629 | 0.6654 |
| hsCRP (mg/L) | 2.2 | 2.2 | −2.5 | 2.0 | 2.4 | 25.1 | 1.8 | 2.5 | 33.3 | −36.0 | −10.1 |
| (n = 75, 70, 72) | (3.10) | (2.90) | (81.19) | (2.70) | (3.20) | (96.43) | (3.05) | (3.95) | (80.49) | 0.0012 | 0.4028 |
| ANCHOR | n = 226 | | | n = 234 | | | n = 227 | | | | |
| ICAM-1 (ng/mL) | 273.0 | 270.0 | 0.8 | 267.0 | 268.5 | 0.5 | 269.0 | 257.0 | 3.6 | −2.4 | −2.2 |
| (n = 78, 74, 83) | (96.00) | (110.00) | (13.27) | (97.00) | (89.00) | (12.41) | (122.00) | (131.00) | (12.07) | 0.1888 | 0.1944 |
| Ox-LDL (U/L) | 54.0 | 51.4 | −4.8 | 54.0 | 55.8 | 2.6 | 51.8 | 59.7 | 11.6 | −13.3 | −5.8 |
| (n = 78, 75, 84) | (14.60) | (17.50) | (19.63) | (17.80) | (22.80) | (18.28) | (16.80) | (18.10) | (28.09) | 0.0001 | 0.0946 |
| Lp-PLA$_2$ (ng/mL) | 180.0 | 160.0 | −12.8 | 190.0 | 183.5 | −1.8 | 185.0 | 200.0 | 6.7 | −19.0 | −8.0 |
| (n = 217, 224, 213) | (56.00) | (57.00) | (18.52) | (55.50) | (57.50) | (23.11) | (58.00) | (71.00) | (24.03) | <0.0001 | <0.0001 |
| IL-6 (pg/mL) | 2.7 | 2.6 | 3.1 | 2.4 | 2.7 | 6.9 | 3.2 | 2.9 | 3.3 | −1.0 | 7.0 |
| (n = 78, 74, 83) | (2.61) | (2.08) | (56.47) | (2.01) | (2.28) | (51.85) | (3.23) | (2.95) | (59.37) | 0.9031 | 0.3643 |
| hsCRP (mg/L) | 2.2 | 2.0 | −2.4 | 1.9 | 2.5 | 10.3 | 2.2 | 2.6 | 17.1 | −22.0 | −6.8 |
| (n = 217, 227, 219) | (2.70) | (3.00) | (62.75) | (2.90) | (3.40) | (88.61) | (4.00) | (4.70) | (107.99) | 0.0005 | 0.2889 |

Only subsets with non-missing baseline and week 12 values are included. Data are presented as median (interquartile range) for end point values.
End Point Abbreviations: hsCRP, high-sensitivity C-reactive protein; ICAM-1, intracellular adhesion molecule-1; IL-6, interleukin-6; IQR, interquartile range; Lp-PLA$_2$, lipoprotein-associated phospholipase A$_2$; Ox-LDL, oxidized low-density lipoprotein.

TABLE 11

Median Placebo-adjusted Percent Change From Baseline to Study End in hsCRP Levels (mg/L; ITT Population Subgroups)

| | AMR101 4 g/day | | | AMR101 2 g/day | | | Placebo | | | Median Placebo-adjusted % Change From Baseline | |
|---|---|---|---|---|---|---|---|---|---|---|---|
| | Baseline value (IQR) | End-of-treatment value (IQR) | Change from baseline, % (IQR) | Baseline value (IQR) | End-of-treatment value (IQR) | Change from baseline, % (IQR) | Baseline value (IQR) | End-of-treatment value (IQR) | Change from baseline, % (IQR) | AMR101 4 g/day vs placebo, P | AMR101 2 g/day vs placebo, P |
| MARINE Statin Use | n = 76 | | | n = 73 | | | n = 75 | | | | |
| No statin | 2.2 | 2.2 | 0.0 | 2.2 | 2.5 | 31.7 | 1.8 | 2.4 | 30.8 | −27.4 | −2.7 |
| (n = 56, 52, 55) | (3.05) | (2.55) | (92.15) | (2.40) | (3.15) | (81.50) | (2.50) | (3.60) | (86.11) | 0.0311 | 0.8297 |

TABLE 11-continued

Median Placebo-adjusted Percent Change From Baseline to Study End in hsCRP Levels (mg/L; ITT Population Subgroups)

| | AMR101 4 g/day | | | AMR101 2 g/day | | | Placebo | | | Median Placebo-adjusted % Change From Baseline | |
|---|---|---|---|---|---|---|---|---|---|---|---|
| | Baseline value (IQR) | End-of-treatment value (IQR) | Change from baseline, % (IQR) | Baseline value (IQR) | End-of-treatment value (IQR) | Change from baseline, % (IQR) | Baseline value (IQR) | End-of-treatment value (IQR) | Change from baseline, % (IQR) | AMR101 4 g/day vs placebo, P | AMR101 2 g/day vs placebo, P |
| Statin (n = 19, 18, 17) ANCHOR | 1.9 (3.60) | 1.3 (3.80) n = 226 | −30.6 (80.13) | 1.5 (3.30) | 1.6 (2.20) n = 234 | 11.7 (169.12) | 1.8 (3.20) | 3.5 (4.10) n = 227 | 42.9 (75.00) | −67.9 0.0098 | −33.2 0.1707 |
| Statin Type | | | | | | | | | | | |
| Atorvastatin (n = 38, 42, 44) | 2.1 (2.70) | 1.5 (3.00) | −11.7 (100.00) | 1.7 (2.70) | 2.3 (3.50) | 20.1 (80.75) | 1.6 (3.55) | 2.2 (5.35) | 30.8 (117.86) | −36.7 0.0475 | −9.3 0.6563 |
| Rosuvastatin (n = 52, 53, 52) | 2.6 (3.05) | 1.9 (3.55) | −1.2 (68.87) | 1.6 (1.90) | 2.0 (2.30) | 0.0 (90.95) | 2.5 (4.50) | 2.9 (6.35) | 15.2 (112.74) | −31.4 0.0217 | −11.0 0.3922 |
| Simvastatin (n = 127, 132, 123) | 2.2 (2.70) | 2.2 (2.80) | 0.0 (61.57) | 2.2 (3.90) | 2.7 (3.50) | 11.0 (88.18) | 2.2 (3.80) | 2.6 (3.80) | 13.2 (93.33) | −13.6 0.0755 | −3.8 0.6562 |
| Statin Efficacy Regimen* | | | | | | | | | | | |
| Lower (n = 16, 15, 14) | 2.1 (2.65) | 2.4 (2.45) | 11.9 (45.47) | 1.5 (2.20) | 1.7 (2.70) | 13.3 (89.74) | 2.4 (2.70) | 2.6 (1.90) | 15.7 (75.56) | 4.0 0.8843 | 10.2 0.6467 |
| Medium (n = 132, 145, 134) | 2.2 (2.95) | 1.8 (3.60) | −7.7 (63.96) | 2.3 (4.00) | 2.6 (3.40) | 8.7 (76.67) | 2.2 (4.00) | 2.6 (5.30) | 15.3 (90.80) | −22.8 0.0034 | −8.3 0.2839 |
| Higher (n = 69, 67, 71) | 2.5 (2.80) | 2.0 (2.70) | 0.0 (78.97) | 1.7 (2.10) | 2.2 (3.10) | 16.7 (99.32) | 2.2 (3.30) | 2.6 (4.40) | 28.6 (124.36) | −28.6 0.0210 | −8.3 0.5227 |

Only subsets with non-missing baseline and week 12 values are included. Data are presented as median (interquartile range) for end point values.
*Lower-efficacy statin regimens: simvastatin 5-10 mg; medium-efficacy statin regimens: rosuvastatin 5-10 mg, atorvastatin 10-20 mg, simvastatin 20-40 mg, simvastatin 10-20 mg + ezetimibe 5-10 mg; higher-efficacy statin regimens: rosuvastatin 20-40 mg, atorvastatin 40-80 mg, simvastatin 80 mg, simvastatin 40-80 mg + ezetimibe 5-10 mg.

What is claimed is:

1. A method of lowering a high-sensitivity CRP (hs-CRP) level in a subject having a baseline $HbA_{1c}$ level of at least 6.8 %, the method comprising administering to the subject daily a pharmaceutical composition comprising about 3.5 g to about 4 g of eicosapentaenoic acid or a derivative thereof for a period of time effective to lower the hs-CRP level and maintain or improve glycemic control in the subject.

2. The method of claim 1, wherein the subject has a baseline triglyceride level of about 150-499 mg/dl.

3. The method of claim 2, wherein the subject is on statin therapy or stable statin therapy.

4. The method of claim 1, wherein the pharmaceutical composition comprises at least 90%, by weight of all fatty acids present, ethyl eicosapentaenoate.

5. The method of claim 1, wherein the pharmaceutical composition is encapsulated in a capsule.

6. The method of claim 5, wherein the capsule comprises gelatin.

7. The method of claim 6, wherein 1 to 4 of said capsules are administered to the subject each day.

8. The method of claim 1, wherein the period of time is about 12 weeks and the hs-CRP level is lowered in the subject by at least about 5% compared to a placebo controlled subject who is on stable statin therapy and has not received the pharmaceutical composition.

9. The method of claim 8, wherein the hs-CRP level is reduced by at least about 10%, compared to the placebo controlled subject.

10. A method of lowering high-sensitivity CRP (hs-CRP) in a subject on stable statin therapy with a baseline $HbA_{1c}$ level of at least 6.8% and baseline triglycerides of about 150 to 499 mg/dl, the method comprising administering to the subject a pharmaceutical composition comprising about 3.5 to about 4 g of eicosapentaenoic acid or a derivative thereof for a period of about 12 weeks to reduce the hs-CRP level of the subject compared to baseline and maintain or improve glycemic control in the subject.

11. The method of claim 10 further comprising identifying a baseline $HbA_{1c}$ value of at least 6.8% in the subject before administering the pharmaceutical composition.

12. The method of claim 10 further comprising confirming a reduction in $HbA_{1c}$ level of at least 5% after administering the pharmaceutical composition.

13. The method of claim 12, wherein the hsCRP level is reduced by at least 5% compared to a placebo controlled subject on stable statin therapy and having a baseline $HbA_{1c}$ value of at least 6.8% and baseline triglycerides of about 150-499 mg/dl who has not received the pharmaceutical composition.

14. The method of claim 13, wherein the statin is selected from the group consisting of atorvastatin, rosuvastatin and simvastatin.

15. The method of claim 14, wherein the subject and the placebo controlled subject are not on concomitant niacin or fibrate therapy.

16. The method of claim 13, wherein the subject and the placebo controlled subject have a baseline sitting systolic blood pressure less than or equal to about 160 mmHg and a baseline sitting diastolic blood pressure less than about 100 mmHg.

17. The method of claim 10, wherein the pharmaceutical composition comprises at least 90%, by weight of all fatty acids present, ethyl eicosapentaenoate.

* * * * *